(12) United States Patent
Mojaver et al.

(10) Patent No.: US 12,328,489 B2
(45) Date of Patent: Jun. 10, 2025

(54) IMAGING METHOD AND DEVICE

(71) Applicant: Epilog Imaging Systems, Inc., San Jose, CA (US)

(72) Inventors: Michael Mojaver, Aptos, CA (US); Lance Mojaver, Aptos, CA (US)

(73) Assignee: EPILOG IMAGING SYSTEMS, INC., San Jose, CA (US)

( * ) Notice: Subject to any disclaimer, the term of this patent is extended or adjusted under 35 U.S.C. 154(b) by 0 days.

(21) Appl. No.: 18/139,798

(22) Filed: Apr. 26, 2023

(65) Prior Publication Data

US 2023/0266172 A1    Aug. 24, 2023

Related U.S. Application Data

(63) Continuation of application No. PCT/US2021/056464, filed on Oct. 25, 2021.
(Continued)

(51) Int. Cl.
*H04N 23/11* (2023.01)
*A61B 5/00* (2006.01)
(Continued)

(52) U.S. Cl.
CPC ......... *H04N 23/11* (2023.01); *A61B 5/02055* (2013.01); *A61B 5/021* (2013.01);
(Continued)

(58) Field of Classification Search
CPC .... H04N 23/11; H04N 23/21; A61B 5/02055; A61B 5/021; A61B 5/024;
(Continued)

(56) References Cited

U.S. PATENT DOCUMENTS 5,868,496 A * 2/1999 Spitzberg .............. G01J 5/0003
                                                       250/339.04
6,833,843 B2   12/2004 Mojaver et al.
(Continued)

FOREIGN PATENT DOCUMENTS

CN    104068868 A    10/2014
CN    111583585 A     8/2020
(Continued)

OTHER PUBLICATIONS

International Search Report and Written Opinion, PCT/US2021/056464, dated Jan. 21, 2022, 13 pages.

*Primary Examiner* — Son T Le
*Assistant Examiner* — Janice M Soto
(74) *Attorney, Agent, or Firm* — Potomac Law Group, PLLC; Reza Mollaaghababa; Reza Sadr

(57) ABSTRACT

A remote temperature detector system comprises a reference thermal mass; a temperature sensor in thermal contact with the reference thermal mass for monitoring temperature thereof and generating temperature signals indicative of the monitored temperature; an infrared detector for detecting infrared radiation emitted by an external object and generating infrared detection signals; and a processor in communication with the temperature sensor and the infrared detector to receive the temperature and infrared detection signals, wherein the processor is configured to operate on the infrared detection signals and temperature signals to estimate temperature of the one or more external objects.

16 Claims, 58 Drawing Sheets

Related U.S. Application Data

(60) Provisional application No. 63/244,920, filed on Sep. 16, 2021, provisional application No. 63/185,981, filed on May 7, 2021, provisional application No. 63/105,681, filed on Oct. 26, 2020.

(51) Int. Cl.

| | |
|---|---|
| *A61B 5/0205* | (2006.01) |
| *A61B 5/021* | (2006.01) |
| *A61B 5/024* | (2006.01) |
| *A61B 5/08* | (2006.01) |
| *A61B 5/1455* | (2006.01) |
| *G01J 5/00* | (2022.01) |
| *G01J 5/48* | (2022.01) |
| *G02B 5/30* | (2006.01) |
| *G06T 7/00* | (2017.01) |
| *G06T 7/62* | (2017.01) |
| *G06V 10/143* | (2022.01) |
| *G06V 40/16* | (2022.01) |
| *H04N 23/21* | (2023.01) |

(52) U.S. Cl.
CPC .......... *A61B 5/024* (2013.01); *A61B 5/02433* (2013.01); *A61B 5/0816* (2013.01); *A61B 5/14552* (2013.01); *A61B 5/4875* (2013.01); *A61B 5/7275* (2013.01); *A61B 5/7405* (2013.01); *A61B 5/746* (2013.01); *G01J 5/48* (2013.01); *G02B 5/3025* (2013.01); *G06T 7/0012* (2013.01); *G06T 7/62* (2017.01); *G06V 10/143* (2022.01); *G06V 40/161* (2022.01); *G06V 40/178* (2022.01); *H04N 23/21* (2023.01); *A61B 2503/22* (2013.01); *A61B 2576/00* (2013.01); *G01J 2005/0077* (2013.01); *G06T 2207/10024* (2013.01); *G06T 2207/10048* (2013.01); *G06T 2207/10152* (2013.01); *G06T 2207/30088* (2013.01); *G06T 2207/30196* (2013.01)

(58) Field of Classification Search
CPC .............. A61B 5/02433; A61B 5/0816; A61B 5/14552; A61B 5/4875; A61B 5/7275; A61B 5/7405; A61B 5/746; A61B 2503/22; A61B 2576/00; A61B 5/0077; A61B 5/02416; A61B 5/18; G01J 5/48; G01J 2005/0077; G02B 5/3025; G06T 7/0012; G06T 7/62; G06T 2207/10024; G06T 2207/10048; G06T 2207/10152; G06T 2207/30088; G06T 2207/30196; G06V 10/143; G06V 40/161; G06V 40/178

See application file for complete search history.

(56) References Cited

U.S. PATENT DOCUMENTS

| | | | |
|---|---|---|---|
| 7,274,381 B2 | 9/2007 | Mojaver et al. | |
| 7,274,382 B2 | 9/2007 | Plut | |
| 7,422,365 B2 * | 9/2008 | Chamberlain | G01N 25/72 374/2 |
| 7,573,715 B2 | 8/2009 | Mojaver et al. | |
| 9,113,896 B2 * | 8/2015 | Mulier | A61B 18/1482 |
| 9,137,433 B2 | 9/2015 | Mojaver | |
| 9,485,395 B2 | 11/2016 | Mojaver | |
| 10,148,916 B2 | 12/2018 | Mojaver | |
| 10,348,963 B2 | 7/2019 | Mojaver | |
| 10,404,910 B2 | 9/2019 | Mojaver | |
| 10,599,920 B2 | 3/2020 | Mojaver | |
| 10,924,668 B2 | 2/2021 | Mojaver | |
| 11,706,380 B2 * | 7/2023 | Kuybeda | A61B 5/41 348/77 |
| 2004/0236229 A1 | 11/2004 | Freeman et al. | |
| 2014/0293053 A1 | 10/2014 | Chuang | |
| 2015/0223700 A1 | 8/2015 | Kirenko | |
| 2019/0008437 A1 | 1/2019 | Ben-Ezra et al. | |
| 2020/0202569 A1 * | 6/2020 | Sandsten | H04N 17/002 |
| 2021/0168286 A1 | 6/2021 | Mojaver | |
| 2021/0307621 A1 | 10/2021 | Svenson et al. | |

FOREIGN PATENT DOCUMENTS

| | | |
|---|---|---|
| EP | 3494692 A1 | 6/2019 |
| WO | 2003056516 A1 | 7/2003 |
| WO | 2018027182 A1 | 2/2018 |

* cited by examiner

Wall (27.4 °C)

0.25 ft (36.0 °C)

0.25 ft (36.0 °C)

1 ft (36.0 °C)

4 ft (35.0 °C)

8 ft (34.5 °C)

10 ft (34 °C)

14 ft (33.0 °C)

18 ft (32.2 °C)

22 ft (31 °C)

26 ft (30 °C)

IMAGING METHOD AND DEVICE

RELATED APPLICATIONS

This non-provisional application is a continuation of the International Application No. PCTUS2021056464, which was filed on Oct. 25, 2021, was entitled "Imaging Method and Device," and itself claimed the benefit of priority in the following three provisional applications: U.S. Provisional Application No. 63/105,681, filed on Oct. 26, 2020, and entitled "Infrared Thermographic Imaging System"; U.S. Provisional Application No. 63/185,981, filed on May 7, 2021, and entitled "Imaging Method and Device"; and U.S. Provisional Application No. 63/244,920, filed on Sep. 16, 2021, and entitled "Imaging Method and Device," The entire contents of all of the above-listed four Applications are being incorporated herein by reference.

TECHNICAL FIELD

The present disclosure relates generally to infrared (IR) thermographic imaging systems for measuring temperatures of external objects. Moreover, the disclosure also relates to imaging systems that allow measuring a variety of biometric parameters of subjects.

BACKGROUND

Infrared thermographic (IRT) imaging systems are non-contact and non-invasive remote sensing systems that can help solve numerous industrial and medical challenges. The IRT imaging systems are used in search and rescue operations, maritime navigation, road safety, and leak detection to help identify hot and cold spots. In bio-medical IRT applications, they can provide temperature maps, for example when used in cancer detection, vascular imaging, wound assessment, skin temperature sensing, and fever detection/screening.

The conventional IRT imaging systems suffer, however, from a number of shortcomings. For example, their calibration can be cumbersome, and they are subject to electronic drift and measurement bias with respect to the distance to a target. They are also unable to respond to emissivity changes.

Accordingly, there is a need for improved infrared thermionic imaging systems.

SUMMARY

In one aspect, the present disclosure provides an IRT imaging system for measurement of temperatures of external objects. In embodiments, such an IRT imaging system can provide non-contact, accurate and reliable temperature measurements of external objects. For example, as discussed in more detail below, in some embodiments, a system according to the present teachings includes an integrated black body probe (e.g., a system in which the black body probe and the infrared detector are disposed in the same housing), the temperature of which is measured and/or controlled in-situ, thereby providing a reliable reference for calibrating the detector's signals. Further, in some such embodiments, the system can include a distance sensor to measure the position of an object for which temperature measurement is desired. Such a position measurement allows for compensating the intensities of the signals generated by the infrared detector based on the distance between the detector and the object, thereby reducing, minimizing, and preferably eliminating errors in the calculation of the object's temperature based on the infrared signal. In addition, in some embodiments, a system according to the present teachings can include a humidity detector as well as a sensor for measuring the air temperature in-situ. The system can then employ such measurements for normalizing (correcting) the temperatures calculated based on the intensity of the detected IR signals. In this manner, a system according to the present teachings allows for taking into account a variety of environmental factors that could affect the calculation of an object's temperature based on the detection of infrared radiation emitted by that object.

Further, a system according to the present teachings can estimate the emissivity of an external object by using Artificial Intelligence to determine the type of object and its orientation (pose) relative to the object. The emissivity and pose of an object can impact the efficiency of heat transfer from the source and therefore the apparent temperature of the object.

Further, in some embodiments, a system according to the present teachings can improve on the emissivity estimate of an external object, by determining the reflectivity of the object, using polarized light and dual stereo polarization imaging. The reflectively of an object can impact the efficiency of heat transfer from the object and therefore the apparent temperature of the object in two different ways. First, reflective objects can reflect heat from other sources, for example a hot lamp nearby. Second, increased reflectivity in biological subjects may indicate a wet surface and associated cooling phenomena, which will mask the true internal temperature of the body.

In some embodiments, an imaging system according to the present teachings may include a reference thermal mass, a temperature sensor in thermal contact with the reference thermal mass for monitoring temperature thereof and generating temperature signals indicative of the monitored temperature, an infrared detector for detecting infrared radiation emitted by one or more external objects and generating infrared detection signals, and a processor in communication with the temperature sensor and the infrared detector to receive the temperature and infrared detection signals, wherein the processor is configured to operate on the infrared detection signals and temperature signals to estimate temperature of the one or more external objects.

In some embodiments, the reference thermal mass includes any of anodized sheet of copper or aluminum. The anodized sheet of copper or aluminum is configured to be heated by thermal energy generated from the processor. Further, in some embodiments, the reference thermal mass includes a temperature regulator in communication with the anodized sheet of copper or aluminum and configured to provide control signals for maintaining the temperature of the anodized sheet at the target temperature. In some embodiments, a fan may be further provided, such that the temperature regulator controls the fan to adjust air flow and thereby maintain the temperature of the reference thermal mass at the target temperature.

In some embodiments, the infrared detector includes an uncooled microbolometer. In some embodiments, the infrared detector includes an array of uncooled microbolometers.

In some embodiments, the temperature sensor includes a thermocouple and/or an integrated chip sensor. The processor can be configured to calibrate the infrared detection signals based on the temperature signals provided by the temperature sensor.

In some embodiments, the system includes a distance sensor to measure a distance to the one or more external objects. The distance sensor can include a LIDAR sensor configured to generate signals indicative of distance between a subject and the infrared detector. Further, the processor can be configured to receive the signals generated by the LIDAR sensor and employ the signals to compensate the infrared detection signals for the distance between the infrared detector and the one or more external objects.

In some embodiments, the system includes an ambient temperature sensor and an ambient humidity sensor. Accordingly, the infrared detection signal can be further compensated by an ambient temperature signal and/or an ambient humidity signal acquired by the ambient temperature sensor and the ambient humidity sensor, respectively.

In some embodiments, the one or more external objects can include a human body. The processor can be configured to adjust emissivity assigned to the one or more external objects based on one or more of illumination conditions, geometric properties, and age.

In some embodiments, the system further includes a visible imaging device. In some embodiments, the system includes a first visible spectrum imaging device, a second visible spectrum imaging device, a first polarizer disposed in front of the first visible spectrum imaging device for polarizing light in a first direction, and a second polarizer disposed in front of the second visible spectrum imaging device for polarizing light in a second direction perpendicular to the first direction. The processor can be configured to adjust emissivity assigned to the one or more external objects based on visible spectrum imaging signals acquired from the first visible spectrum imaging device and the second visible spectrum imaging device. In some embodiments, emissivity can be adjusted for water content present on the one or more external objects based on the visible spectrum imaging signals acquired from the first visible spectrum imaging device and the second visible spectrum imaging device.

In some embodiments, the techniques described herein relate to a system for monitoring a human operator of critical equipment, the system including: an imaging module; a biometric measurement module; a risk detection module; and a risk response module, wherein: the imaging module includes: a multi-spectral light source configured to emit light in a first spectral wavelength range for illuminating at least a portion of the human operator; a camera configured to detect light received from the human operator in response to the illumination and in a second spectral wavelength range; an imaging data generator configured to generate image data based on the emitted light and detected light; the biometric measurement module is configured to: receive the image data; and based on the image data, perform at least one biometric measurement on the human operator; the risk detection module is configured to: based on the biometric measurements establish a safety risk associated with the human operator; and the risk response module is configured to: based on the safety risk generate a risk response.

In some embodiments, the techniques described herein relate to a system, wherein: the biometric measurement includes at least one of measuring an oxygen level of blood, a heartbeat rate, blood pressure, a body temperature, and a breathing rate.

In some embodiments, the techniques described herein relate to a system, wherein: the critical equipment includes at least one of an airplane, a heavy machinery, a train, an air traffic control system, a car, and a bus.

In some embodiments, the techniques described herein relate to a system, wherein: the safety risk includes at least one of fatigue, a seizure, a heart-attack or a stroke.

In some embodiments, the techniques described herein relate to a system, wherein: the risk response includes at least one of generating an audio alarm, halting the equipment, transferring control to another operator, overriding the operator over the equipment, and sending an alarm message.

In some embodiments, the techniques described herein relate to a system, wherein: the imaging module is configured to be installed facing the human operator.

In some embodiments, the techniques described herein relate to a system, wherein: the first spectral wavelength range includes a near IR spectrum region; the second spectral wavelength range includes the near IR spectrum region; and the biometric measurement module is configured to perform pulse oximetry.

In some embodiments, the teachings described herein relate to a system, wherein the biometric measurement module is further configured to determine the body temperature.

In some embodiments, the teachings described herein relate to a system, wherein the biometric measurement module is further configured to determine the heart rate.

In some embodiments, the teachings described herein relate to a system, wherein: the imaging module is a first imaging module; the light source is an IR strobe configured to emit light in a near IR spectral region; the camera is an IR sensitive camera; the system further includes a second imaging module that includes: an RGB strobe; and a visible light sensitive camera configured to: detect visible light in the visible electromagnetic wavelengths range; and block IR light in the IR spectrum region; and the biometric measurement module is configured to; receive data from the IR sensitive camera and the visible light sensitive camera; and based on the received data determine the biometric parameter.

In some embodiments, the teachings described herein relate to a system, wherein the biometric measurement module is configured to perform pulse oximetry by comparing an IR reflectance derived from data received from the IR sensitive camera and red light reflectance derived from the data received from the visible light sensitive camera.

In some embodiments, the teachings described herein relate to a system, wherein: the system further includes a thermal camera configured to receive thermal radiation; and the biometric measurement module is further configured to use data received from the thermal camera to determine the biometric parameter.

In some embodiments, the teachings described herein relate to a system, further including an alarm signal mechanism for raising an alarm when the determined biometric parameter is in an alarm range.

In some embodiments, the teachings described herein relate to a system, further including a display configured to display information related to the biometric parameter.

In some embodiments, the teachings described herein relate to a system, wherein the IR strobe and the RGB strobe alternate in sending signals.

In some embodiments, the teachings described herein relate to a system, wherein the biometric measurement module includes an artificial intelligence module.

In some embodiments, the teachings described herein relate to a system, wherein: the first and the second ranges of electromagnetic wavelengths include a green wavelength; and the biometric measurement module is configured to determine the heartbeat rate based on a reflectance of the green wavelength.

In some embodiments, the teachings described herein relate to a system, wherein the biometric measurement module is configured to determine the heartbeat rate based on a time dependence of the image data.

In some embodiments, the teachings described herein relate to a system, wherein the biometric measurement module is configured to detect an extremity of a subject and determine the biometric parameter by analyzing image data received from a skin portion of the extremity.

In some embodiments, the teachings described herein relate to a system, wherein the biometric measurement module is configured to detect a face of a subject and determine an age of the subject based on an image of the face.

In some embodiments, the teachings described herein relate to a system, wherein the biometric measurement module is configured to estimate a volume of a subject and based on the volume estimate a weight of the subject.

In some embodiments, the teachings described herein relate to a system, wherein: the RGB strobe emits light with a first polarization; the IR sensitive camera blocks light with a second polarization; the visible light sensitive camera blocks light a third polarization that is perpendicular to the second polarization; the first polarization is parallel to the second polarization or to the third polarization; and the biometric parameter includes the skin moisture.

Notably, the present disclosure is not limited to the combination of the elements as listed above and may be assembled in any combination of the elements as described herein. Other aspects of the disclosure are disclosed herein.

BRIEF DESCRIPTION OF THE DRAWINGS

The drawings are not necessarily to scale or exhaustive. Instead, emphasis is generally placed upon illustrating the principles of the embodiments described herein. The accompanying drawings, which are incorporated in this specification and constitute a part of it, illustrate several embodiments consistent with the disclosure. Together with the description, the drawings serve to explain the principles of the disclosure.

DETAILED DESCRIPTION

Figure 1:
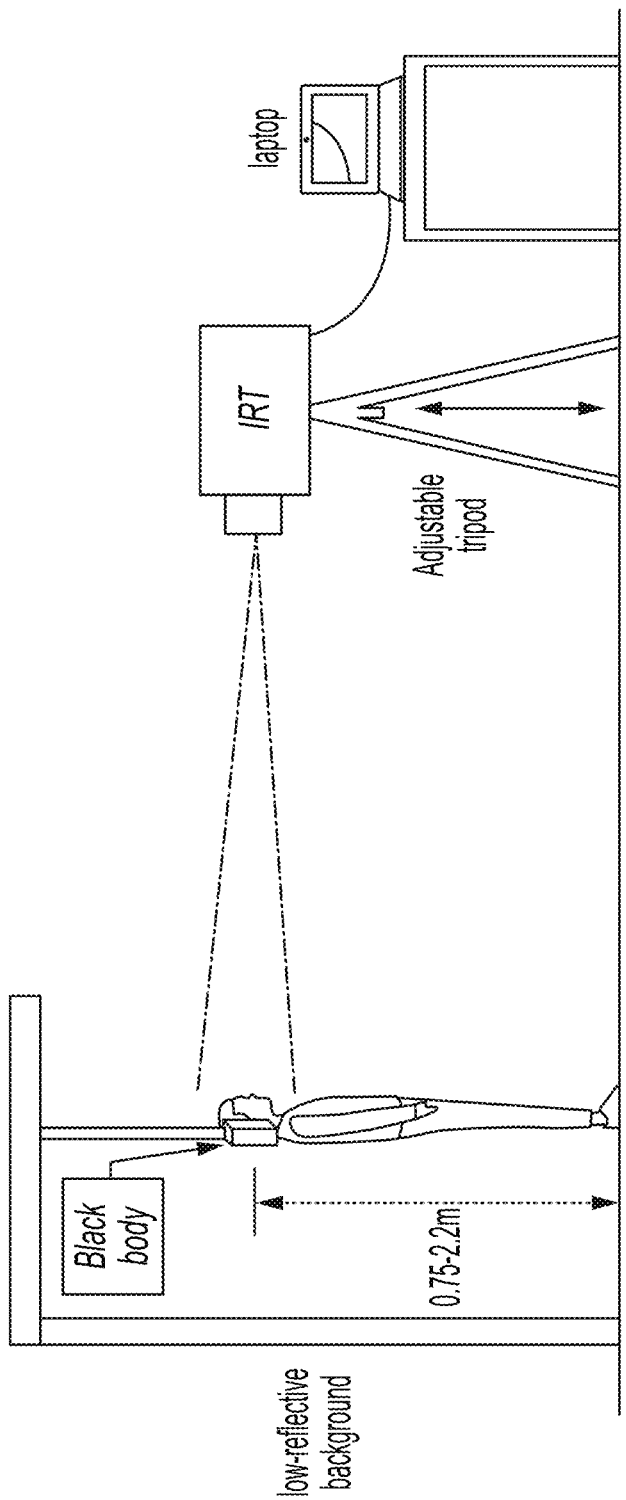
FIG. 1 shows a schematic view of a prior art IRT imaging system, which utilizes an external dedicated electronic black body source of a known temperature in the field of view as a calibration reference.

Advantages and features of the present disclosure and a method of achieving the same will become apparent with reference to the accompanying drawings and exemplary embodiments described below in detail. However, the present disclosure is not limited to the exemplary embodiments described herein and may be embodied in variations and modifications. The exemplary embodiments are provided merely to allow one of ordinary skill in the art to understand the scope of the present disclosure, which will be defined by the scope of the claims. Accordingly, in some embodiments, well-known operations of a process, well-known structures, and well-known technologies will not be described in detail to avoid obscure understanding of the present disclosure. Throughout the specification, same reference numerals refer to same elements.

The terminology used herein is for the purpose of describing particular embodiments only and is not intended to be limiting of the disclosure. As used herein, the singular forms "a," "an," and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items.

With the rise of global pandemics, IRT imaging is being exploited to detect Elevated Body Temperatures (EBT) and help screen people with suspected or active infectious diseases. Fever is a reliable indication that a person or an animal is fighting an infection. IRT and non-contact temperature screening have been explored since the outbreak of Severe Acute Respiratory Syndrome (SARS) in 2002, H1N1 flu in 2009, Middle East Respiratory Syndrome (MERS) in 2012, Ebola in 2014, Zika in 2015, and Covid-19 in 2020.

Although not every infected person always displays an EBT, the advantage of IRT imaging systems in public places (e.g. airports, mass transit, hospitals, schools, sports facilities, houses of worship, etc.) is that it provides the opportunity for rapid, inexpensive, and non-contact mass screening without the risk for harm to the human operator, who can remain at a safe distance. In practice, however, challenges have been encountered in deploying IRT screening technology. False manufacturer accuracy claims, environmental variations, and inconsistent examination techniques may prevent achieving consistent results with outside laboratory-like conditions.

Similarly, other rapid screening methods for infected individuals have their own unique challenges. For example, antigen tests that rapidly detect the presence of viral proteins in biological samples are not as sensitive or reliable as the more expensive and slower nucleic acid amplification tests such as polymerase chain reaction (PCR) tests. The development of a single, fast, inexpensive, and reliable test for the presence of infectious diseases has been challenging, and multi-tiered approaches and improving technologies are some of the promising paths forward.

Aspects of the present disclosure provide improved infrared thermographic (IRT) devices for EBT detection, e.g., by compensating for variations in environmental and examination conditions that could otherwise result in delivering inconsistent results. Such improvements can help facilitate the adoption of IRT devices for temperature measurement in all public places.

In some embodiments, the IRT imaging systems according to the present teachings can overcome the shortcomings of prior art IRT systems, such as, electronic drift, emissivity, and distance corrections by including a black body reference (herein also referred to as a reference thermal mass) and Laser Imaging Detection and Ranging (LIDAR) integrated into the system, and processing the data based on Artificial Intelligence (AI).

In many conventional IRT systems utilizing microbolometer detector arrays, to compensate for drift, a mechanical shutter of known temperature is positioned between the detector array and a lens that focuses the radiation onto the microbolometer array. Periodic shutter activation (i.e. the shutter moving to a closed position in which it substantially blocks external light from reaching the image sensor) allows recalibration of the signals generated by the microbolometer array. The closed shutter is used as a uniform reference image of known temperature to calculate drift correction. More frequent calibration operations produce more accurate results, however, at the expense of blocking the view of the camera more often on every shutter calibration closure. The typical accuracy range ±2° C. to ±3° C. for microbolometer requires regular and frequent mechanical shutter calibration.

To partly solve the problem of periodic blocking, semi-transparent shutters have been attempted. However, the semi-transparent shutters significantly degrade the image quality of the detector array. Complex mathematical modeling of drift by reading casing and/or die temperatures and "blind" pixels arranged on the Focal Plane Array (FPA) have been attempted as well. However, the very large number of variables and permutations including lenses and atmospheric variations make such calibration methods of limited usefulness in practice.

A conventional method to compensate for electronic drift in an IRT system and achieve temperature readings at a higher accuracy relies on utilizing an external dedicated electronic black body source that can be preset to a known reference temperature and placed in the field of view, as shown in FIG. 1.

The operator manually selects the black body in the field of view of the IRT device software and enters the known reference temperature of the black body. The black body reference is subsequently used to correct for drift in the camera and atmospheric variations. Although using a black body source may improve the accuracy of such a conventional IRT device, it introduces many practical limitations, such as:

1. Subjects must be channeled (queued) into a measurement area where the black body is disposed, which disrupts the normal flow of traffic, in what is often referred to as a "choke point".
2. The black body reference and the camera must be maintained in a predetermined geometric relation relative to one another. If the camera or the black body is moved out of position, the system needs to be recalibrated.
3. If the black body temperature changes for any reason and the IRT system is not synched, the system needs to be recalibrated.
4. Black body references add extra expenses, often costing as much as the IRT camera system.

Since human bodies can readily be identified using artificial intelligence software algorithms and have a statistical average temperature of 37° C. (98.6° F.) with high emissivity, they can be approximated as a black body reference. To reduce system cost and complexity, many manufacturers have resorted to relying on the flow of human subjects in the IRT camera field of view as a way of calibrating the system, instead of utilizing a black body calibration source. However, in addition to posing ethical issues, using human bodies as a calibration source can result in inconsistent calibration. Moreover, the required regular and continuous flow of people in the field of view is not always assured, and there are numerous situations where the system will behave in a faulty manner. As an example, if one or more people with a fever pass through the system's field of view following a 5-10 second pause in traffic flow, they would likely be identified as normal by the system.

Typically, most manufacturers highest accuracy specifications are only valid at a single distance. The variation in measured temperature is typically compounded by the following two effects:

1) Emissivity Changes by Distance

The air between a target object and an IRT device can absorb and emit thermal energy as the radiation passes through it. Such absorption or emission of thermal energy varies depending on the air temperature, density, humidity, and the distance. Accordingly, the air has a strong impact on the temperature measurements. Moving subjects present an extra challenge as fluctuating temperature readings can be recorded at different distances from the detector.

2) Parallax Between Visible and Thermal Cameras

Figure 2:
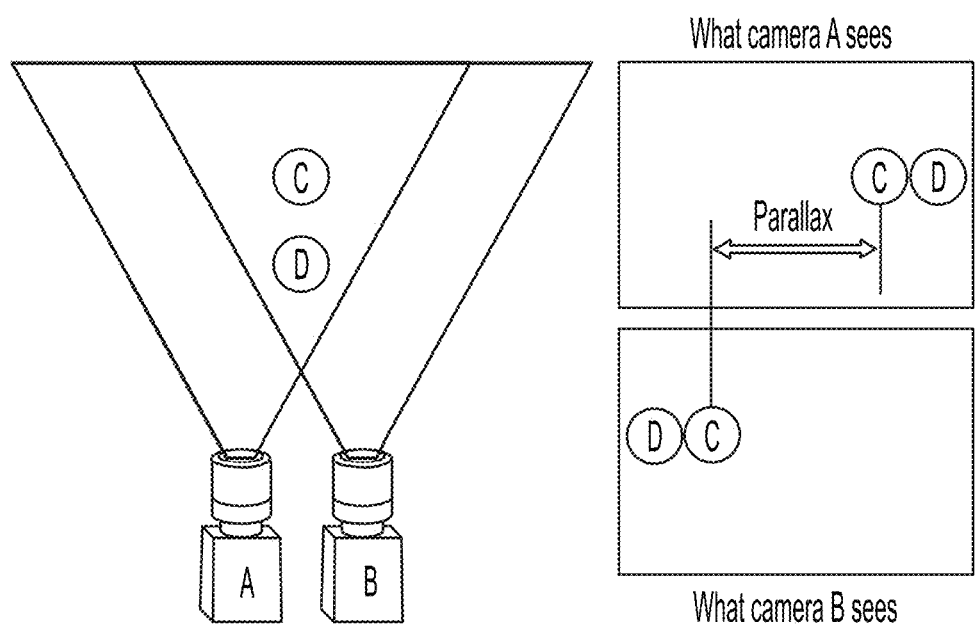
FIG. 2 depicts parallax between visible and thermal cameras in the prior art system depicted in FIG. 1.
Figure 3:
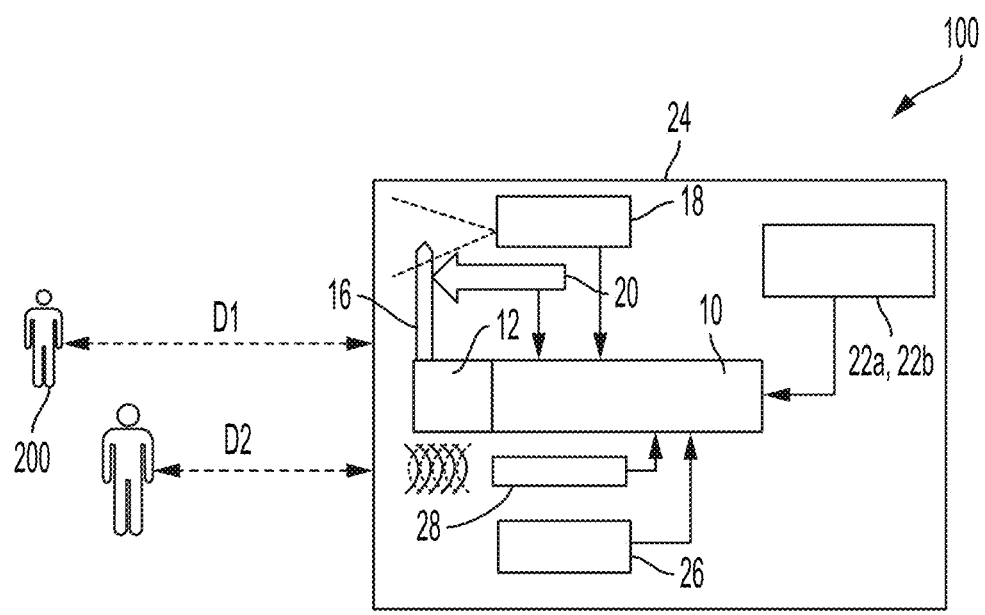
FIG. 3 schematically depicts an example of an embodiment of an IRT imaging system according to the present teachings.

Because thermal cameras typically have low resolution (tens to hundreds of thousands of pixels), most IRT systems for fever detection include both visible and thermal cameras. The visible camera (i.e., adapted to detect primarily in the visible light spectrum) typically has millions of pixels in resolution and is used for face detection and identification. The thermal camera (i.e., adapted to detect substantially in the infrared spectrum) collects pixels in a Region of Interest (ROI), e.g., a face, to estimate a body temperature. Since there is parallax between the visible and thermal cameras, as shown in FIG. 2, the corresponding regions in the two sensors have offsets depending on the distance to the subject, which produces unreliable results.

In order to address the aforementioned issues among others, some embodiments of a system according to the present teachings combine LIDAR distance measurement, a black body reference (herein also referred to as a reference thermal mass) whose temperature is actively regulated or measured in-situ, and AI-based processing algorithms within an IRT imaging system.

Hereinbelow, an IRT imaging system according to an example of an embodiment of the present teachings will be described by reference to FIGS. 3-8. The illustrated IRT imaging system 100 includes a processor 10 (e.g., an AI processor), a heat sink 12 that is in thermal communication with the processor 10 and dissipates the heat generated by the processor 10. The illustrated IRT imaging system 100 further includes a cooling device 14 (e.g., a fan or a thermoelectric cooler) for regulating the temperature of the heat sink 12. The illustrated IRT imaging system 100 further includes a black body probe or a reference thermal mass 16 (such as an anodized sheet of copper or aluminum coupled to or integrated with the heat sink 12) that can be used to calibrate the signals generated by an IR detector 18, as discussed in more detail below.

A temperature sensor 20 (e.g., a thermocouple, or an integrated chip (IC) thermometer) is in thermal contact with the reference thermal mass 16 to measure a temperature thereof. In some embodiments, a feedback system receives the measured temperature and maintains the heat sink 12 and the reference thermal mass 16 at a preset temperature. In such embodiments, the feedback system may be provided separately, and in other embodiments, the processor 10 may be configured to perform the feedback control. All embodiments of the system include a processing device that normally generates heat during its operation. The heat from the processor is transferred to the heat sink 12 which typically reaches a steady state temperature of between 0° C. to +50° C. depending on the ambient temperature.

Although it is not required, in some embodiments, the temperature of the heat sink 12 and the reference thermal mass 16 are regulated, e.g. by changing the fan speed. Regardless, the heat sink 12 temperature is continuously or intermittently monitored to provide a relatively stable and accurately known temperature reference. In some embodiments, the temperature of the heat sink 12 and the reference thermal mass 16 are regulated using a heater (e.g., a resistively heated heating element, an infrared heater, or the like) that is configured to provide thermal energy in addition to the processor 10 to regulate the temperature of the heat sink 12 and the reference thermal mass 16.

The IRT imaging system 100 further includes at least one ambient air temperature sensor 22*a* and/or humidity sensor 22*b*. The temperature sensor 22*a* and the humidity sensor 22*b* can be positioned in proximity of an inlet provided in a housing 24, in which the components of the system are disposed, and through which air flows into the housing 24 to measure the temperature and/or humidity of the ambient air and use these temperature measurements to compensate for the infrared detection signals so as to obtain more accurate temperature measurements.

In some embodiments, as described above, the heat sink 12 and the reference thermal mass 16 are integrally formed, and the feedback system and/or the processor 10 may be configured to control the cooling device 14 (e.g., a fan) to adjust the amount of air flow drawn into the housing 24 in order to regulate the temperature of the heat sink 12 and the reference thermal mass 16 at the preset temperature.

The IRT imaging system 100 includes an infrared detector 18, e.g., an uncooled microbolometer array, that is positioned to receive infrared radiation from a target subject/object 200 within a typical 40° to 90° field of view and to generate detection signals in response to the detection of the infrared signals.

Figure 4:
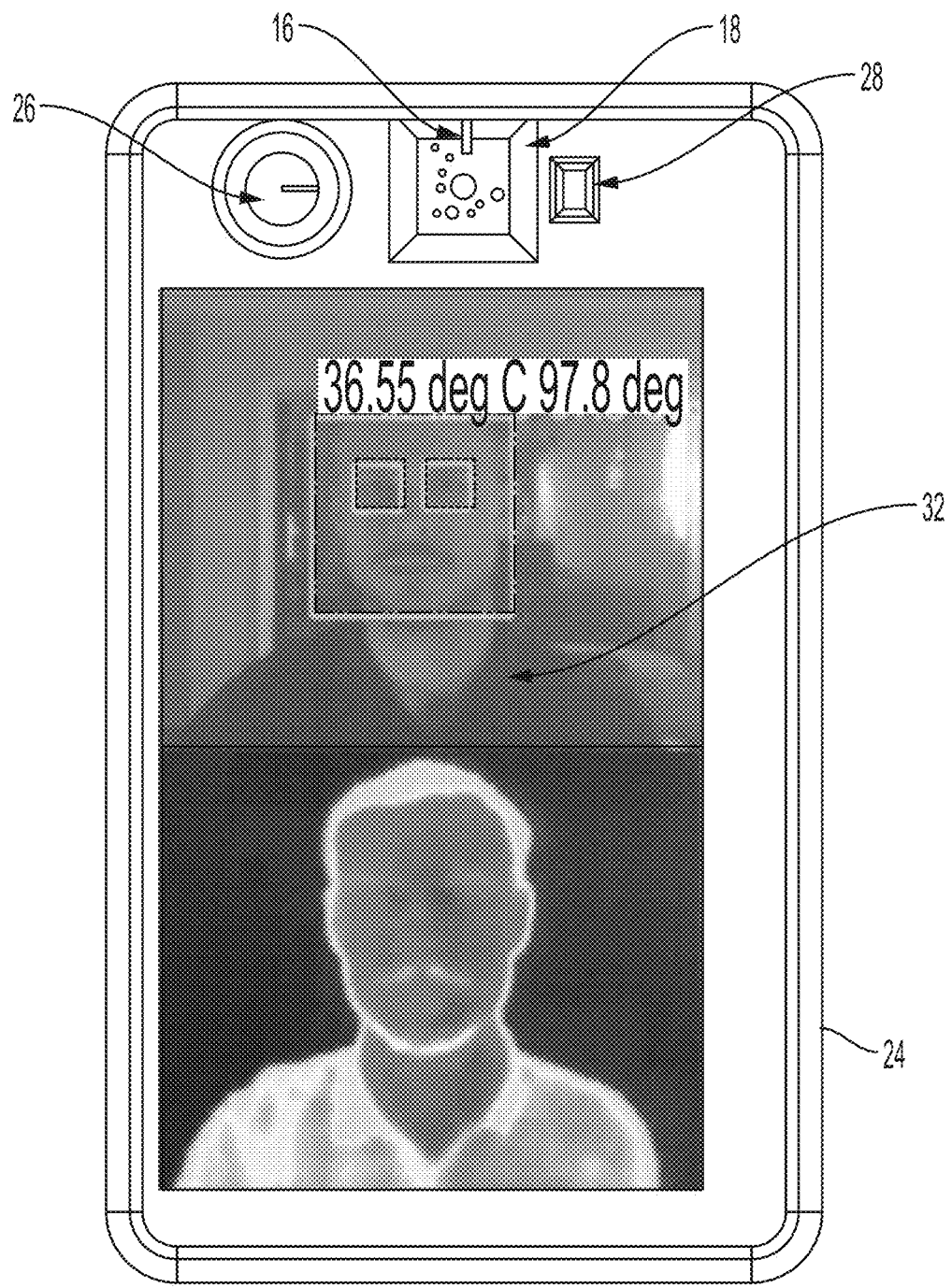
FIG. 4 shows a front view of an example of an embodiment of an IRT imaging system according to the present teachings.
Figure 5:
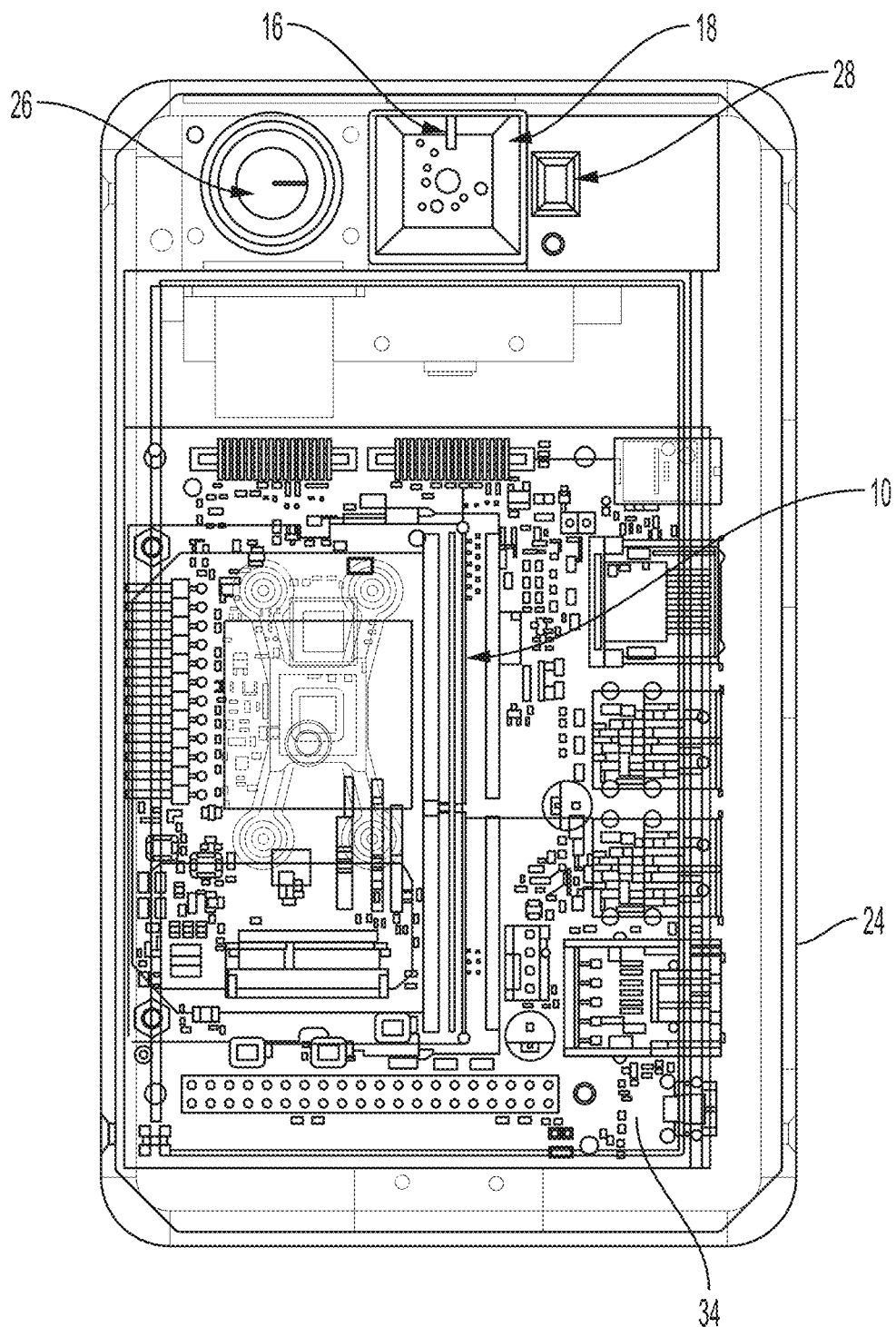
FIG. 5 shows a front view of an example of an embodiment of an IRT imaging system according to the present teachings with the display removed for illustration purposes.
Figure 6:
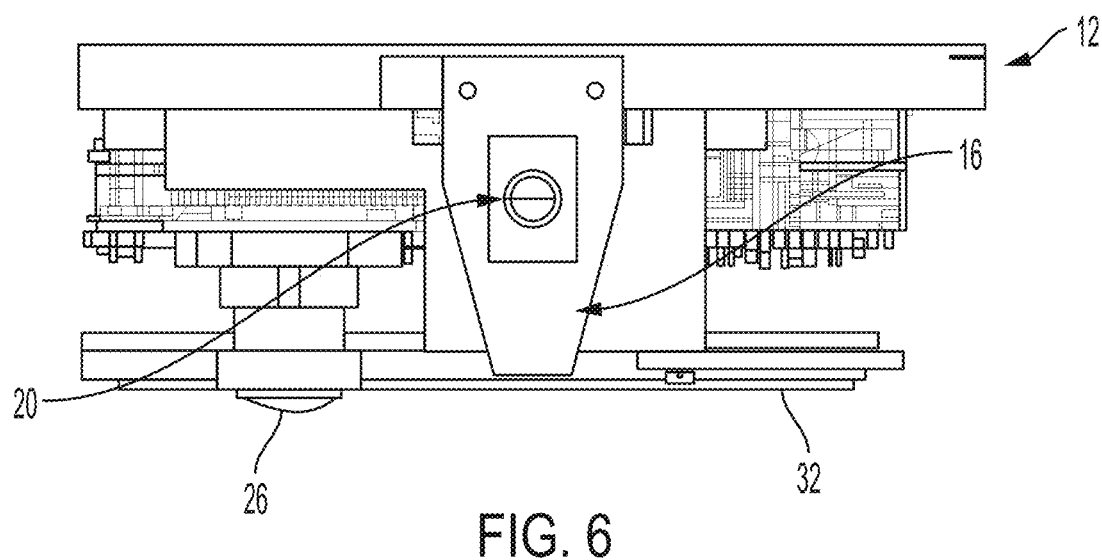
FIG. 6 schematically depicts a top view of the internal structure of an embodiment of IRT imaging system according to the present teachings.
Figure 7:
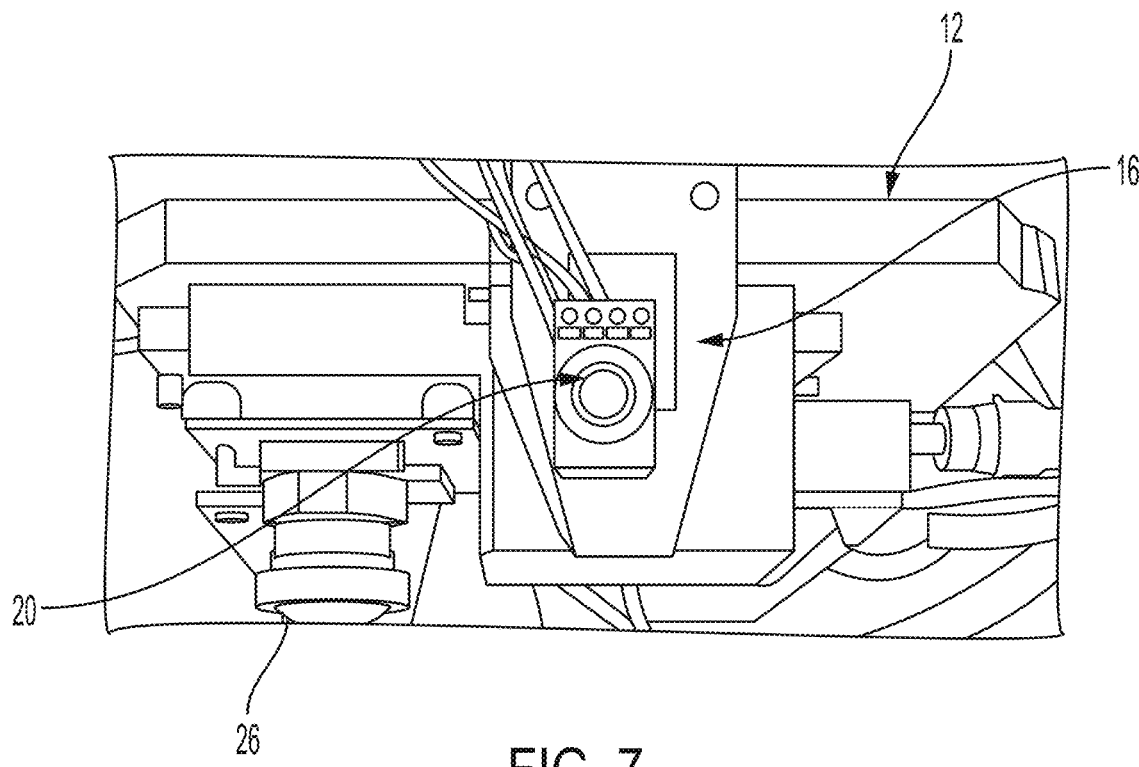
FIG. 7 shows a photograph of the top view of the internal structure of an embodiment of an IRT imaging system according to the present teachings.
Figure 8:
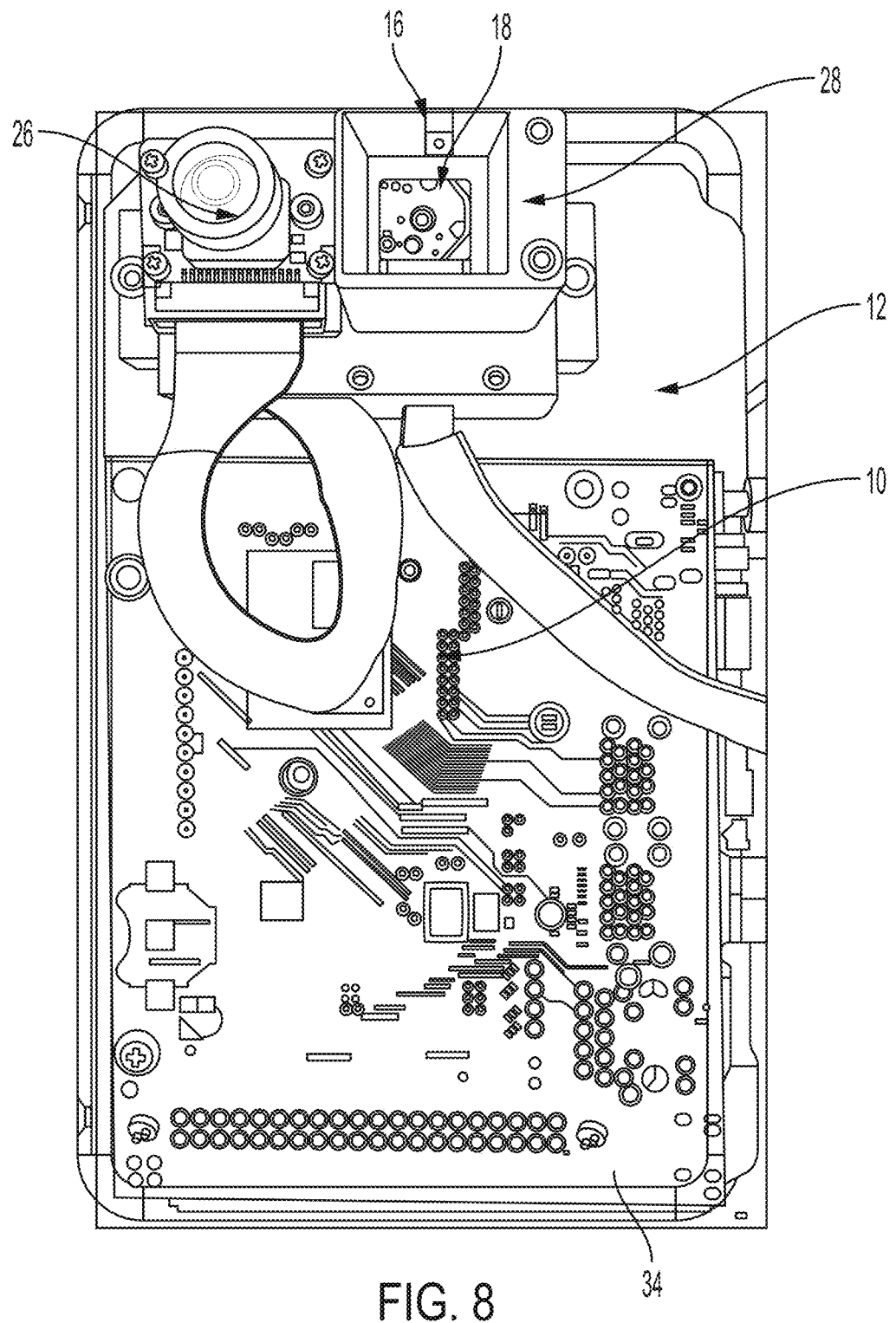
FIG. 8 shows a photograph of the internal structure of an embodiment of an IRT imaging system according to the present teachings.

Further, the IRT imaging system 100 includes one or more visible imaging devices 26 (e.g., single or dual polarized cameras). In some embodiments, the visible images generated by these cameras can be used to identify a human face within a field of view of 40° to 90° typically. As shown in FIG. 4, the system can concurrently display the visible and infrared images on a display 32.

The IRT imaging system 100 includes a distance sensor 28, which is incorporated in this embodiment in the same housing 24 as the infrared detector 18, the temperature sensor 20, and the reference thermal mass 16. In this embodiment, the distance sensor 28 is implemented as a LIDAR sensor. The output of the LIDAR sensor can be employed to determine the distance from a subject to the infrared detector 18. The measured distance can then be used to correct for the effects of environmental factors, such as humidity, on the temperature derived from the signals generated by the infrared detector 18.

In addition, the IRT imaging system 100 further includes a power source (e.g., a battery), one or more memories operatively coupled to the processor 10 to store program instructions to operate the system and/or measurement data, wireless/wired communication devices (e.g., a transmitter, a receiver, and/or a data I/O component) to communicate with other electronic devices, and a user interface (e.g., a touchscreen). These electronic components are mounted on a circuit board 34.

Due to the integration of the reference thermal mass 16 and the distance sensor 28 within the system (e.g., within the same housing), the IRT imaging system 100 according to an embodiment of the present teachings can minimize, reduce, and preferably eliminate the effects of electronic drift and/or measurement bias that can be caused as a result of variations in the distance (D1 and D2 shown in FIG. 3) between the subject 200 and the infrared detector 18, and temperature drift of a black body reference, on the subject's temperature computed based on the detected infrared signals.

Unlike the conventional IRT systems, which employ external, stand-alone black body calibrators, that are susceptible to temperature drift due to ambient changes, e.g., temperature changes, an IRT imaging system 100 according to the present teachings employs an integrated reference thermal mass 16 whose temperature can be measured, e.g., on a periodic basis, and used as a reference to calibrate the system. In some embodiments, the temperature of the thermal mass is actively maintained at a target temperature irrespective of ambient changes, e.g., temperature changes, though in other embodiments such active temperature control is not utilized.

In this embodiment, a heat sink 12 that is in thermal contact with an AI processor 10 functions as the reference thermal mass 16 to provide a reference calibration temperature. By way of example, the heat sink 12 may be maintained at a similar temperature as that of the human body in steady state and may be controlled within a range of 5-10° C., for example, by adjusting the air flow rate, e.g., generated by a fan (e.g., the cooling device 14), within the device and/or via a Peltier-effect thermoelectric cooler/heater. In some embodiments, the temperature of the heat sink 12 is not actively regulated. Rather, the temperature of the heat sink 12 is periodically or substantially continuously measured (e.g., at a maximum rate allowed by a temperature sensor), and the calibration of the system is updated based on the measured temperatures of the heat sink 12.

For example, the temperature sensor 20 can continuously or intermittently measure the temperature of the heat sink 12, thereby providing a point of temperature reference. The data from the infrared detector 18 is then calibrated or compensated based on the temperature reference point on a real-time basis. This approach allows for contactless temperature measurements with improved accuracy from a low-cost long wave infrared (LWIR) imaging device, without requiring an external black body reference device.

Figure 9:
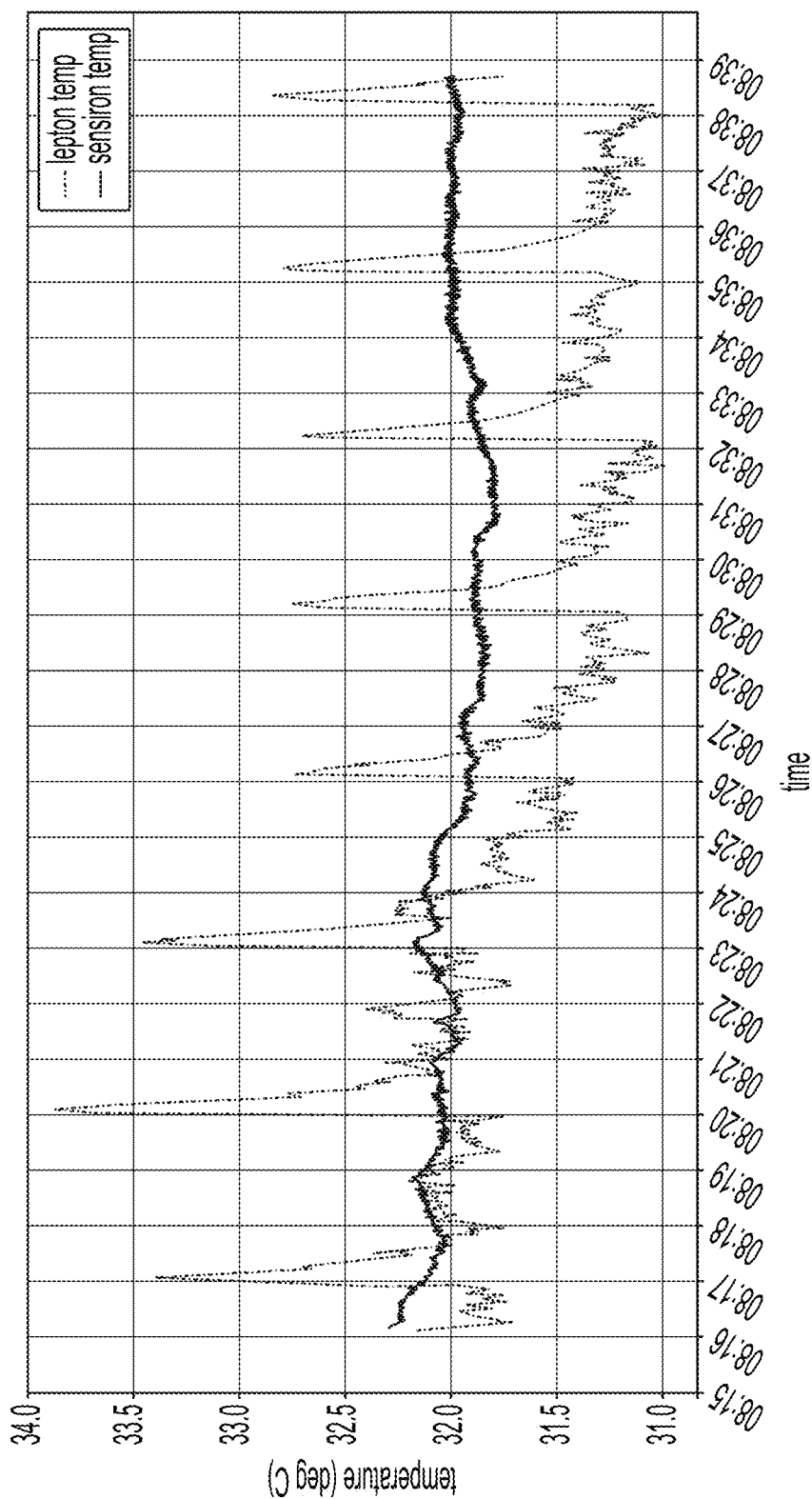
FIG. 9 shows high-variance measurements from a long-wave IR camera (blue) of an external fixed black body source versus an IC temperature sensor (orange) measurement of the system internal black body source over a 25-minute time period.
Figure 10:
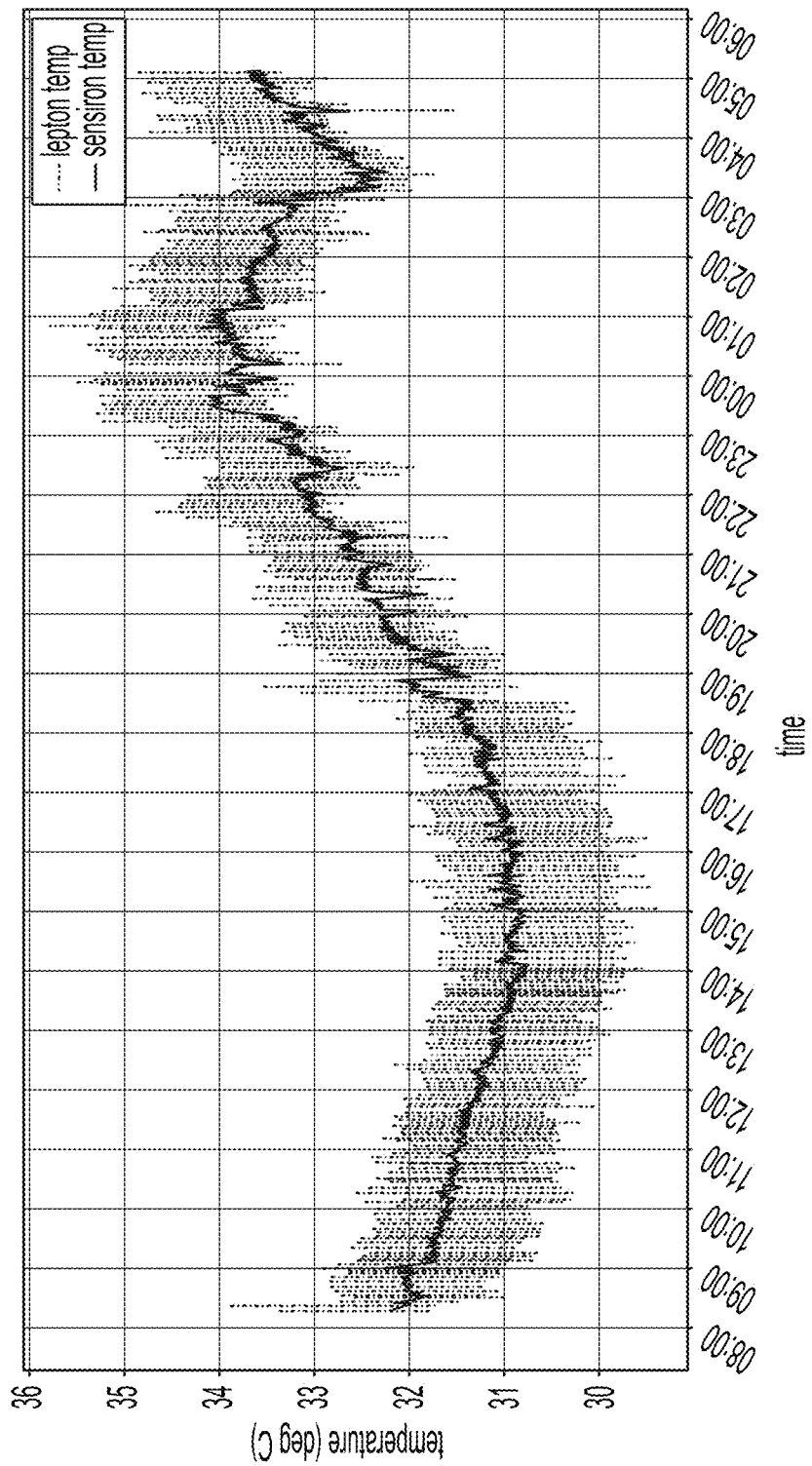
FIG. 10 shows high-variance measurements from a long-wave IR camera (blue) of an external fixed black body source versus an IC temperature sensor (orange) measurement of the system internal black body source o over a 24 hour time period.

FIGS. 9 and 10 illustrate the high-variance measurements from the LWIR camera (blue) and the low-variance measurements from the IC temperature sensors (orange) without the temperature corrections according to the aspects of the present teachings. The LWIR measurements, therefore, rely on periodic temperature calibration using a mechanical shutter, which is indicated by cyclic temperature peaks occurring every ~3 minutes shown in FIG. 9. The horizontal axis represents measurement time, and the vertical axis represent temperatures in Celsius.

FIG. 9 shows the measurement results over a 25-minute time period, and FIG. 10 shows measurement results over a 24-hour time period. In FIG. 9, the cyclic temperature peaks are due to closure of the mechanical shutter, which indicate the mechanical shutter operation for recalibration. Such periodic closure of the mechanical shutter is used in some conventional systems for calibration. FIGS. 9 and 10 indicate that the temperature measurements with the LWIR cameras, without better temperature corrections such as provided in the present disclosure, can deviate from the IC temperature measurements by up to 1° C.

Although in many situations the impact of air on the temperature measurement is negligible, air absorbs and emits thermal energy as thermal radiation is transmitted through it. The absorption or emission of thermal energy depends on the temperature, density, and humidity of the air, and also on the amount (e.g., mass) of air between the thermal radiation source and the detector. Therefore, the distance between a subject and the detector can bias the temperature measurements. Furthermore, moving subjects present an extra challenge, and the temperature readings can fluctuate as the distance to the moving subject from the imaging sensor varies.

Figure 11A:
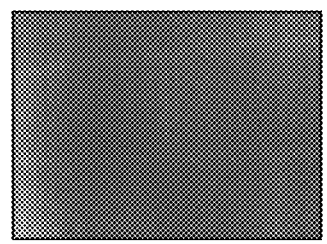
FIGS. 11A-11K illustrate the effect of distance between the subject and an IR detector on the temperature measurement without a distance correction.
Figure 11B:
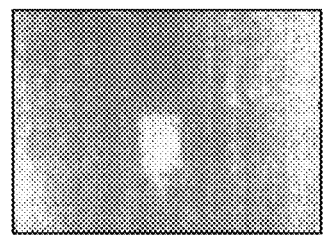
Figure 11C:
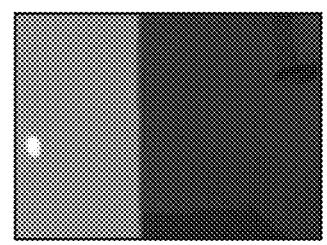
Figure 11D:
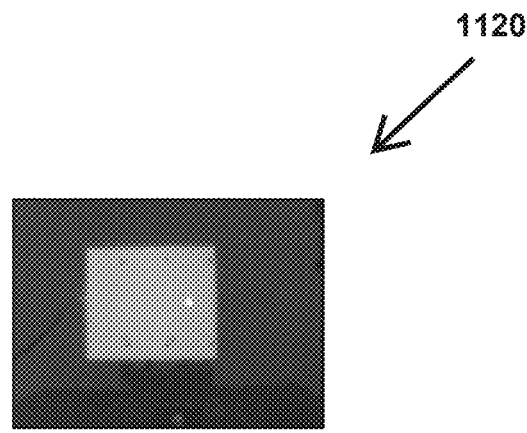
Figure 11E:
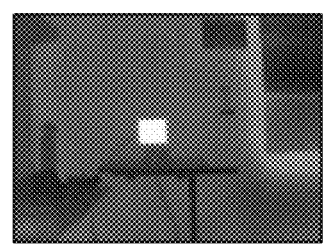
Figure 11F:
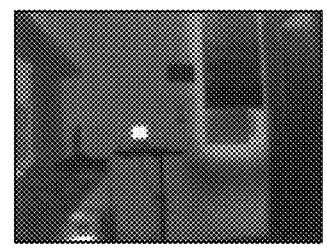
Figure 11G:
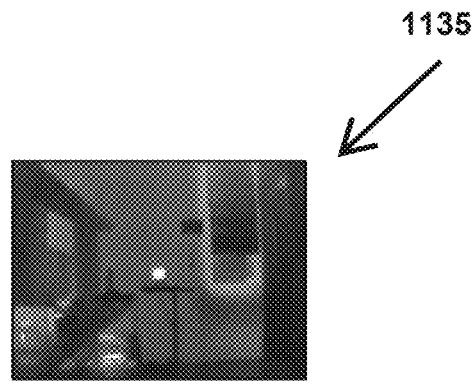
Figure 11H:
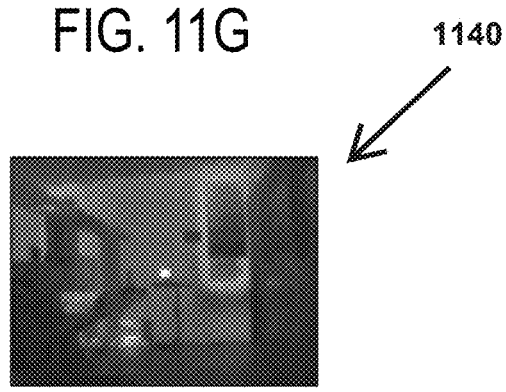
Figure 11I:
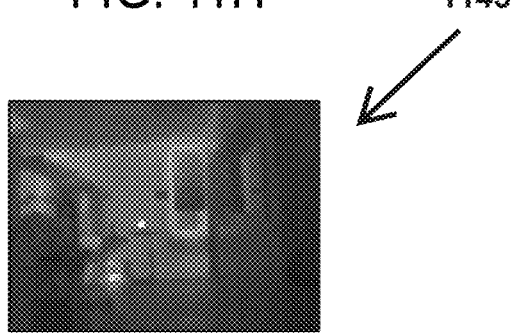
Figure 11J:
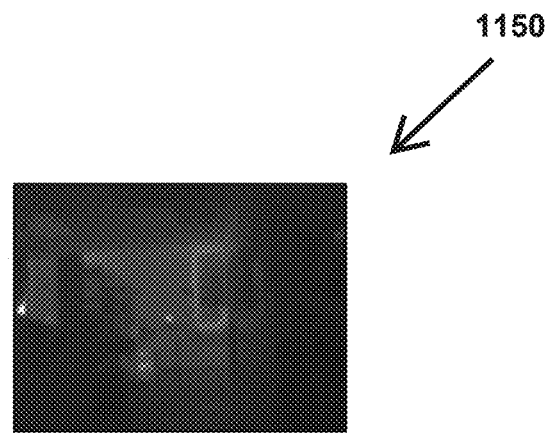
Figure 11K:
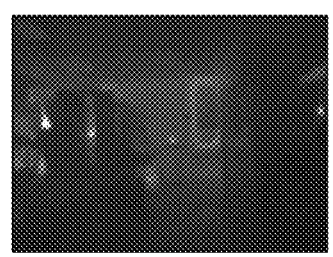
Figure 12:
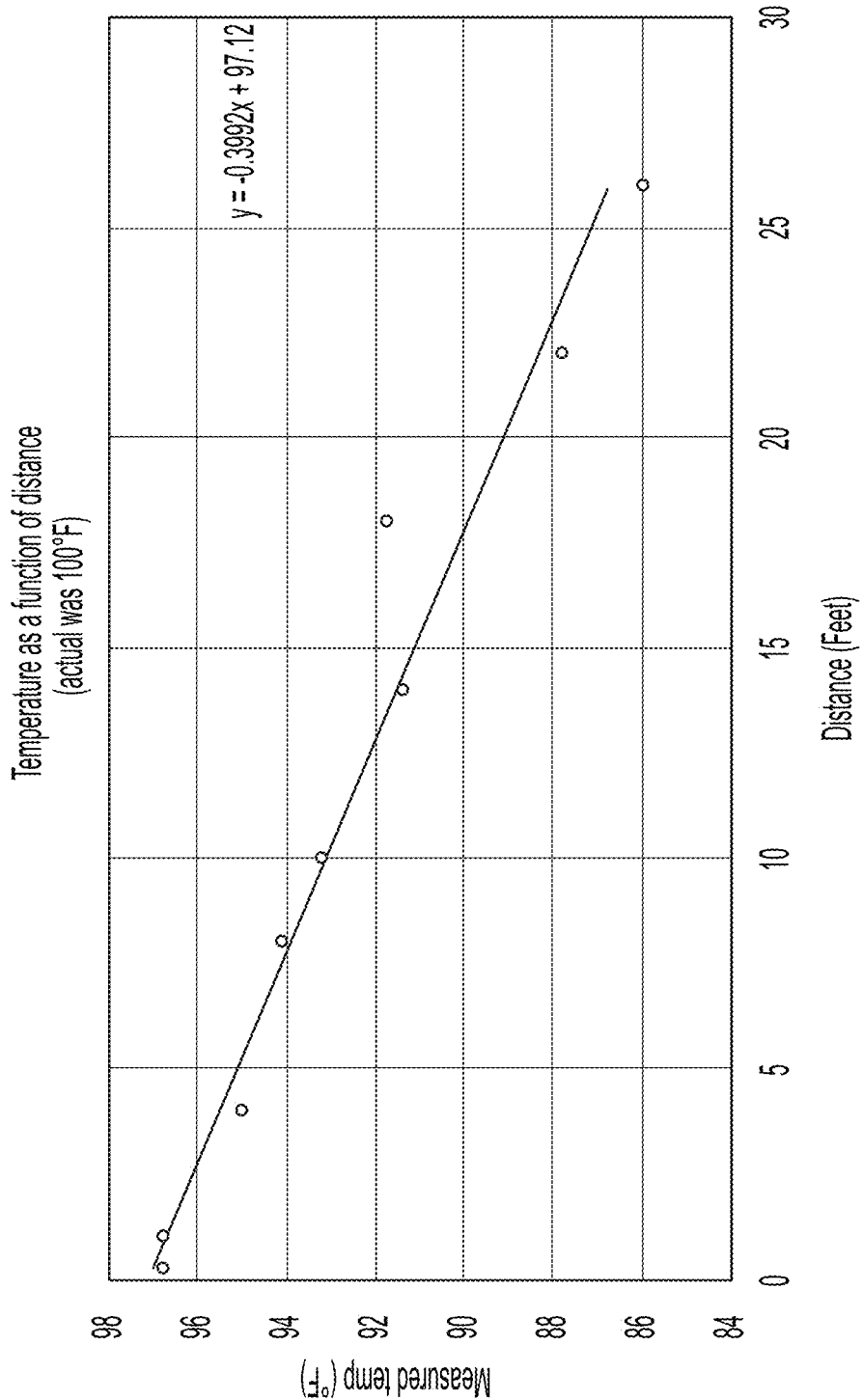
FIG. 12 includes a plot of the distance effect shown in FIGS. 11A-11K.

By way of example, FIGS. 11A-11K illustrate the impact of distance on the temperature measurements, and FIG. 12 shows the measured temperature as a function of distance. As shown in the figures, as the distance to the subject increases, the measured temperature decreases, resulting in a discrepancy between the nominal temperature measurement and the actual temperature of the subject.

More specifically, FIG. 11A shows an IRT image 1105 of a wall, FIG. 11B shows an IRT image 1110 of objects at a distance 0.25 ft., FIG. 11C shows another IRT image 1115 of objects at a distance 0.25 ft., FIG. 11D shows an IRT image 1120 of objects at a distance 1 ft., FIG. 11E shows an IRT image 1125 of objects at a distance 4 ft., FIG. 11F shows an IRT image 1130 of objects at a distance 8 ft., FIG. 11G shows an IRT image 1135 of objects at a distance 10 ft., FIG.

11H shows an IRT image 1140 of objects at a distance 14 ft., FIG. 11I shows an IRT image 1145 of objects at a distance 18 ft., FIG. 11J shows an IRT image 1150 of objects at a distance 22 ft., and FIG. 11K shows an IRT image 1155 of objects at a distance 26 ft.

For example, without any compensation for distance, an IRT device may measure a subject's temperature to be 36° C. at a distance of 0.25 and 30° C. at a distance of 26 ft., thus resulting in a temperature discrepancy of 6° C. Such a deviation is sufficient to render the IRT-based temperature measurements impractical for detecting human EBT conditions.

Figure 13:
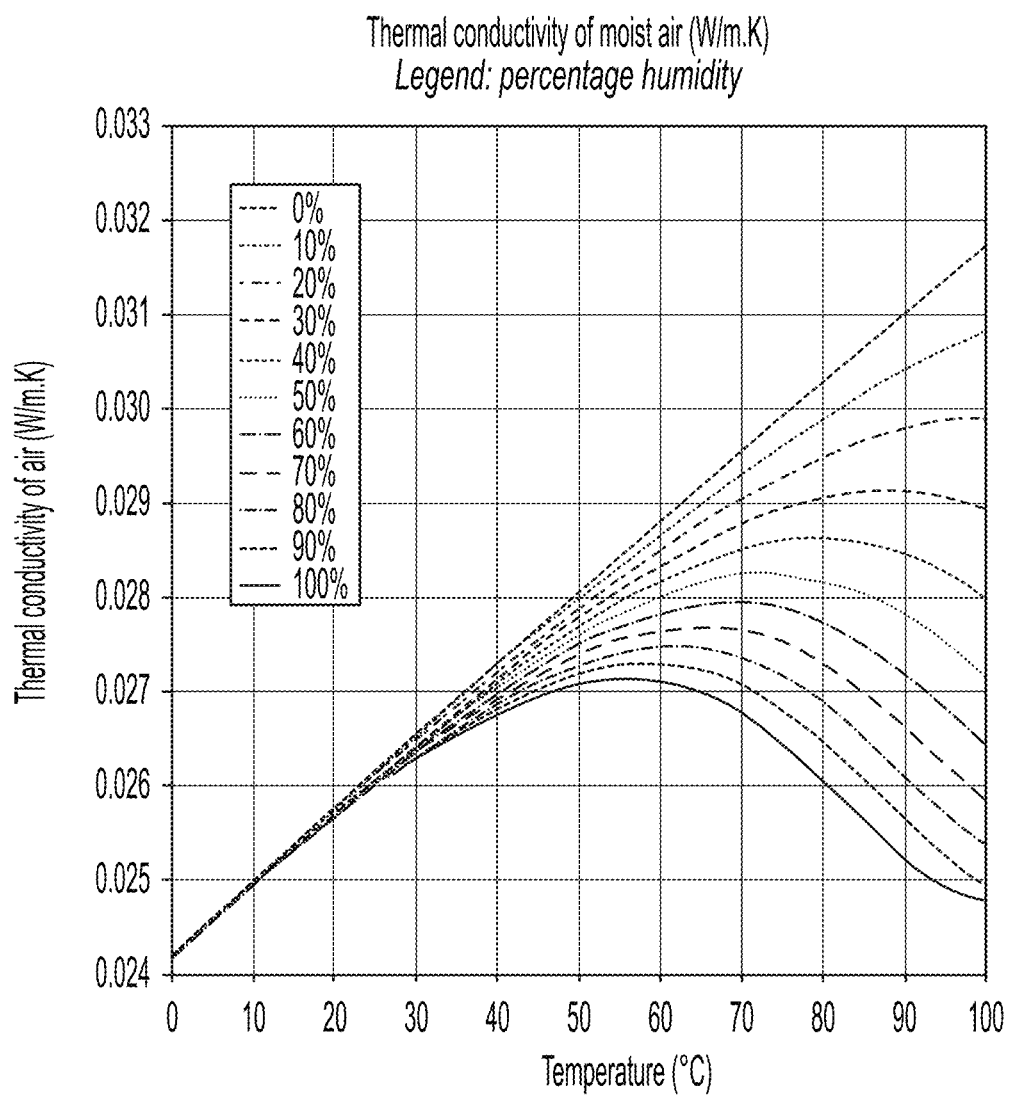
FIG. 13 illustrates the humidity dependency of the thermal conductivity of air with respect to temperature.

FIG. 13 shows the thermal conductivity of air, which affects the temperature measurements, as a function of temperature for various relative humidity values (from 0% to 100%). As indicated in FIG. 13, the change in the thermal conductivity of air as a function of humidity becomes more significant at higher air temperature and humidity. At 25° C., the humidity variation between 0% and 100% yields approximately 7% variation in the thermal conductivity.

As discussed above, an IRT imaging system according to the present teachings performs a distance correction based on ambient air thermal conductivity as well as the actual distance to the subject. To this end, in many embodiments, both the ambient air temperature and humidity are measured in-situ and utilized on an ongoing basis, and the nominal temperature measurements are corrected for the effect of thermal conductivity of the air. In some embodiments, the distance correction is performed by the processor executing AI-based algorithms. By way of example, the AI processor is "trained" with reference data sets of known objects (for example, people with different head and face coverings in different poses) with image data captured in mono and stereo configurations using different illumination conditions both polarized and unpolarized light to establish a ground truth (e.g., a training dataset). The AI-based feedback system is then used to construct the basis for correction via machine-learning of measured temperatures extended with mathematical models of known distances, known temperatures and humidity values, etc.

Figure 14:
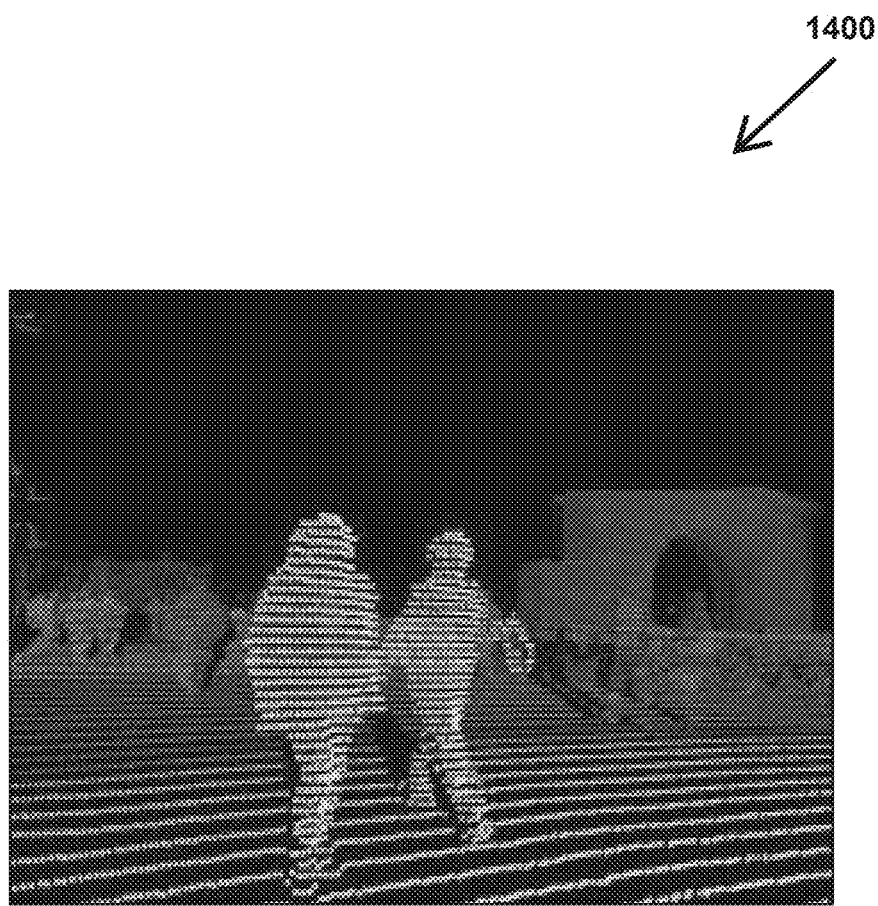
FIG. 14 shows an example of LIDAR distance measurement data.

In addition, as noted above, in many embodiments, an IRT imaging system according to the present teachings further includes a distance sensor to obtain a distance measurement between the subject and the detector. In some embodiments, the distance sensor may be implemented as a LIDAR sensor. However, the present disclosure is not limited thereto, and other types of distance sensors may also be used. The distance sensors that may be used include, and are not limited to, an ultrasound sensor, an IR sensor, a radar sensor, or the like. The LIDAR sensor may be a solid state device, and in conjunction with AI or machine learning technology, can obtain direct and accurate distance measurements to the subjects being monitored. LIDAR sensors provide improved accuracy in determining the distance. FIG. 14 illustrates an image 1400 as an example of distance data acquired with a LIDAR sensor as a black-and-white version of a typical color map (often referred to as a point cloud), which represents distance with cyan lines as the foreground, the black representing the sky at infinity and intermediate colors in between.

Figure 15:
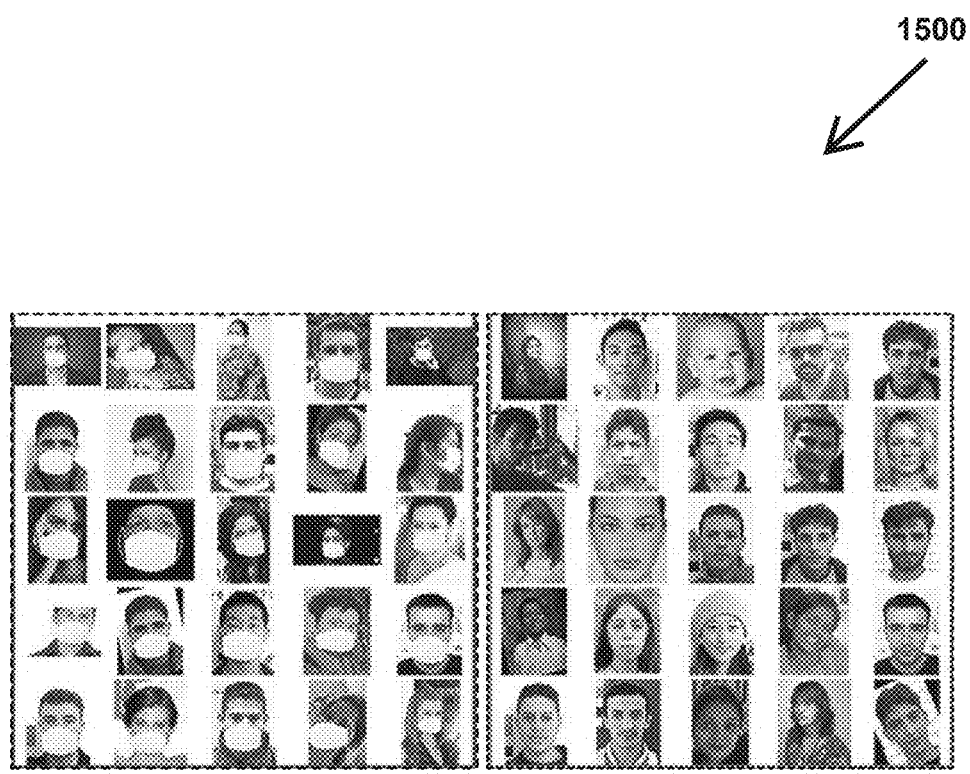
FIG. 15 shows an example where emissivity corrections are applicable.
Figure 16:
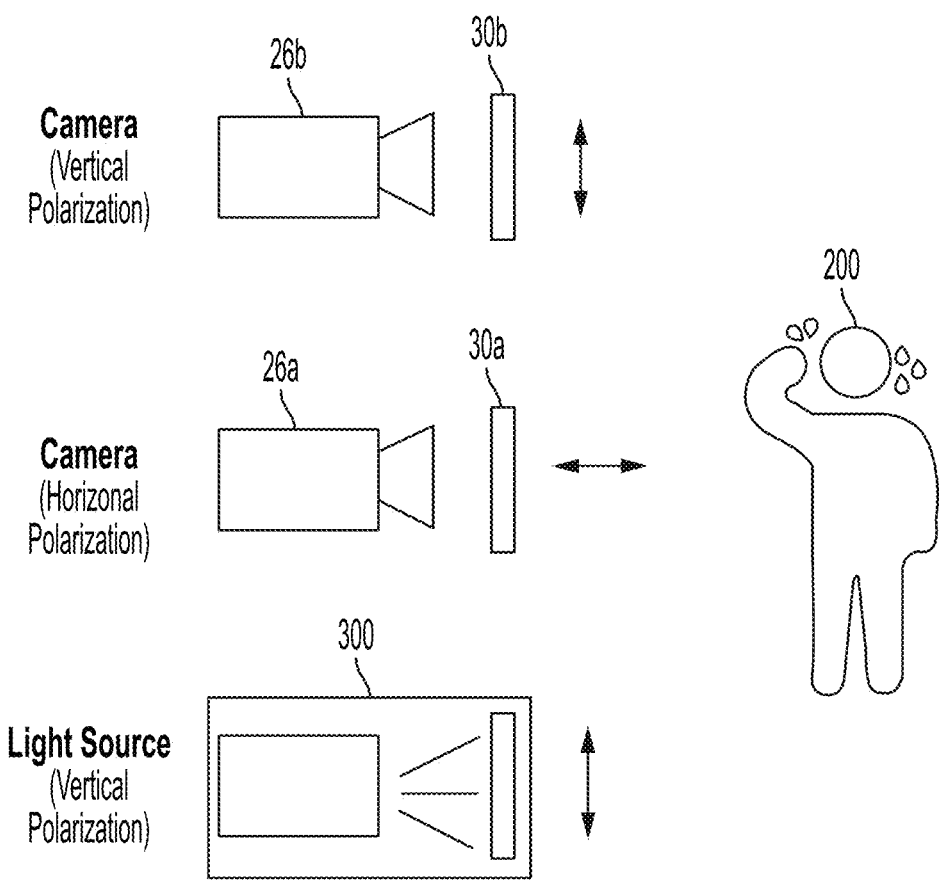
FIG. 16 schematically illustrates using dual stereo visible cameras with orthogonal polarizations and a polarized light source.
Figure 17:
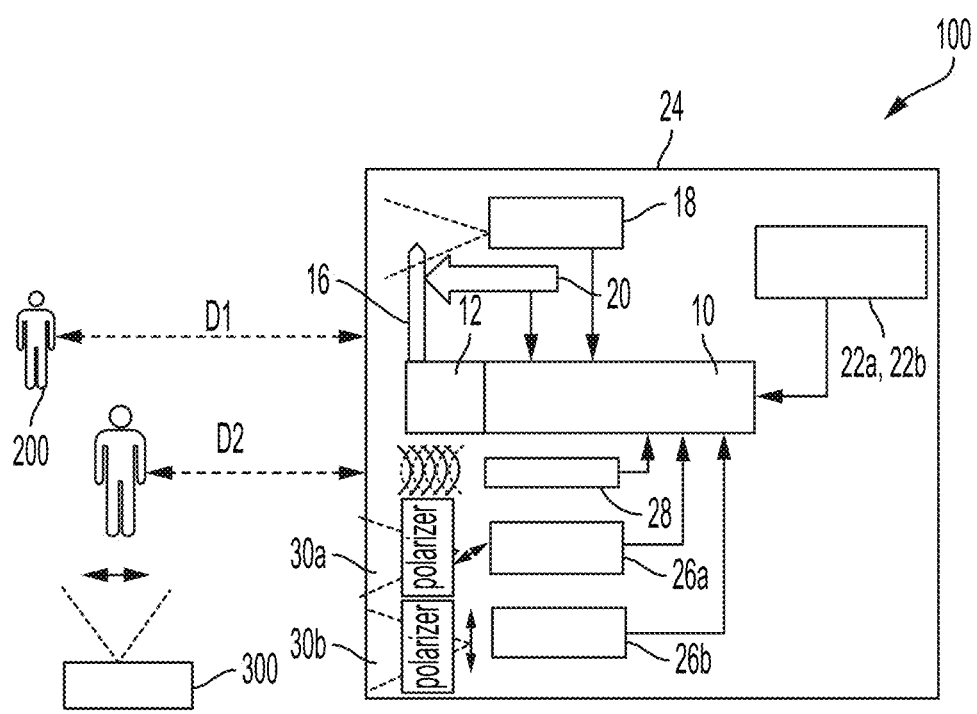
FIG. 17 schematically depicts an exemplary embodiment of an IRT imaging system according to the present teachings including dual stereo polarization imaging devices.
Figure 18:
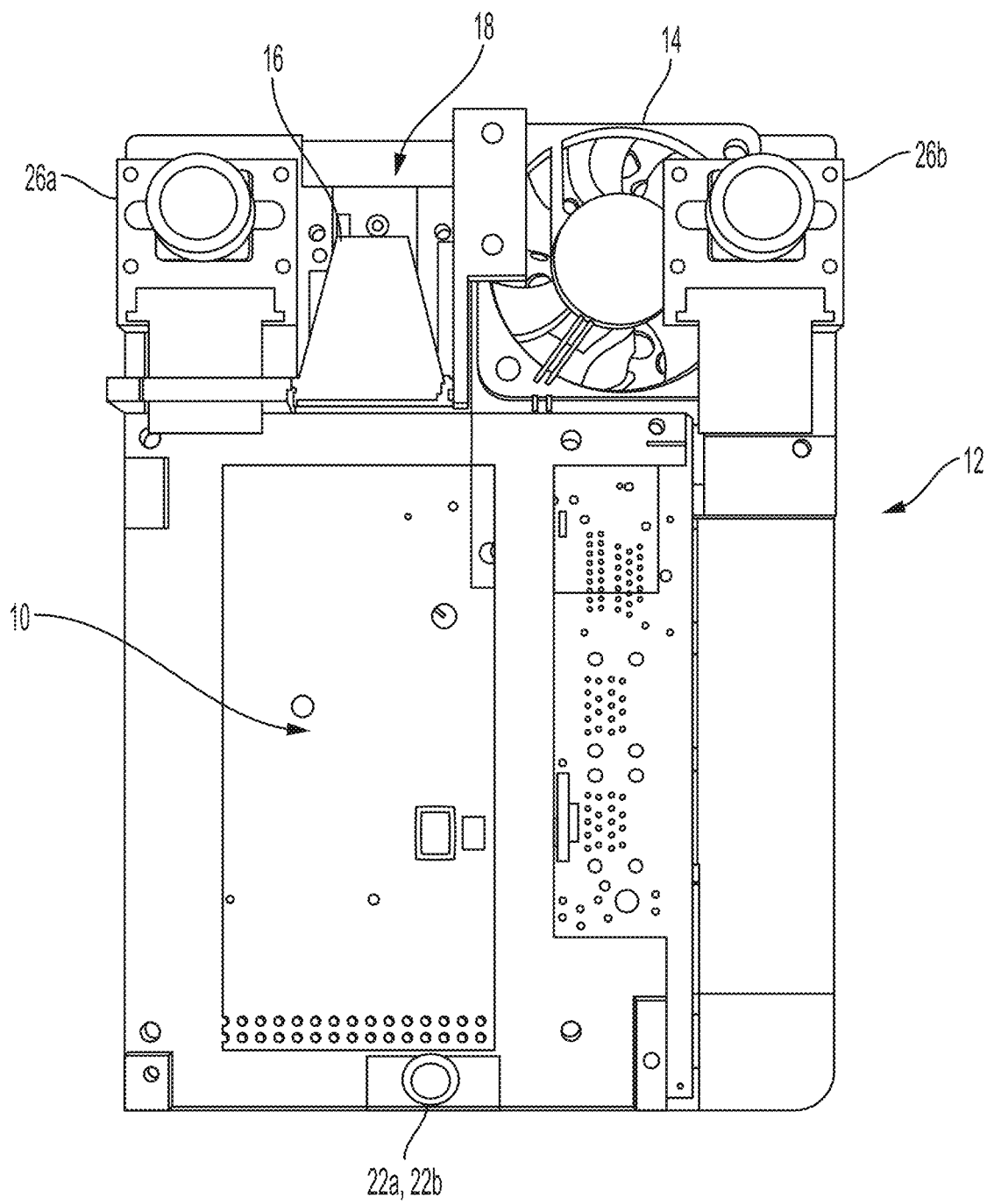
FIG. 18 shows a front view of the internal structure of an exemplary embodiment of an IRT imaging system according to the present teachings including dual stereo polarization imaging devices.
Figure 19:
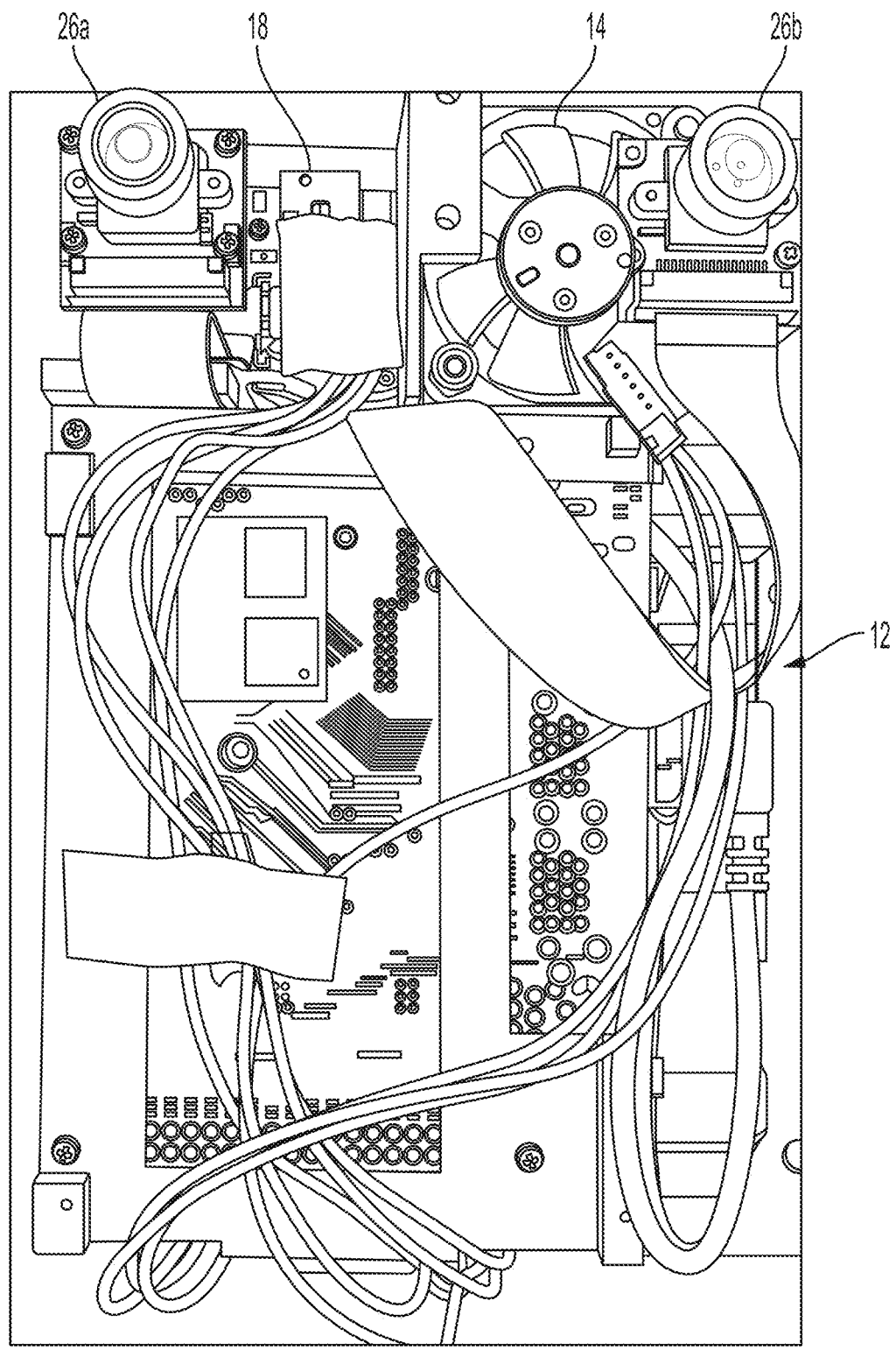
FIG. 19 shows a photograph of the internal structure of an embodiment of an IRT imaging system according to the present teachings.

In some embodiments, the temperature data from the IRT-based imaging device may be further corrected based on emissivity of the subject's surface emitting the infrared radiation. For example, as shown in FIG. 15 (including a panel 1500 of facial photos), a visible spectrum imaging device can detect a person's pose and/or face occlusions and provide information for correcting the temperature data from the IRT imaging device. By more effectively identifying occlusions such as face masks, eyeglasses, facial hair, and other coverings, the emissivity can be more accurately corrected, and thus a person's body temperature can be more accurately determined. Most prior art systems determine the temperature of a person by averaging all the pixels on a person's face (as detected by the visible camera AI algorithm) which can be inaccurate if the face is partly occluded. In some embodiments, the IRT systems according to the present teachings exclude occluded portions of the face (which will have different emissivity) and gives special weight to the pixels near the corner of the eyes (if available) which are typically the best location to estimate a person's internal body temperature on a face.

An emissivity exhibited by a subject can be affected by the subject's reflectivity. In some embodiments, to estimate/obtain more accurate emissivity, illumination conditions (incident angle of light), geometric properties of the space surrounding a subject, and age of the subject may be considered. A strong source of illumination (for example sunlight entering a window) reflecting from a subject can impact the temperature measurement. AI algorithms can detect the presence, type, and location of a strong illumination source through deep learning of shadow data sets. The age and sex of a subject are also determined using AI, typically inferred from the ground truth established during labeling of subjects. The reflectivity of a human face may vary due to, for example, perspiration, wearing make-up, or the like. If a person perspires due to various reasons such as having a fever, the IRT-based temperature measurement, without proper means for correction, may register a lower temperature than the actual temperature, due to a cooling effect and/or an emissivity-varying effect of perspiration. These data relating to the emissivity of the subjects may be analyzed by the AI processor and be used to compensate the nominal temperature measurements, e.g., by employing a scaling factor as a ratio of the measured emissivity and an assumed emissivity. This method uses the standard AI training approach with the ground truth established using direct temperature measurements of a large sample set using a thermometer.

In order to obtain an accurate estimate of emissivity associated with a subject, in some embodiments, an IRT imaging system may include dual stereo visible imaging devices 26a and 26b with orthogonal polarizations as shown in FIGS. 16-19. In some embodiments, the use of dual stereo visible imaging devices 26a and 26b may allow detection of water content, due to, for example, perspiration, and hence allow adjustment of the emissivity assigned to the subject to compensate for the effects of the water content.

Figure 20:
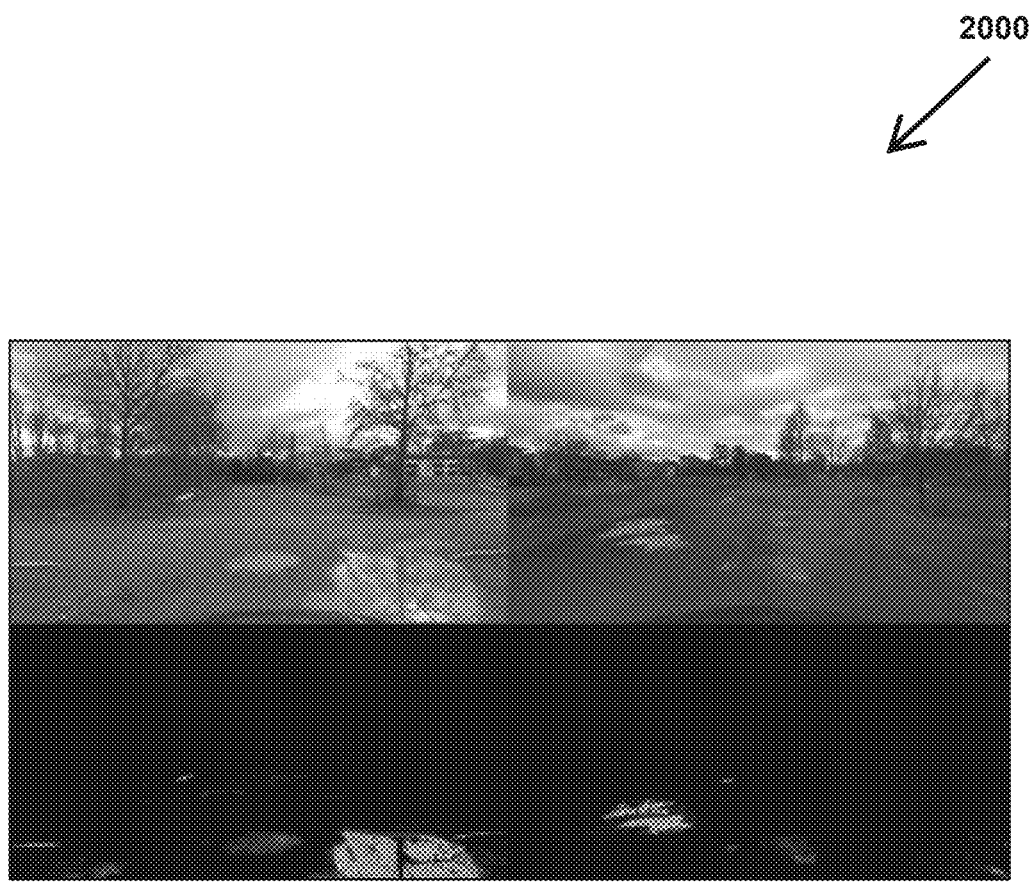
FIG. 20 shows an example of detecting water with dual stereo polarization imaging devices.

In some embodiments, each of the dual stereo visible imaging devices can include a polarizer 30a and 30b (e.g., a polarization filter) positioned in front thereof. By way of example, a first visible imaging device 26a can include a horizontal polarizer 30a, and a second visible imaging device 26b may include a vertical polarizer 30b. The vertical and horizontal directions are herein used in a relative manner, and polarizers with any two directions that are perpendicular to each other may be used. The use of polarized stereo imaging devices to detect water content has been described in references such as Nguyen et al. ("3D Tracking of Water Hazards with Polarized Stereo Cameras"), which is incorporated herein by reference in its entirety. FIG. 20 (including at panel 2000 of images) provides an example of detecting water with the dual stereo polarization technique. The Rayleigh sky model describes the observed polarization pattern of the daytime sky. When the sun is located at the zenith, the band of maximal polarization is near the horizon. Nguyen uses this example to show the strong effect of detecting water using a pair of polarized stereo cameras.

In some embodiments, the subject 200 may be illuminated with a polarized light source 300. The polarized light source 300 may be separately provided, or in some embodiments, it may be integrated into the IRT imaging system 100 within the housing 24.

Figure 21:
FIG. 21 shows images captured using dual stereo polarization imaging devices illuminated with a polarized light source.

FIG. 21 (including a panel 2100 of two photos) shows images captured using the dual stereo polarization imaging devices 26a and 26b. The left panel shows an image captured using the first visible imaging device 26a with the horizontal polarizer 30a, and the right panel shows an image captured using the second visible imaging device 26b with the vertical polarizer 30b, while being illuminated by the polarized light source 300. From the difference between the two images with the orthogonal polarization, more accurate emissivity can be estimated, thereby enhancing the accuracy of the temperature measurement with the system. The standard approach of using a large AI training dataset is used to establish the reflectivity ground truth.

Some embodiments provide a device that can capture one or more health related data or characteristics of one or multiple subjects at a distance. The health-related data or characteristics may include, for example, in addition to temperature and perspiration, measurements of the subject's heart rate, blood oxygenation, blood pressure, height, weight, age, and/or the gender.

Figure 24A:
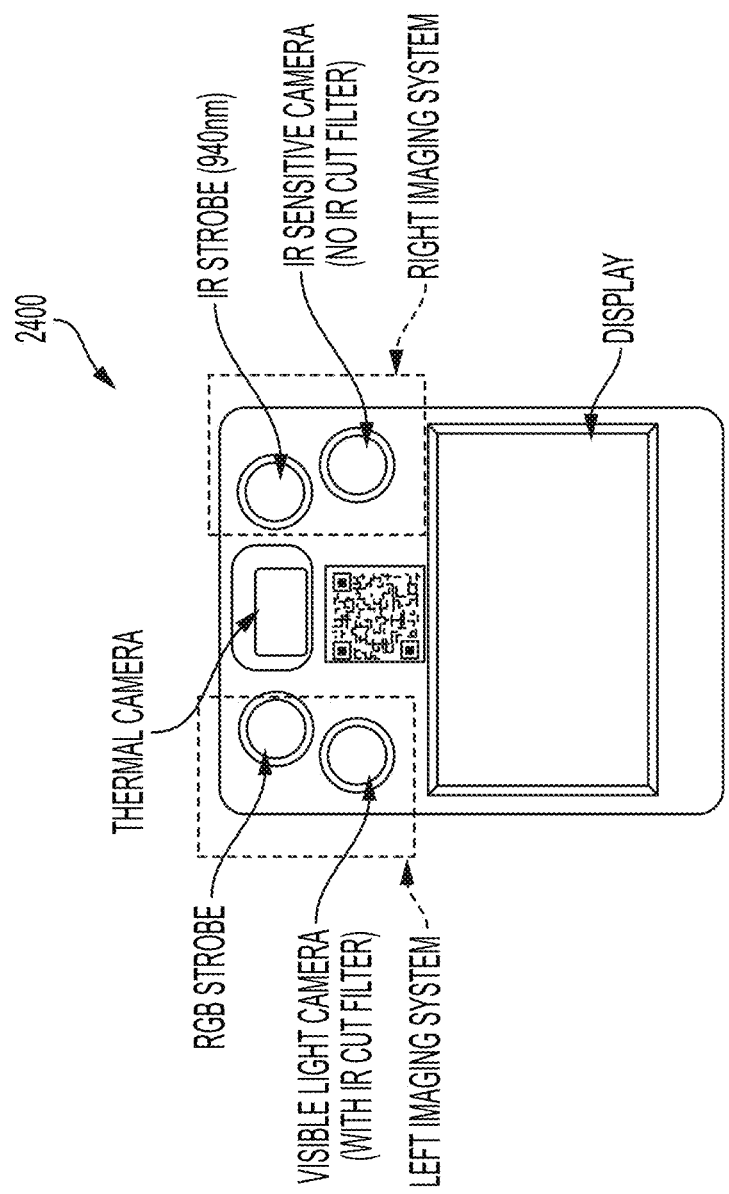
FIGS. 24A and 24B show a device that may perform one or more of the disclosed operations according to some embodiments.
Figure 24B:
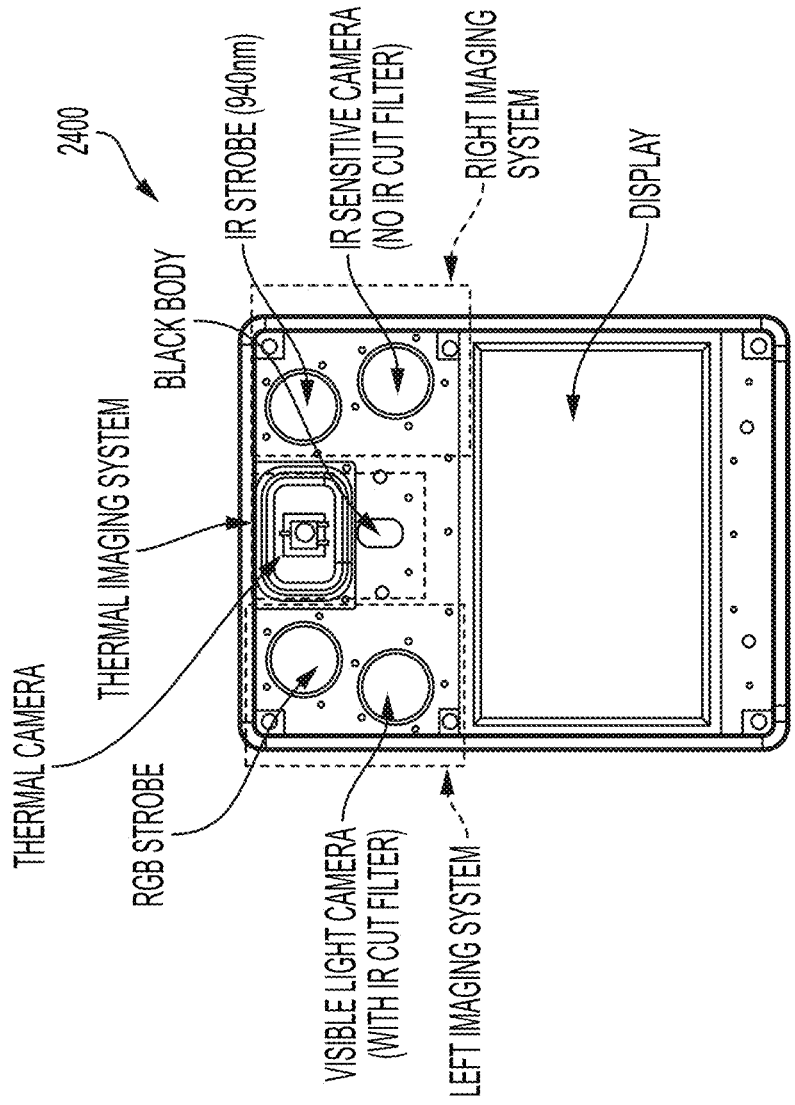

FIGS. 24A and 24B show a device 2400 that can perform one or more of the above operations according to some embodiments. In particular, FIG. 24A shows an external view of device 2400 and FIG. 24B shows a diagram of various parts of device 2400, listing four separate imaging systems. As shown in FIGS. 24A and 24B, device 2400 in addition to the thermal imaging system, includes a LEFT IMAGING SYSTEM, a RIGHT IMAGING SYSTEM, and a stereo vision system collectively. The device 2400 also includes a display in some embodiments.

The thermal imaging system includes a black body and a thermal imaging camera.

The LEFT IMAGING SYSTEM includes an RGB strobe vertical polarized light source (hereinafter also called white light or LEFT LIGHT) and a vertical polarized visible spectrum light camera (hereinafter also called LEFT CAMERA).

The RIGHT IMAGING SYSTEM includes an IR strobe light source (hereinafter also called IR light or RIGHT LIGHT) and an IR spectrum sensitive horizontal polarized camera (hereinafter also called IR camera or RIGHT CAMERA). In some embodiments, the IR strobe light emits light in a range around the 940 nanometer wavelength region of the spectrum.

The stereo vision system includes the combination of the LEFT CAMERA and the RIGHT CAMERA. Each of the four imaging systems may also include one or more modules that perform the required operations to derive the corresponding image and to display the image on the display. In some embodiments, the modules are included in the device in the form of a hardware, a software executed by one or more processors included in the device, or a combination of hardware and software as further described below in the conclusion section.

Figure 25:
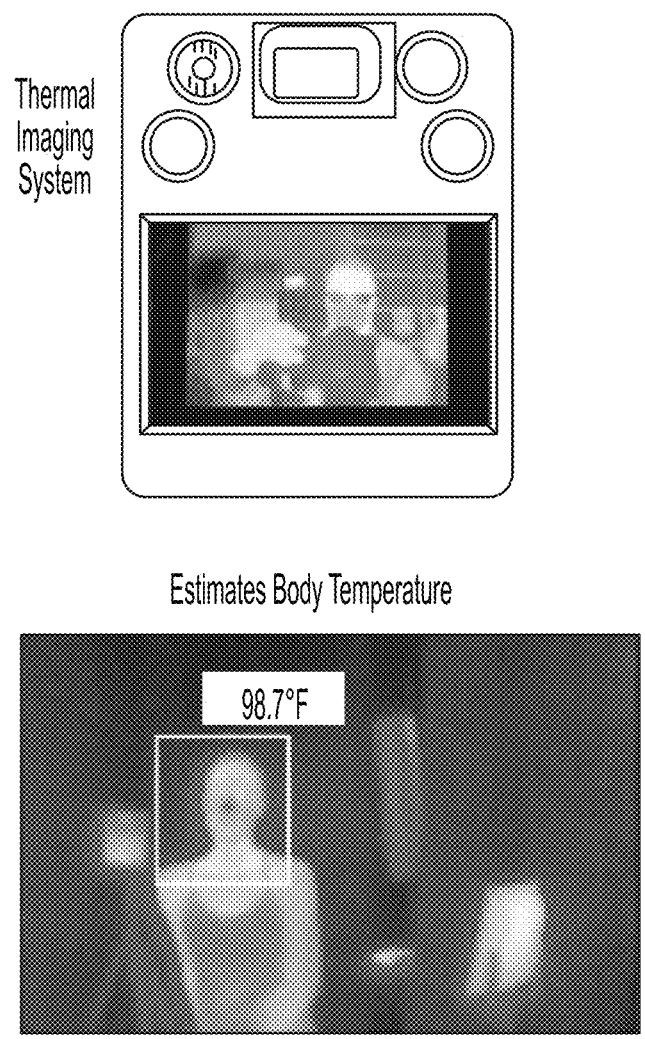
FIG. 25 illustrates the use of the thermal imaging system of the device for estimating the temperature of different parts of the body according to some embodiments.

FIG. 25 illustrates the use of the thermal imaging system of the device for estimating the temperature of different parts of the body according to some embodiments. The device may use mechanisms such as those explained above to estimate the temperature of various parts or extremities of the body of one or more subjects captured by the thermal camera. The body parts or extremities used for the temperature measurements may include, for example, the face, the arms, or some sections of the face such as a section of the forehead or corners of the eyes, or- one or more hands, etc. As depicted in FIG. 25, in some embodiments the device may show a thermal image of the captured scene which may indicate the temperature at the face or body extremities. Some embodiments utilize temperature variations between the extremities to estimate blood flow in a person's body to approximate the person's blood pressure. The correlation between skin temperature and blood flow rate has been established in numerous clinical studies.

Figure 26:
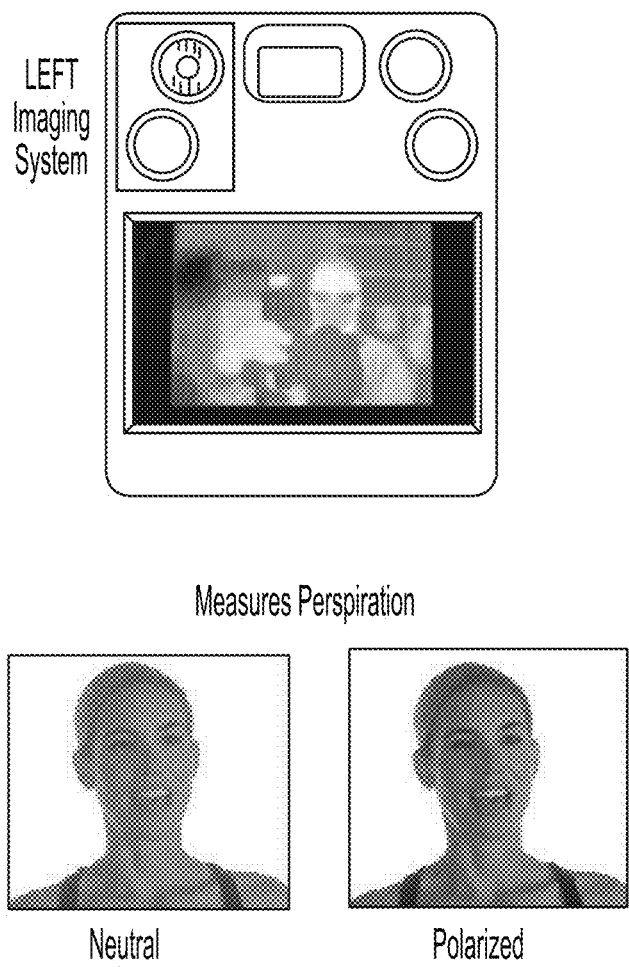
FIG. 26 illustrates the use of the LEFT IMAGING SYSTEM of the device for detecting the amount of skin moisture on one or more body parts of the subject according to some embodiments.

FIG. 26 illustrates the use of the LEFT IMAGING SYSTEM of the device for detecting the amount of skin moisture on one or more body parts of the subject according to some embodiments. The device may utilize mechanisms such as those explained above to detect perspiration on body extremities of the subject, such as the subject's face. For example, the device may utilize the RGB strobe polarized light source and the LEFT CAMERA in the LEFT IMAGING SYSTEM in combination with the RIGHT CAMERA in the RIGHT IMAGING SYSTEM for detecting skin moisture. In some embodiments, the polarization of the light emitted by the LEFT LIGHT, and the polarization of the filters used by the LEFT and RIGHT CAMERAS are selected in the manner described above to enable detection of the skin moisture.

FIGS. 27A-27D illustrate the use of the LEFT IMAGING SYSTEM or the RIGHT IMAGING SYSTEM to capture and classify different parts and different features of the human body, such as the face of the subject, according to some embodiments.

Figure 27A:
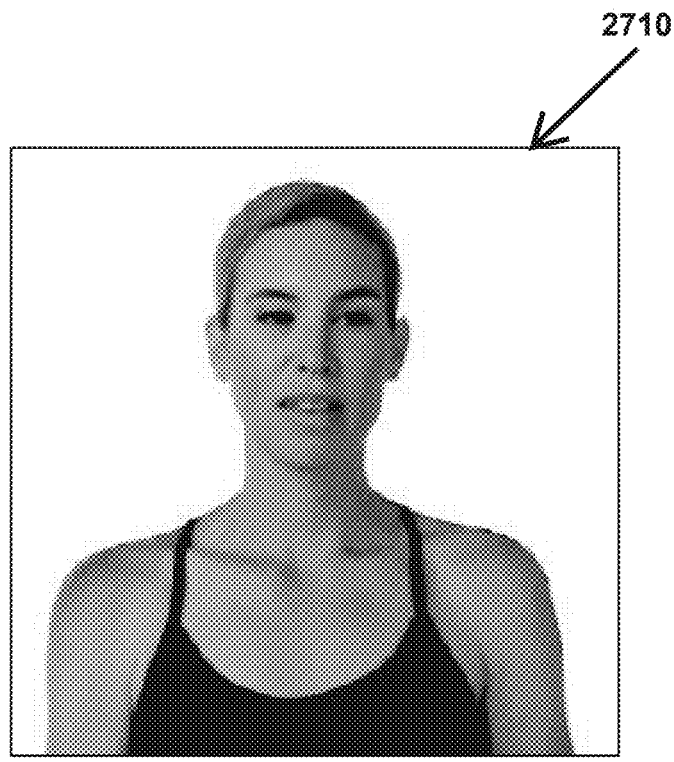
FIGS. 27A-27D illustrate the use of the LEFT IMAGING SYSTEM or the RIGHT IMAGING SYSTEM to capture and classify different parts and different features of the human body, such as the face of the subject, according to some embodiments.
Figure 27B:
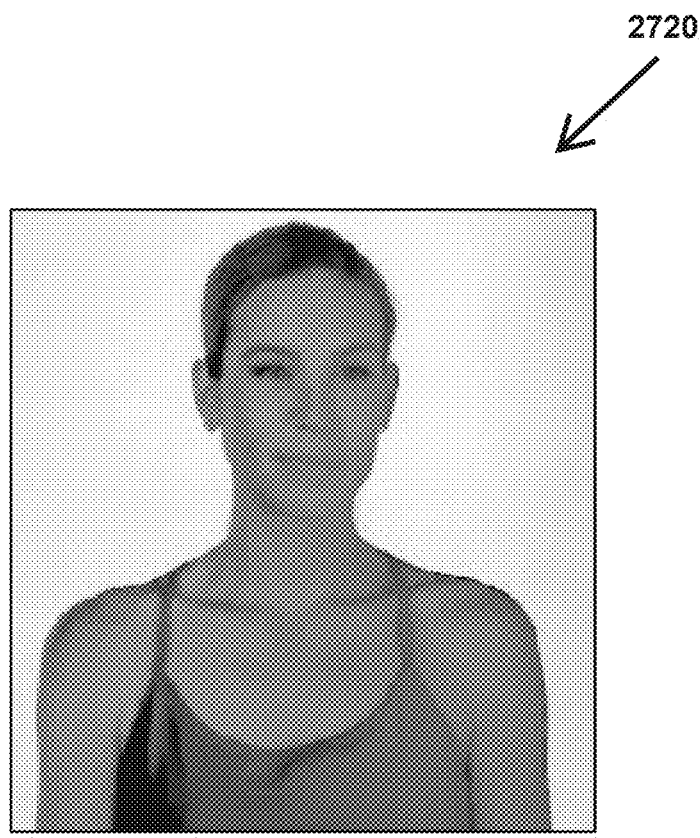

In particular, as shown in FIG. 27A (including an image 2710), the LEFT IMAGING SYSTEM may capture the image in the visible spectrum. FIG. 27B (including an image 2720), on the other hand, indicates that the IR spectrum of the RIGHT IMAGING SYSTEM may be used to do the same.

Figure 27C:
Figure 27D:
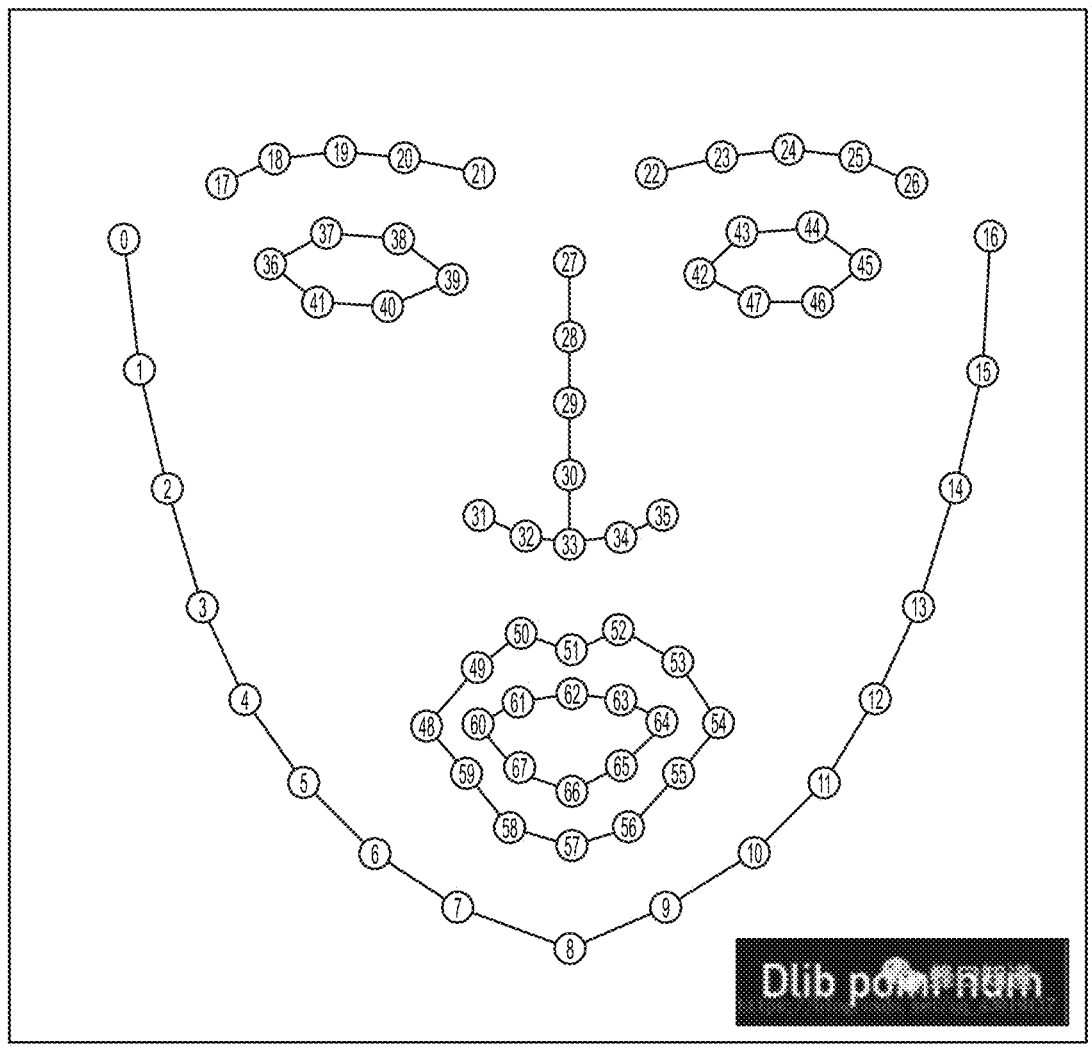

FIG. 27C (including an image 2730) shows that the device may utilize captured images to detect facial features or trained neural networks to estimate the age and/or the gender of a subject. The device may utilize one or more images captured by the LEFT IMAGING SYSTEM or the RIGHT IMAGING SYSTEM in addition to some other mechanisms to perform this function. For example, the device may use some face recognition mechanisms, such as those known in art and configured in accordance with the present teachings, to detect the face of the subject and some characteristics of that face, for example, the location of one or more reference points on the face, such as those shown in FIG. 27C. By way of example, FIG. 27D (including an image 2740) shows some reference points that may include one or more points located on the nose, eyes, eyebrows, cheeks, chin, or other parts of the face. Based on the location of the reference points or some other characteristics of the face, the device may use some artificial intelligence modules to estimate the age and the gender of the subject. The artificial intelligence modules may include one or more pre-trained neural networks.

Figure 28:
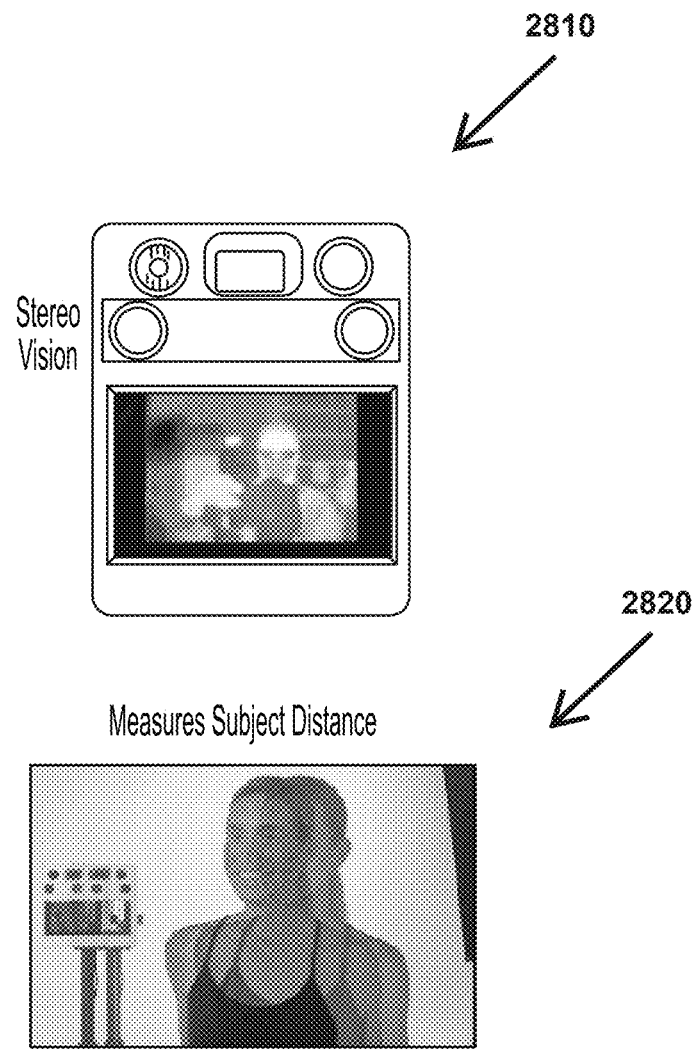
FIG. 28 illustrates the use of the stereo vision system to measure a distance between the device and a subject according to some embodiments.

FIG. 28 (illustrating a system 2810 and an image 2820) illustrates the use of the stereo vision system to measure a distance between the device and a subject according to some embodiments. In this operation, the device may triangulate the differences between the location of the face captured by the LEFT CAMERA and the RIGHT CAMERA to estimate the distance. The device may further utilize some algorithms based on calculations of the parallax or some artificial intelligence modules to estimate the distance. The device may utilize this mechanism in addition to or in place of other mechanisms, such as the one using the Lidar explained above.

Figure 29:
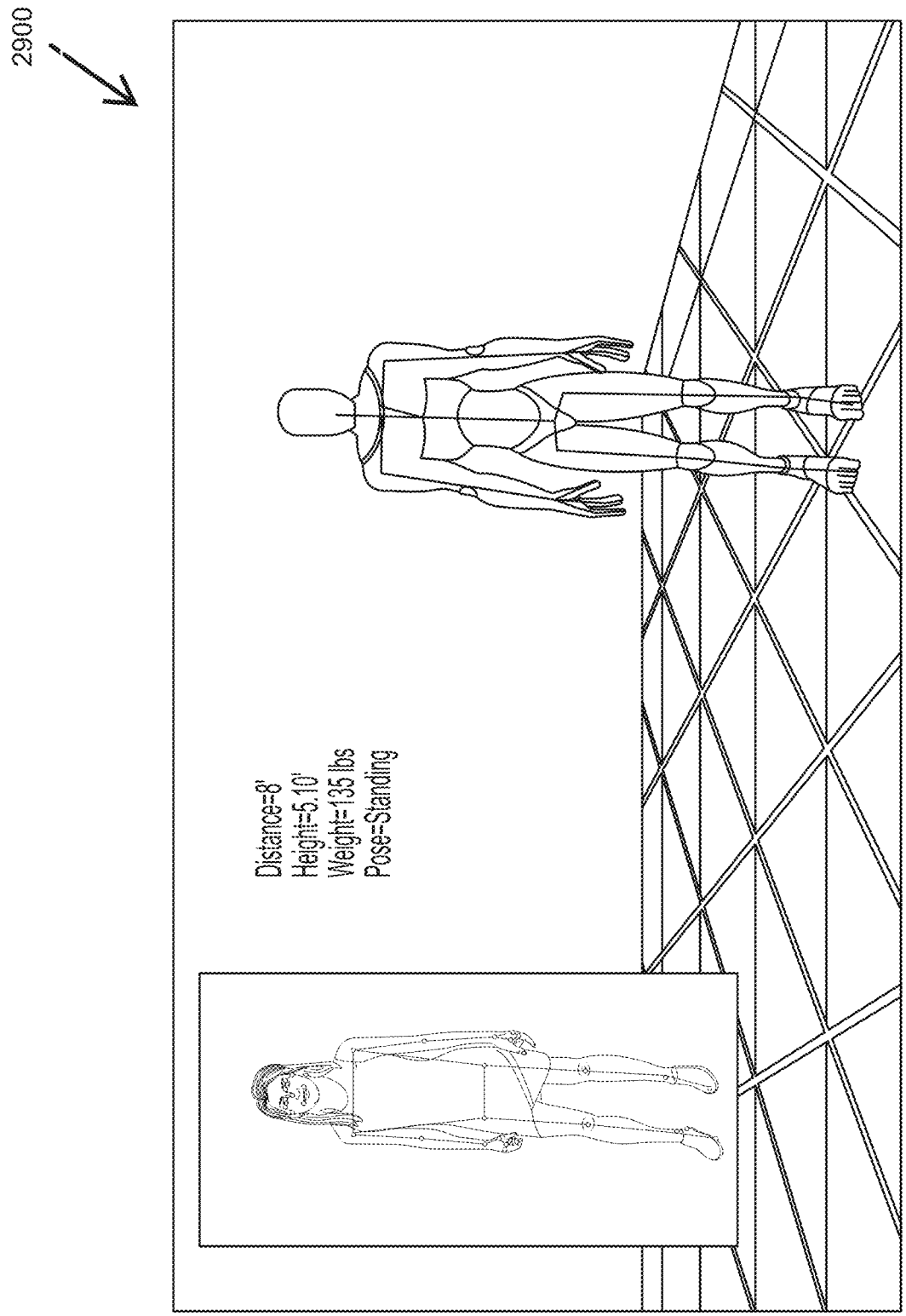
FIG. 29 illustrates the result of the operations by the device to further estimate some other characteristics such as the height, the weight, or features such as the pose of the subject, according to some embodiments.

FIG. 29 (including an image 2900) illustrates the result of the operations by the device to further estimate some other characteristics such as the height, the weight, or features such as the pose of the subject, according to some embodiments. The device may utilize some of the information derived from the captured images to locate different features on the body of the subject, such as tip of the head, or different points on the limbs of the subject. The device may further combine those locations with the estimated distance to the subject to estimate the height, width, or the pose of the subject and further to calculate the person's volume. The device may further utilize those estimates in addition to some other information derived from the image in combination with artificial intelligence to estimate the weight of the subject. For example, the weight of the subject may be estimated by approximating the body's density as the density of water and multiplying that by the estimated volume. Alternatively, the device may use trained models to estimate a person's weight.

Figure 30A:
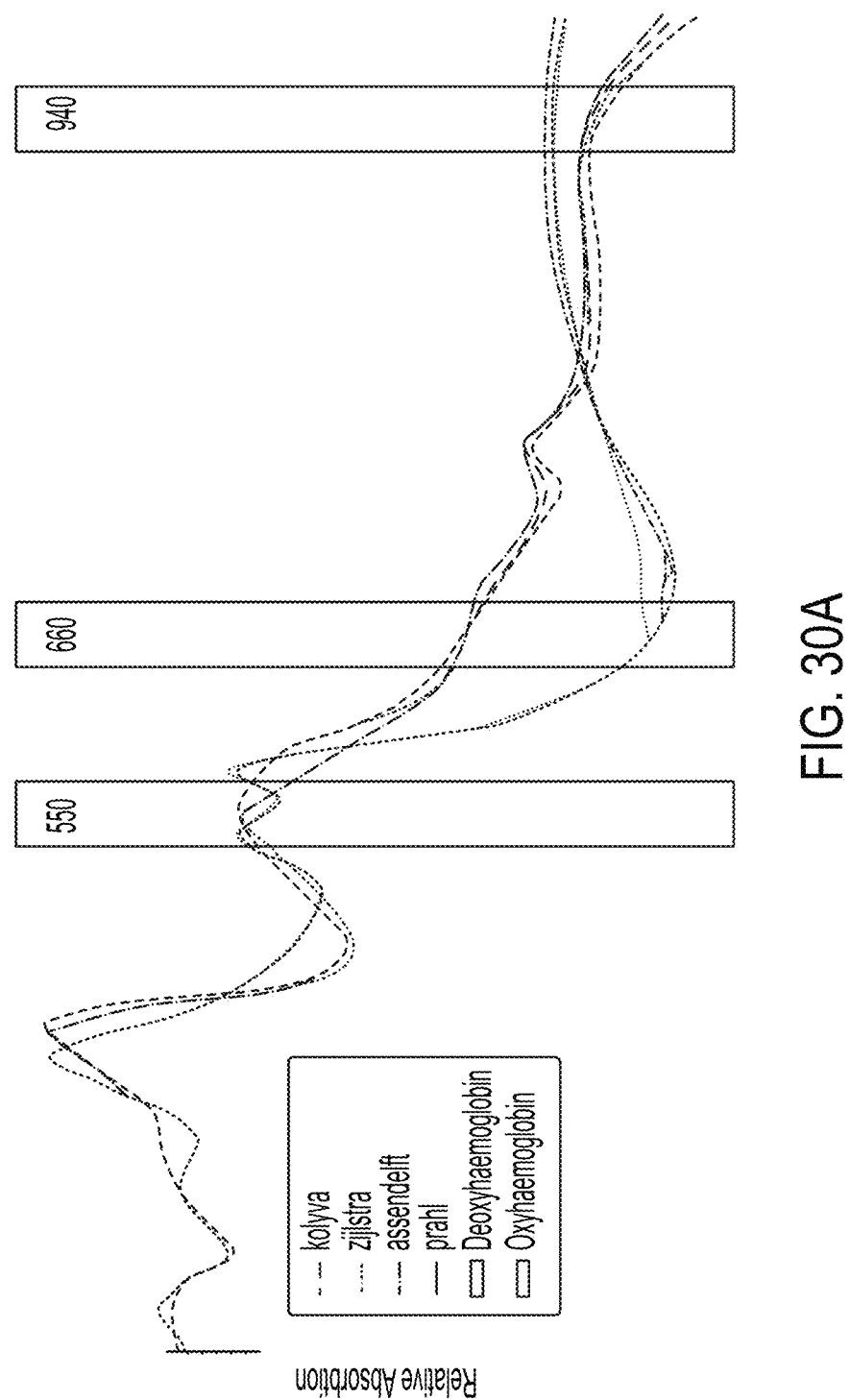
FIGS. 30A and 30B illustrate some the characteristics of human blood when interacting with the light spectrum, as utilized in some embodiments.
Figure 30B:
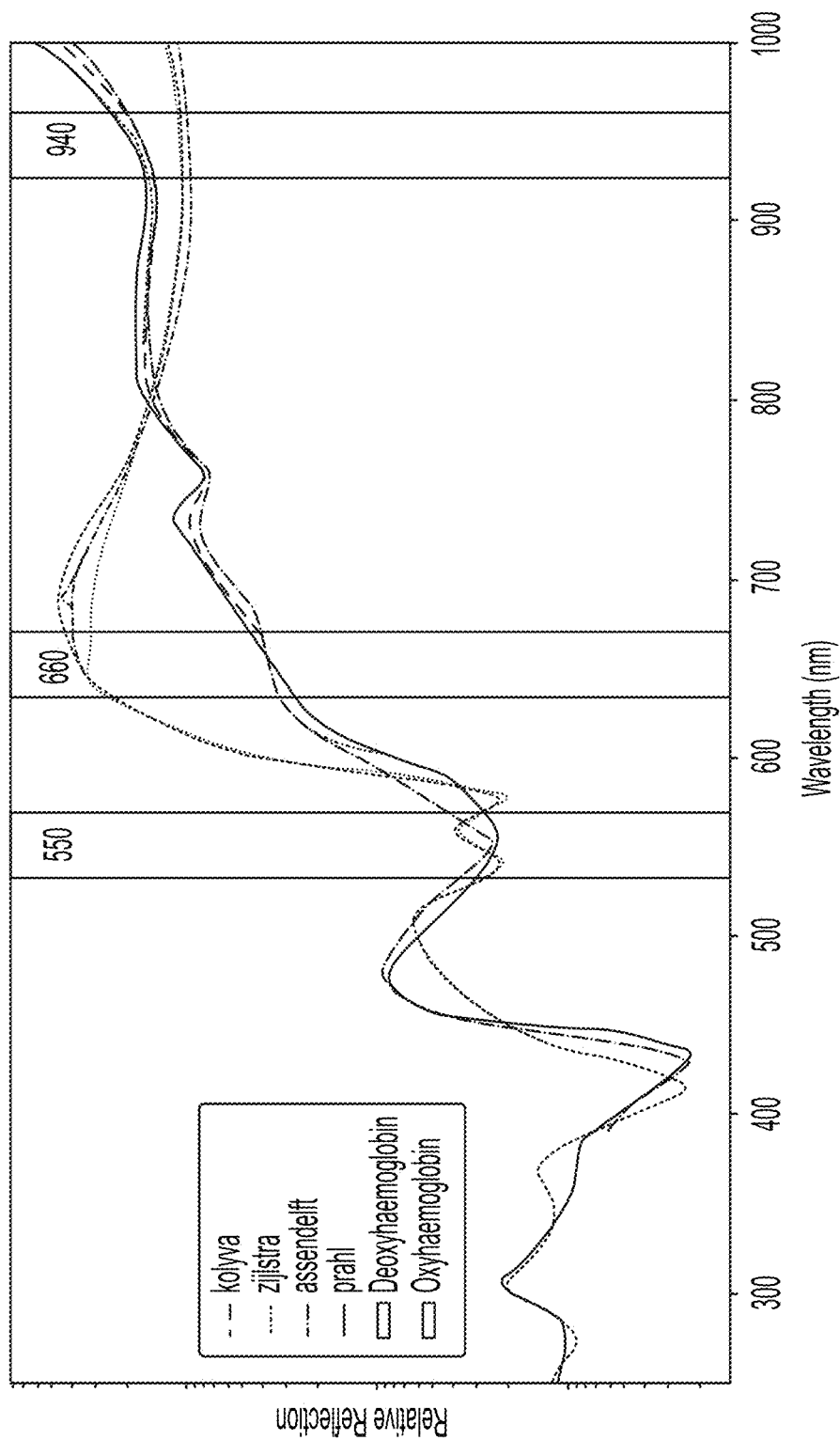

FIGS. 30A and 30B illustrate some characteristics of human blood when interacting with the light spectrum, as utilized in some embodiments. In particular, FIG. 30A qualitatively shows the absorbance of different wavelengths of electromagnetic radiation by the oxygenated hemoglobin and by the deoxygenated hemoglobin. Similarly, FIG. 30B qualitatively shows the reflectance of different wavelengths of that electromagnetic radiation by oxygenated hemoglobin and by deoxygenated hemoglobin. The graphs in the two figures are complimentary in the manner that changes in absorbance are essentially the mirror of the changes in reflectance. The graphs show that the human blood, whether oxygenated or deoxygenated, shows a high absorbance around 550 nanometer, which corresponds to a green color (hereinafter referred to as the green wavelength). On the other hand, the oxygenated hemoglobin shows much higher reflectance compared to the deoxygenated hemoglobin around 660 nanometers, corresponding to a red color (hereinafter referred to as the red wavelengths), but a lower reflectance around 940 nanometers (near infrared, referred to as NIR or IR in this disclosure).

In some embodiments, a device according to the present teachings utilizes a measurement of the absorbance and reflectance characteristics of the human blood, and the differences between the oxygenated and deoxygenated hemoglobin to measure a variety of biomarkers, for example blood oxygenation efficiency, heart rate and breathing rate. In various embodiments, the device may use data captured through the LEFT IMAGING SYSTEM and/or RIGHT IMAGING SYSTEM.

Figure 31:
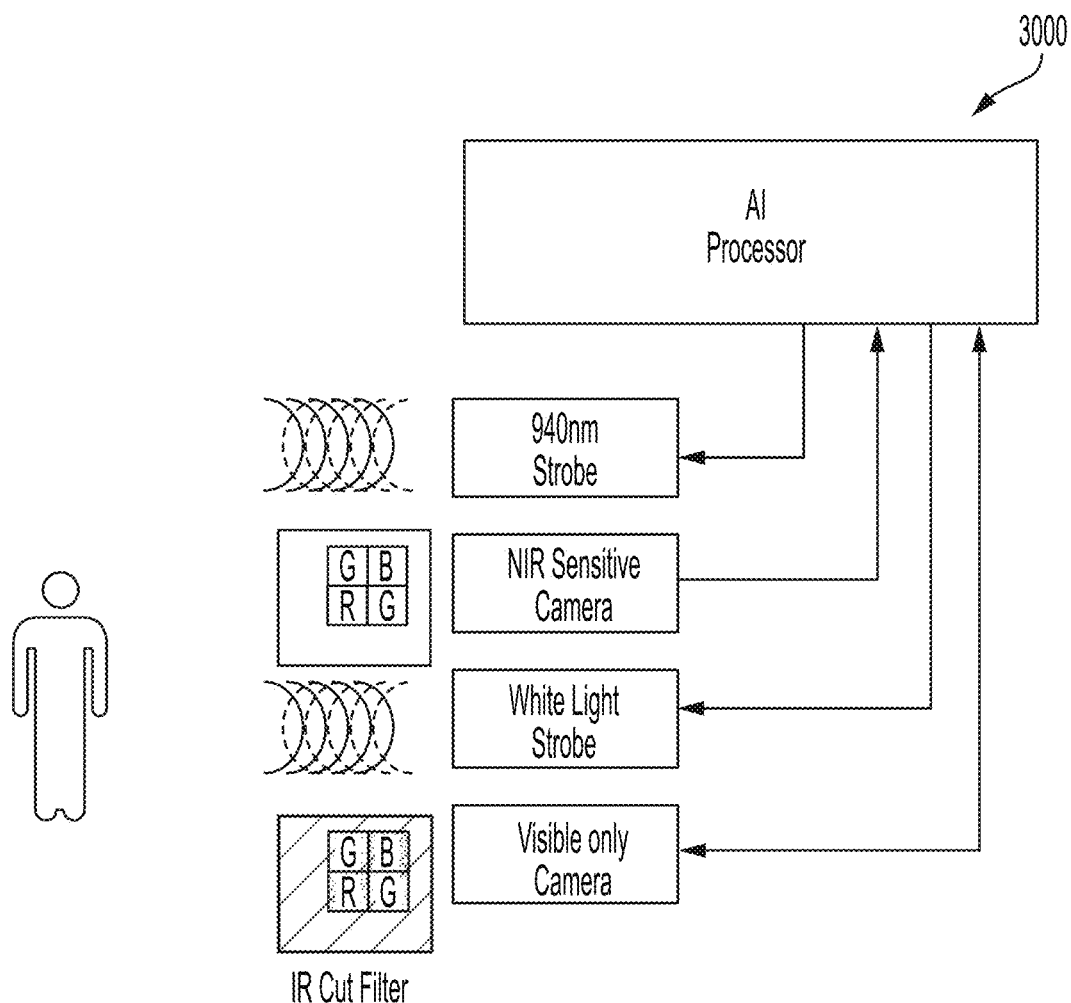
FIG. 31 illustrates an example system utilized by the device to measure the heartbeat rate or the peripheral oxygen saturation (SpO2) of a subject according to some embodiments.

FIG. 31 illustrates an example system 3000 utilized by the device to measure the heartbeat rate or the peripheral oxygen saturation (SpO2) of a subject according to some embodiments. System 3000 may include an artificial intelligence module or processor, an IR imaging system, and a white light imaging system. The IR imaging system may include an IR strobe light (such as the RIGHT LIGHT) emitting light at an IR wavelength and an NIR sensitive camera (such as the RIGHT CAMERA) for example using a CMOS sensor without an IR cut filter; and the white light imaging system may include a white light strobe (such as the LEFT LIGHT) and a visible light only camera (such as the LEFT CAMERA) for example using a CMOS sensor with an IR cut filter. In some embodiments, system 3000 is used to measure the SpO2 and the heart rate through a combination of lighting and sampling as further explained below.

In some embodiments, the device may include different types of light filters for its various cameras with different sensitivities to different parts of the electromagnetic spectrum to optimize its response. For example, a typical color CMOS sensor may contain a layer of RGB filters overlaying the light sensitive pixels, called the Bayer filter. Moreover, the Blue filter may have a peak response at about 450 nm (BLUE CHANNEL); the Green filter may have a peak response at about 550 nm (GREEN CHANNEL); and the Red filter may have a peak response at about 650 nm (RED CHANNEL). Normal cameras include a second (IR Cut) filter acting as a visible light bandpass filter overlaying the CMOS sensor. The IRC filter eliminates spectral response at wavelengths higher than 700 nm and often and wavelengths lower than 400 nm. The IRC filter helps produce natural colors for images presented to humans and also improves image sharpness by limiting optical aberrations associated with a wider spectrum of optical response.

Some embodiments instead utilize two cameras one with an IRC filter (e.g. LEFT CAMERA) and one without the IRC filter (e.g. RIGHT CAMERA) to simultaneously sample selected and complimentary parts of the electromagnetic spectrum.

Figure 32A:
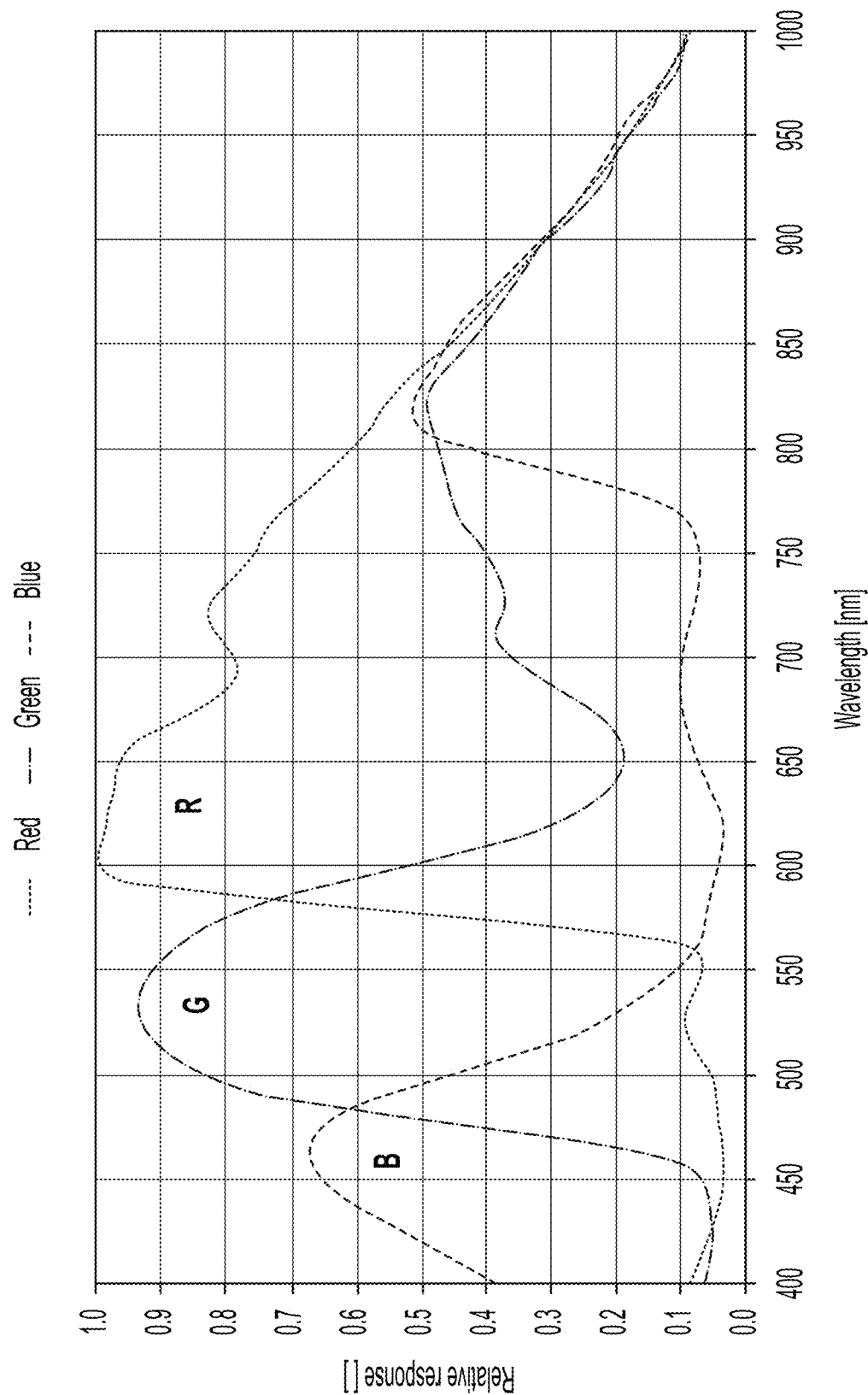
FIGS. 32A-32B show responses of RIGHT and LEFT CAMERAs to electromagnetic wavelengths according to some embodiments.
Figure 32B:
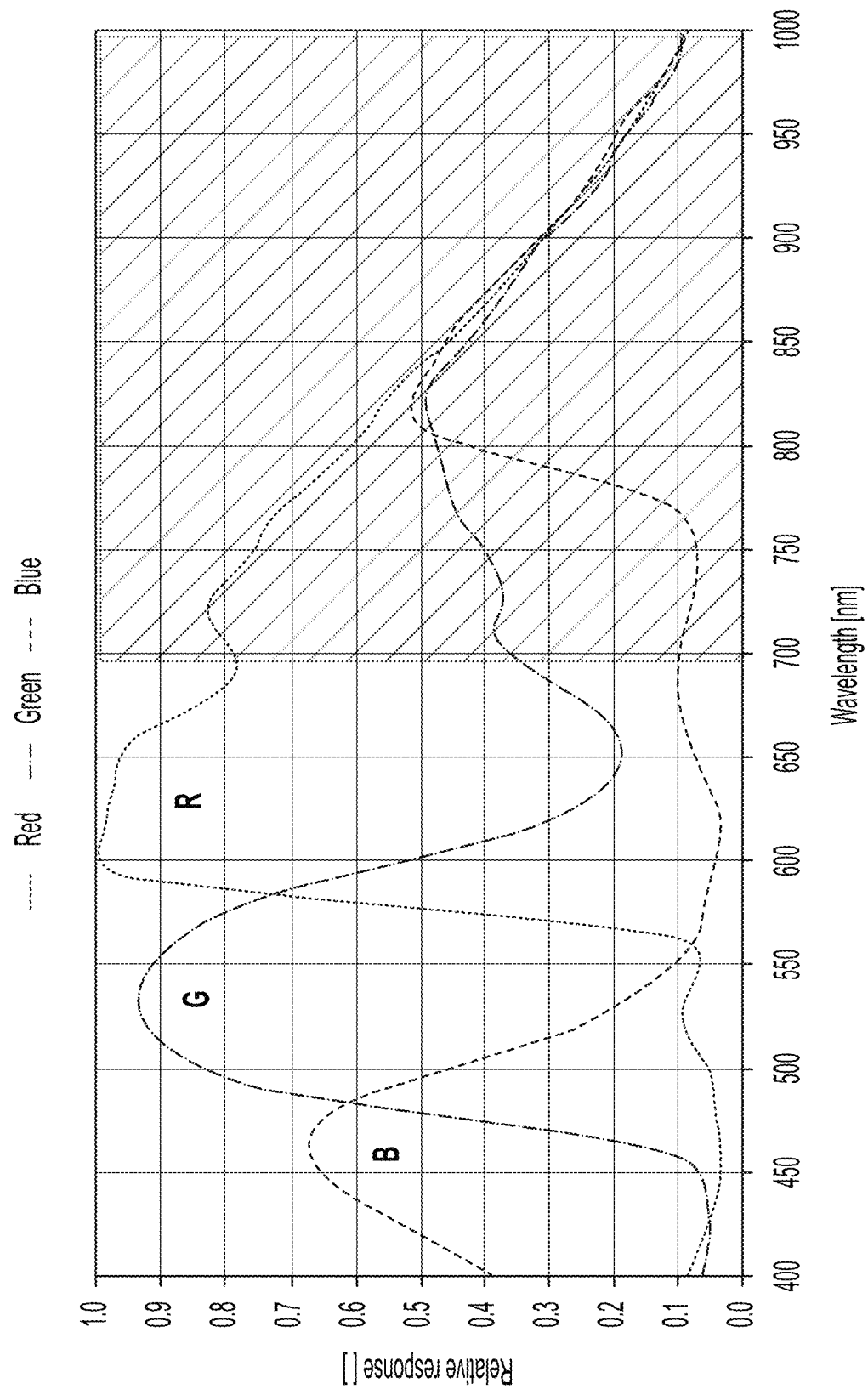

FIGS. 32A-32B show responses of RIGHT and LEFT CAMERAs to electromagnetic wavelengths. In particular FIG. 32A shows the response of the RIGHT CAMERA, with no IRC filter, to a range of wavelengths of the electromagnetic spectrum, a sample image of which is shown in FIG. 27B. As FIG. 32A shows, in such a camera, the three channels for red (R), green (G), and blue (B) detect three different regions of the spectrum respectively peaked at the red, green, and blue wavelengths while their response around the near IR wavelength of 940 nanometers overlap.

FIG. 32B, on the other hand, shows the response of the LEFT CAMERA, which uses an IRC filter, to a range of wavelengths of the spectrum, a sample image of which is shown in FIG. 27B. FIG. 32B shows that such a camera detects the wavelengths that are within the visible spectrum in a manner similar to the RIGHT CAMERA, but it eliminates (attenuates) response in the IR section of the spectrum, for example, wavelengths above 700 nanometers (thus shaded out).

In some embodiments, the device measures biometric parameters such as the SpO2 or heartbeat rate by collecting and analyzing absorption/reflectance of one or more sections of the subject's skin with respect to different parts of the spectrum. For collecting data in a specific section of the spectrum, the device may selectively choose an appropriate color detection channel (Bayer filter) from among the R, G, and B channels, as further detailed below.

FIGS. 33A-33D illustrate different mechanisms that the device may use for collecting data in three different sections of the spectrum, around the green, red, and IR wavelengths, discussed above in relation to FIGS. 30A and 30B. As explained there, these wavelengths are significant for the changes in the absorbance or reflectance properties that blood, or the oxygenated and deoxygenated hemoglobin, display at these wavelengths.

Figure 33A:
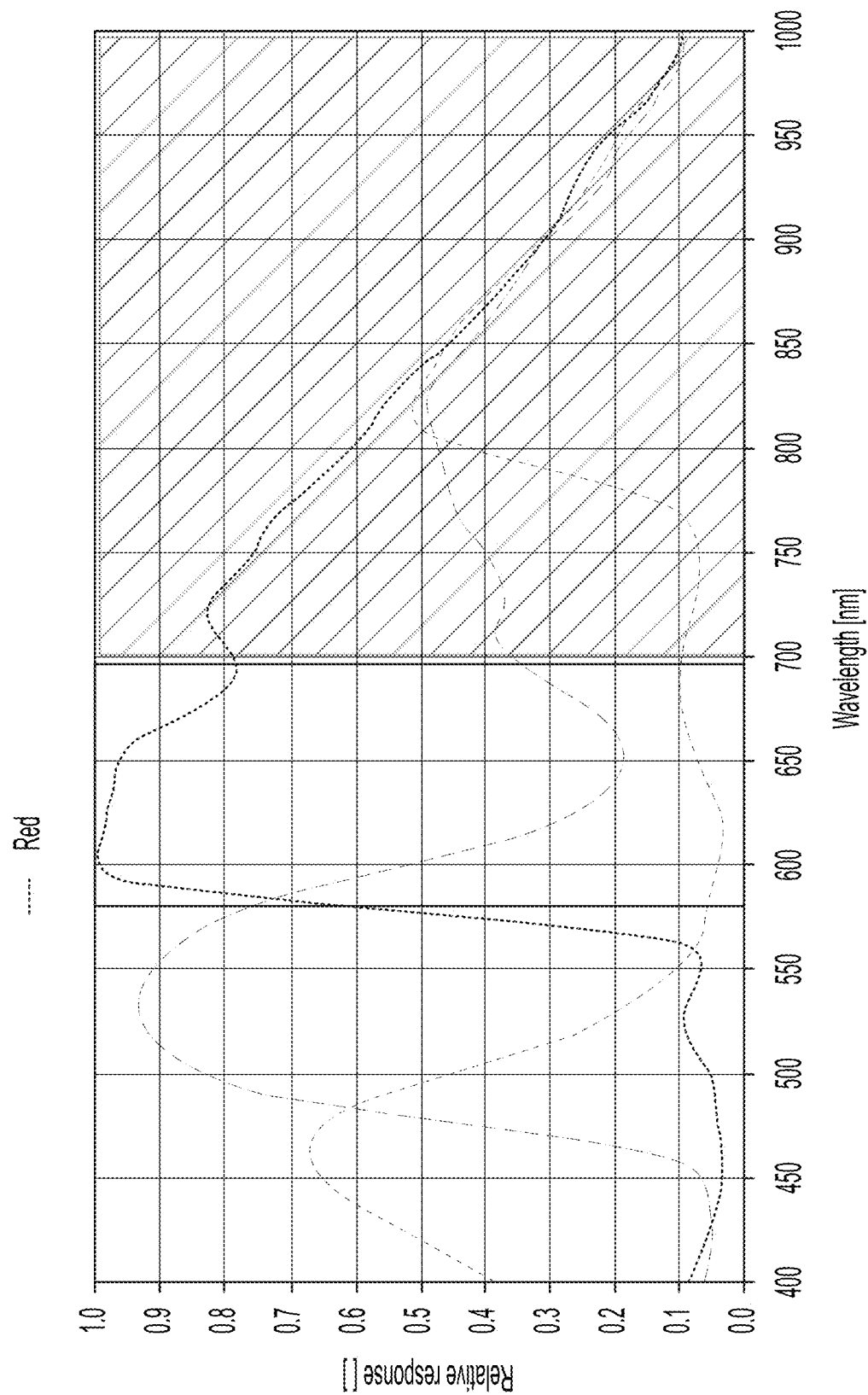
FIGS. 33A-33D illustrate different mechanisms that the device may use for collecting data in three different sections of the spectrum, around the green, red, and IR wavelengths, according to some embodiments.

FIG. 33A, for example, shows the sensitivity of the RED CHANNEL in the LEFT CAMERA when illuminated by the white light of the LEFT LIGHT, according to some embodiments. Because the LEFT CAMERA uses an IR cut filter, the RED CHANNEL therefore can be used for detection of a high reflectivity around the 660 nanometer wavelength, that is, the red wavelength. As explained above, at this wavelength the oxygenated hemoglobin shows a relatively much higher reflectance compared to the deoxygenated hemoglobin. Therefore, the LEFT IMAGING SYSTEM can be used for detecting relative increases or decreases in the oxygenated hemoglobin as a function of time, and further the relative changes in the ratio of the oxygenated hemoglobin in the blood as a function of time.

Figure 33B:
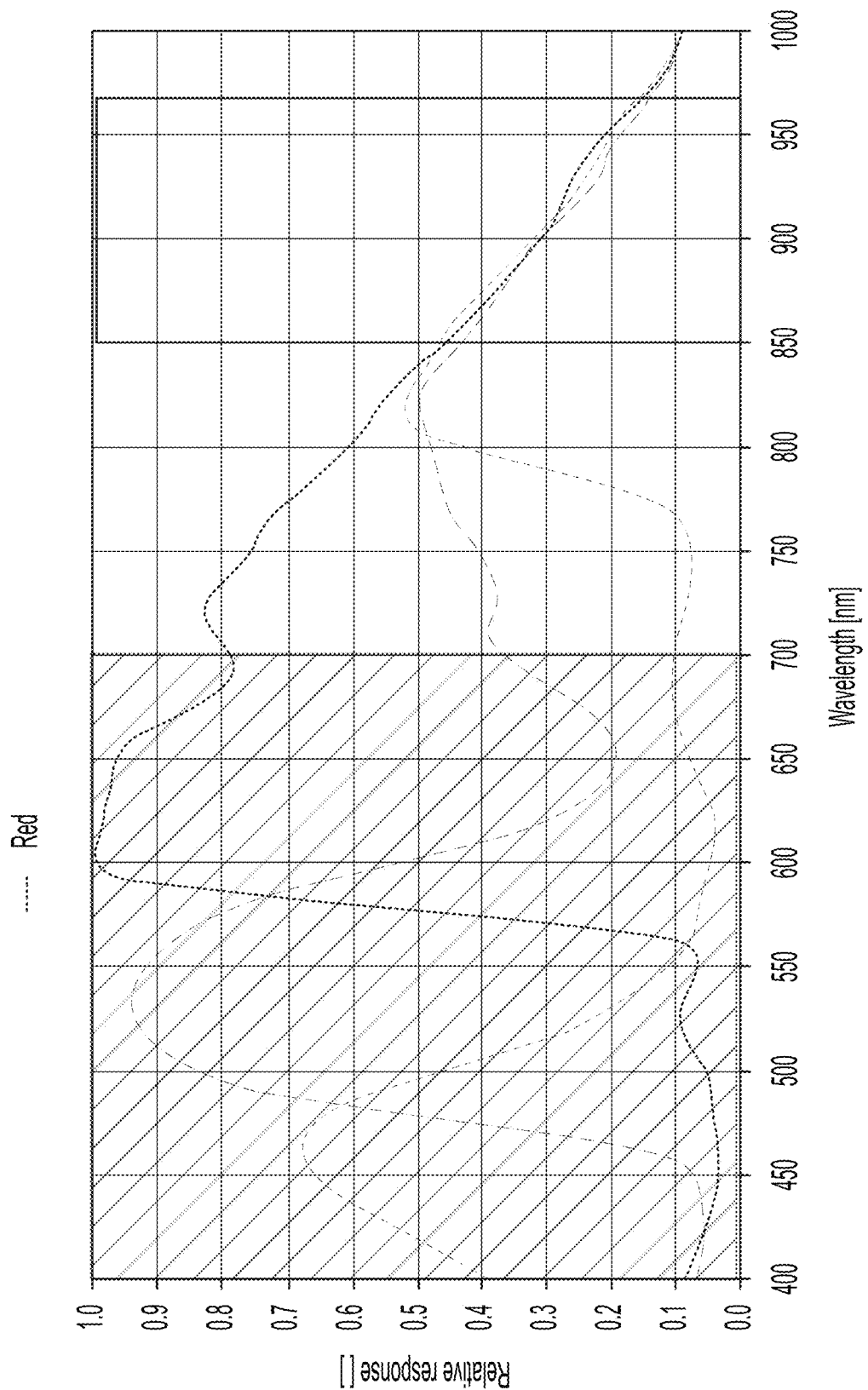

FIG. 33B, on the other hand, illustrates a method of collecting the response around the 940 nanometer wavelength, that is, the IR wavelength. In order to derive the data shown in FIG. 33B the subject is strobed by the 940 nanometer light source (for example, the IR light or the RIGHT LIGHT in the device) and the images collected by the RED CHANNELs of the two cameras are subtracted. Because the RED CHANNELs of the two cameras collect similar data in the visible range of the spectrum, what remains will be the response of the RIGHT CAMERA in the IR range which mostly corresponds to the IR wavelengths and eliminating the response to ambient light in the red region of the spectrum.

Figure 33C:
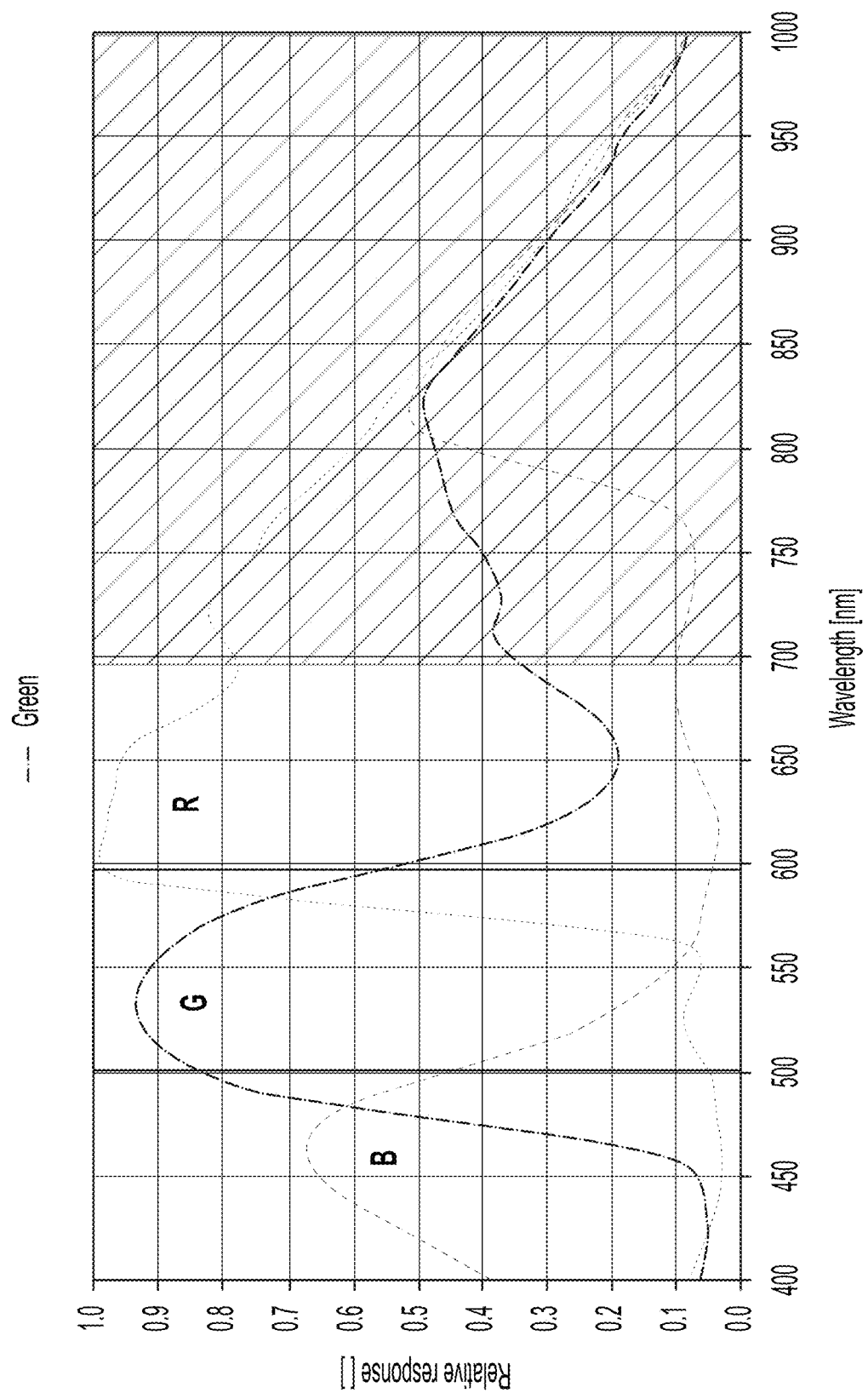

FIG. 33C, further, illustrates a method of collecting the response around the 550 nanometer wavelength, that is, the green wavelength discussed above. In order to derive the data shown in FIG. 33C, the subject may be illuminated by strobing white light from the LEFT LIGHT, and the data are collected from the GREEN CHANNEL of the LEFT CAMERA, which includes the IRC filter.

Figure 33D:
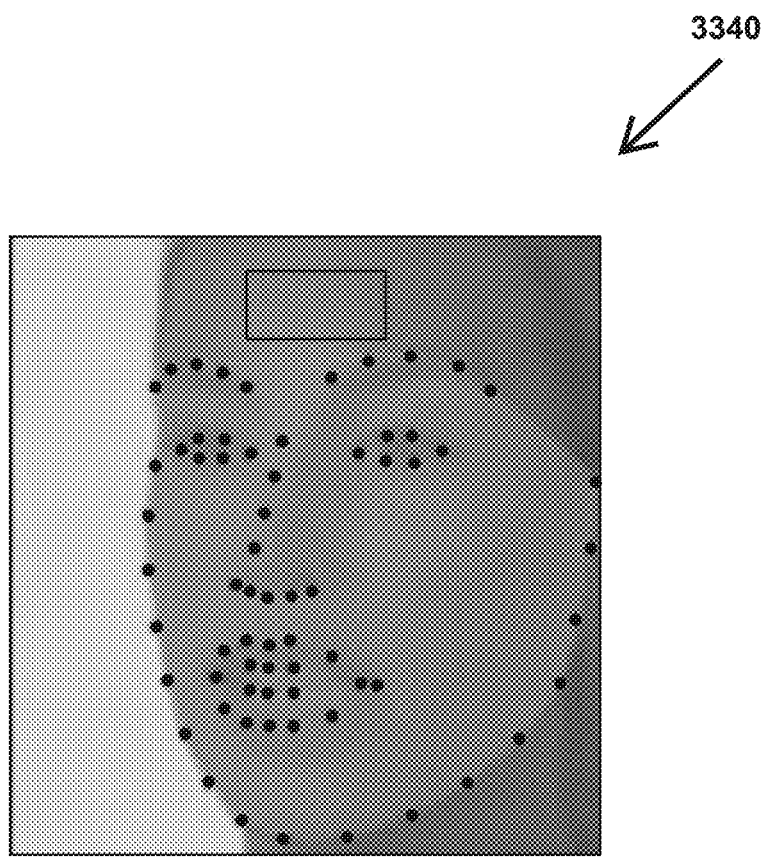

Using the above data, the device may derive the heart pulse rate and the SpO2 of the subject. To that end, the device may collect the data described in relation to FIGS. 33A-33D from a section of the skin of the subject, for example, the subject's forehead or back of the hand, etc. as illustrated in FIG. 33D (including an image 3340). As further explained above, the changes in the absorption in the green wavelength may correspond to the changes in the amount of blood in that section, corresponding to the heartbeat. Moreover, the changes in the reflectivity at the red wavelengths or at the IR wavelengths may correspond to changes in the ratio of the oxygenated hemoglobin and the deoxygenated hemoglobin.

Figure 34:
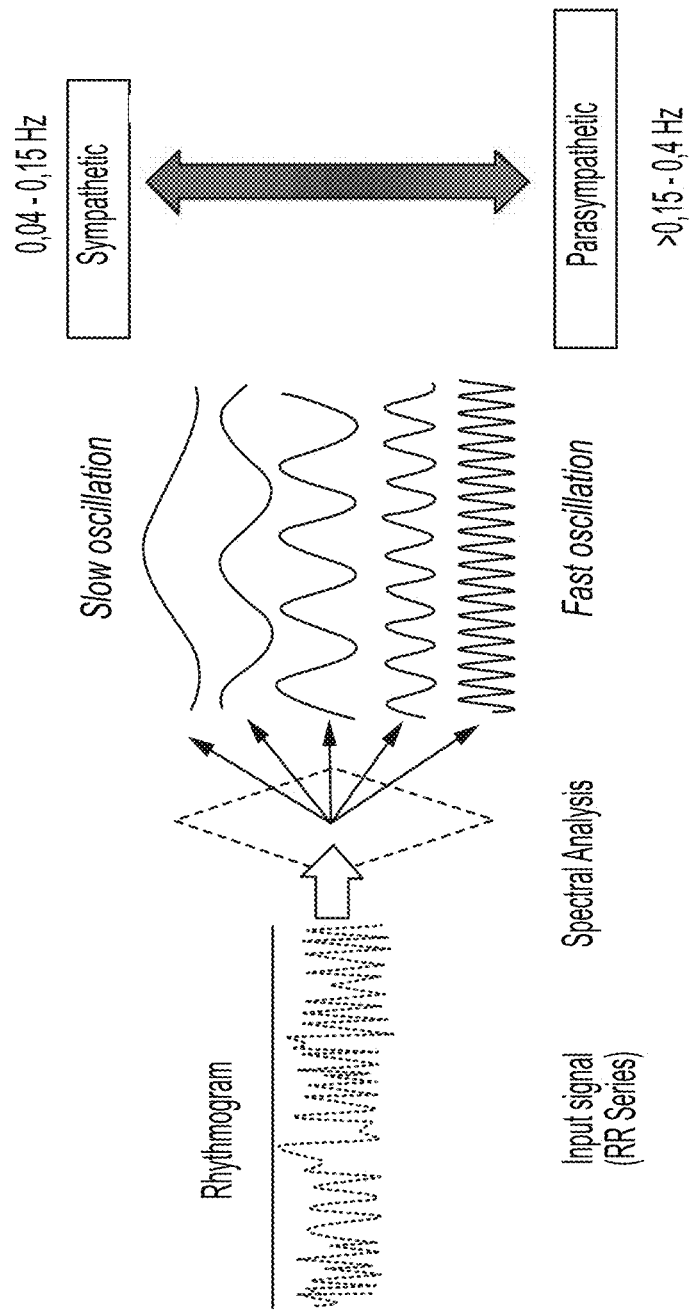
FIG. 34 illustrates a method of deriving the heart rate from the data collected as functions of time, according to some embodiments.

FIG. 34 illustrates a method of deriving the heart rate from the data collected as functions of time, according to some embodiments. In particular, the data may be analyzed via frequency domain transforms e.g. via Fourier or Laplace transformation, and the frequency components in slow oscillations resonating with biological measurements may be selected and higher or lower frequencies rejected. Further, the device may derive the different frequencies at which the data have large amplitude. Some higher frequencies may correspond to the heartbeat rate while some lower frequencies may correspond to the breathing rate.

Figure 35A:
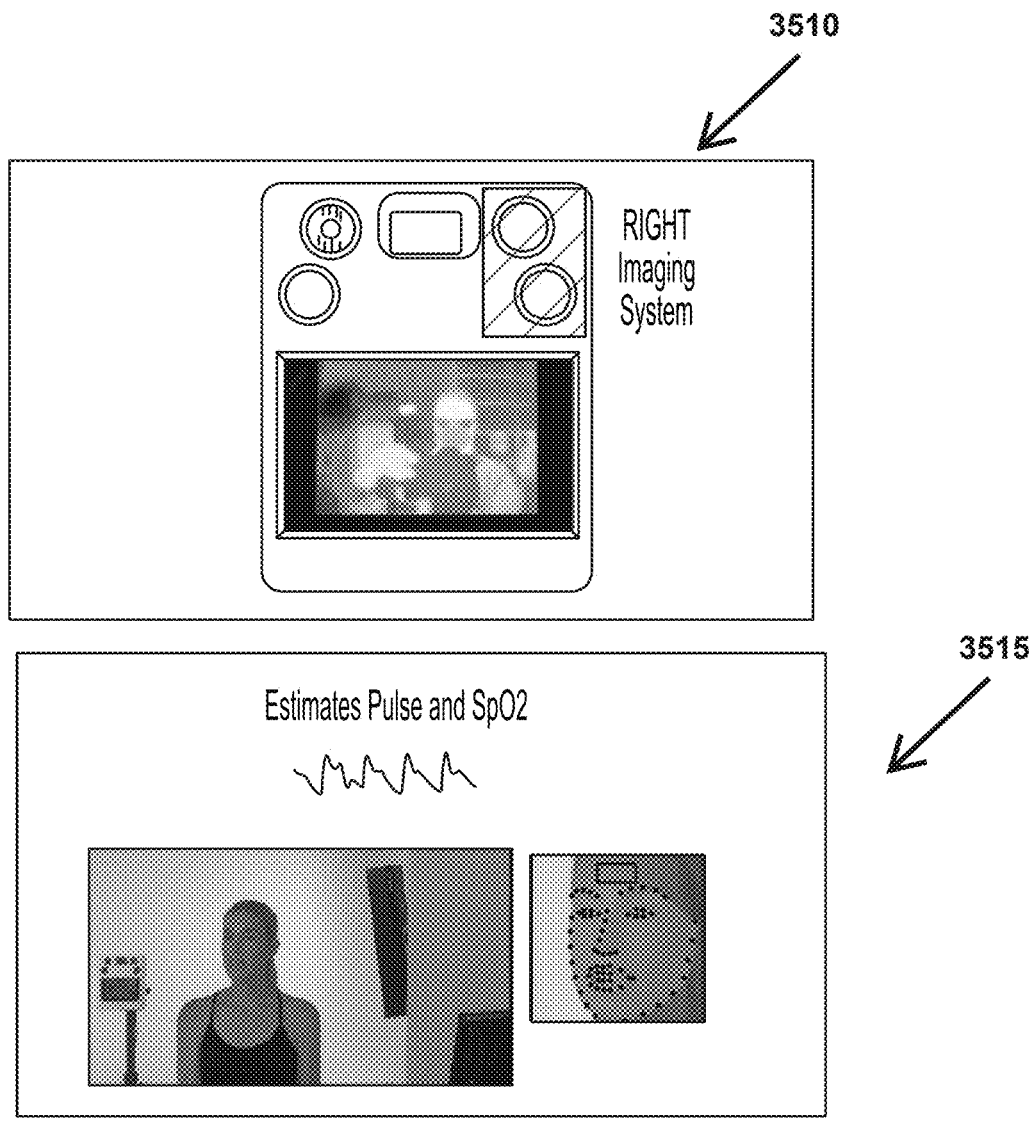
FIGS. 35A and 35B illustrate mechanisms estimating the pulse rate and SpO2 by utilizing the RIGHT IMAGING SYSTEM according to some embodiments.
Figure 35B:
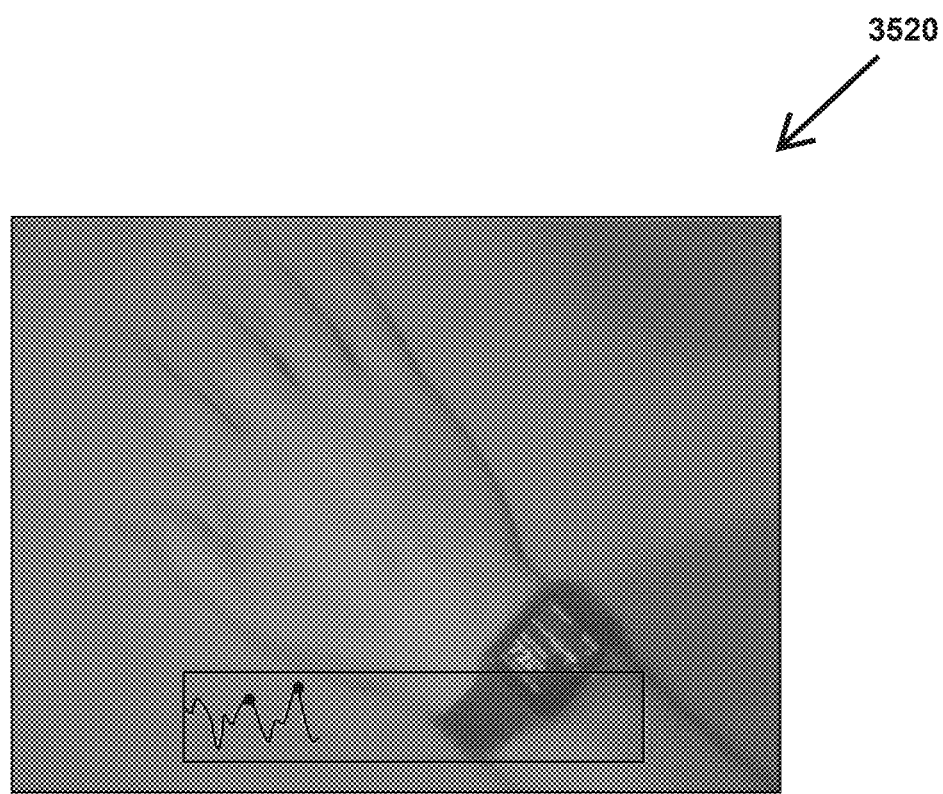

FIGS. 35A (illustrating a system 3510 and an image 3515) and 35B (including an image 3520) illustrate mechanisms estimating the pulse rate and SpO2 by utilizing the RIGHT IMAGING SYSTEM according to some embodiments. More specifically, FIG. 35A illustrates that the device may identify the face of the subject and use the image of the face or a section of the face, for example, an area on the forehead, for measuring the heartbeat rate through pulse oximetry. FIG. 35B illustrates that the device may use the same technique on other extremities of the body of the subject, for example the hand, for measuring the heartbeat rate.

Figure 36A:
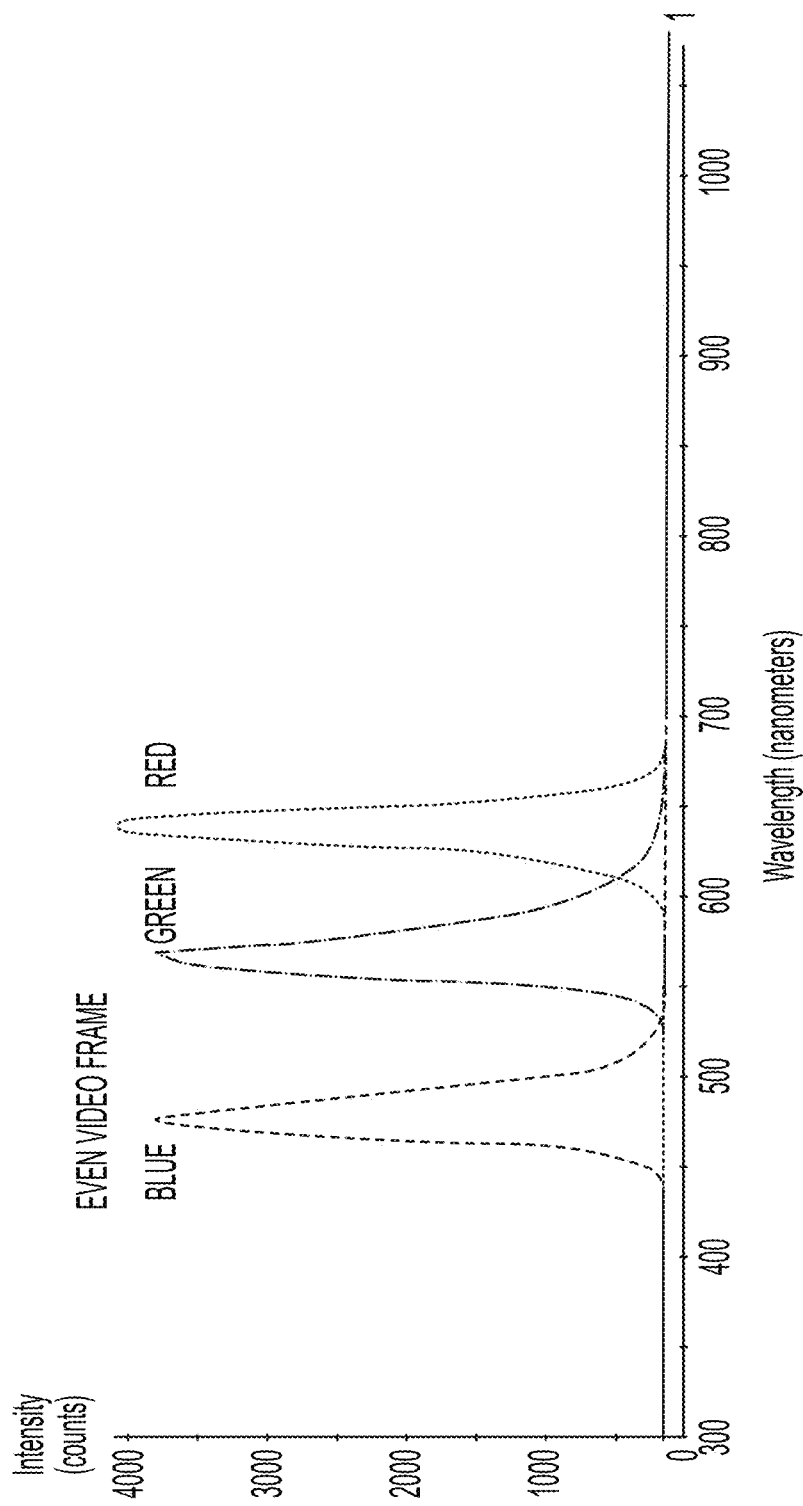
FIGS. 36A and 36B illustrate the mechanism of illuminating the subject via the LEFT LIGHT and alternatively the RIGHT LIGHT in different sampling time intervals, according to some embodiments.
Figure 36B:
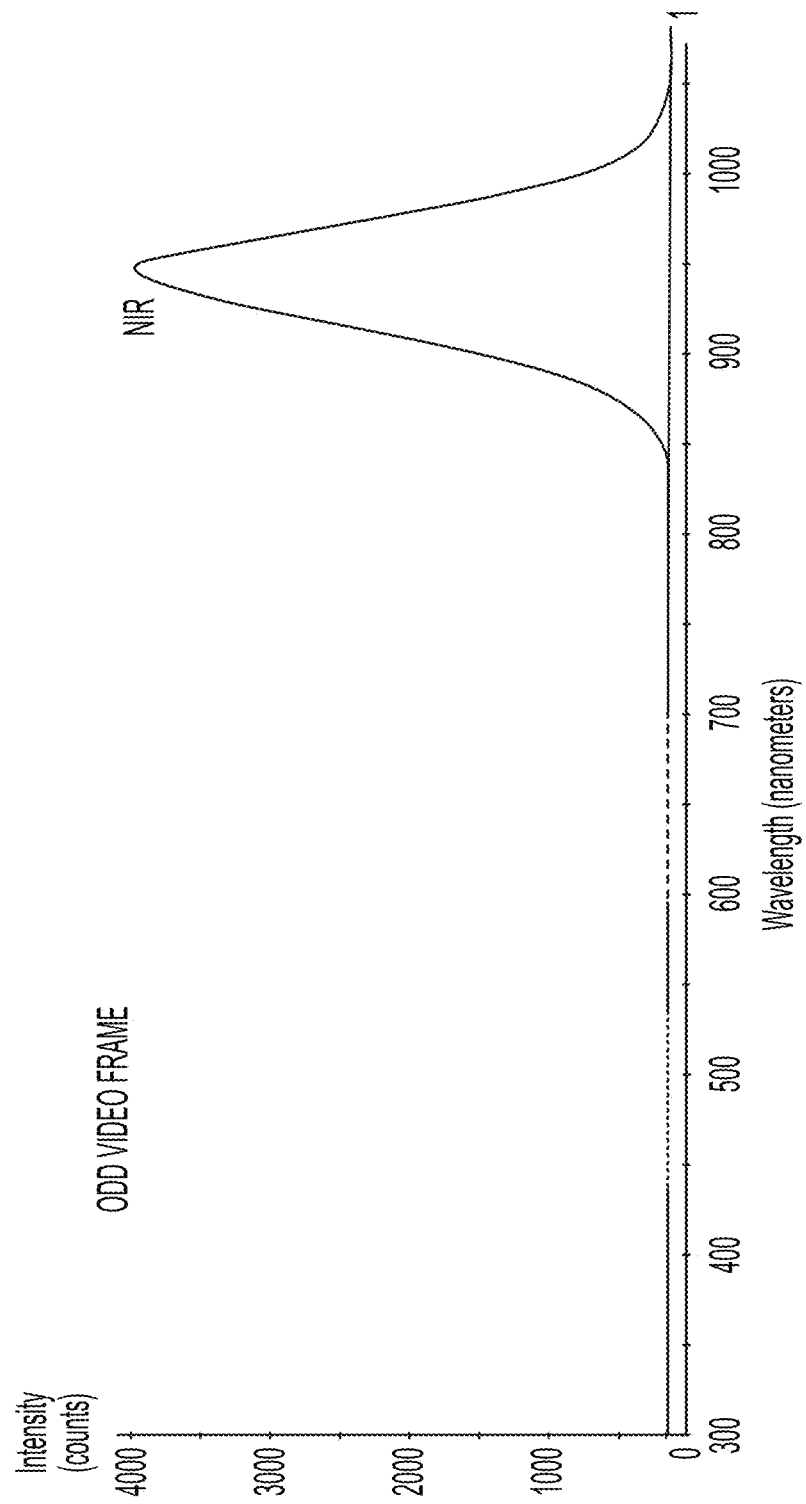

FIGS. 36A and 36B illustrate the mechanism of illuminating the subject via the LEFT LIGHT and alternatively the RIGHT LIGHT in different sampling time intervals, according to some embodiments. This mechanism may enable simultaneous data collection in selected parts of the light spectrum by the LEFT CAMERA and RIGHT CAMERA to perform computations as described above.

In particular, FIG. 36A shows that in one embodiment, the LEFT LIGHT source of the LEFT IMAGING SYSTEM may send pulses of white light at even numbered video frames. These pulses enable collection of data for the red wavelength described in FIG. 33A, green wavelength described in FIG. 33C, and further used for the subtraction method of deriving the data in the IR wavelength, described in relation to FIG. 33B. Therefore, at the even frame times, the corresponding data from the corresponding channels of the LEFT CAMERA or the RIGHT CAMERA are collected in the manner described in FIGS. 33A-33C. FIG. 36B, on the other hand, illustrates that in that embodiment, the IR strobe light source of the RIGHT IMAGING SYSTEM may send pulses of IR light at odd numbered video frames. These pulses enable collection of data for this subtraction method of deriving the data in the IR wavelength, described in relation to FIG. 33B.

In some embodiments, similar methods may be used by the thermal imaging system for detecting temporal changes of the thermal radiation of parts of the subject's skin due to measured temperature changes in blood flow rate to different parts of a person's body.

Figure 37A:
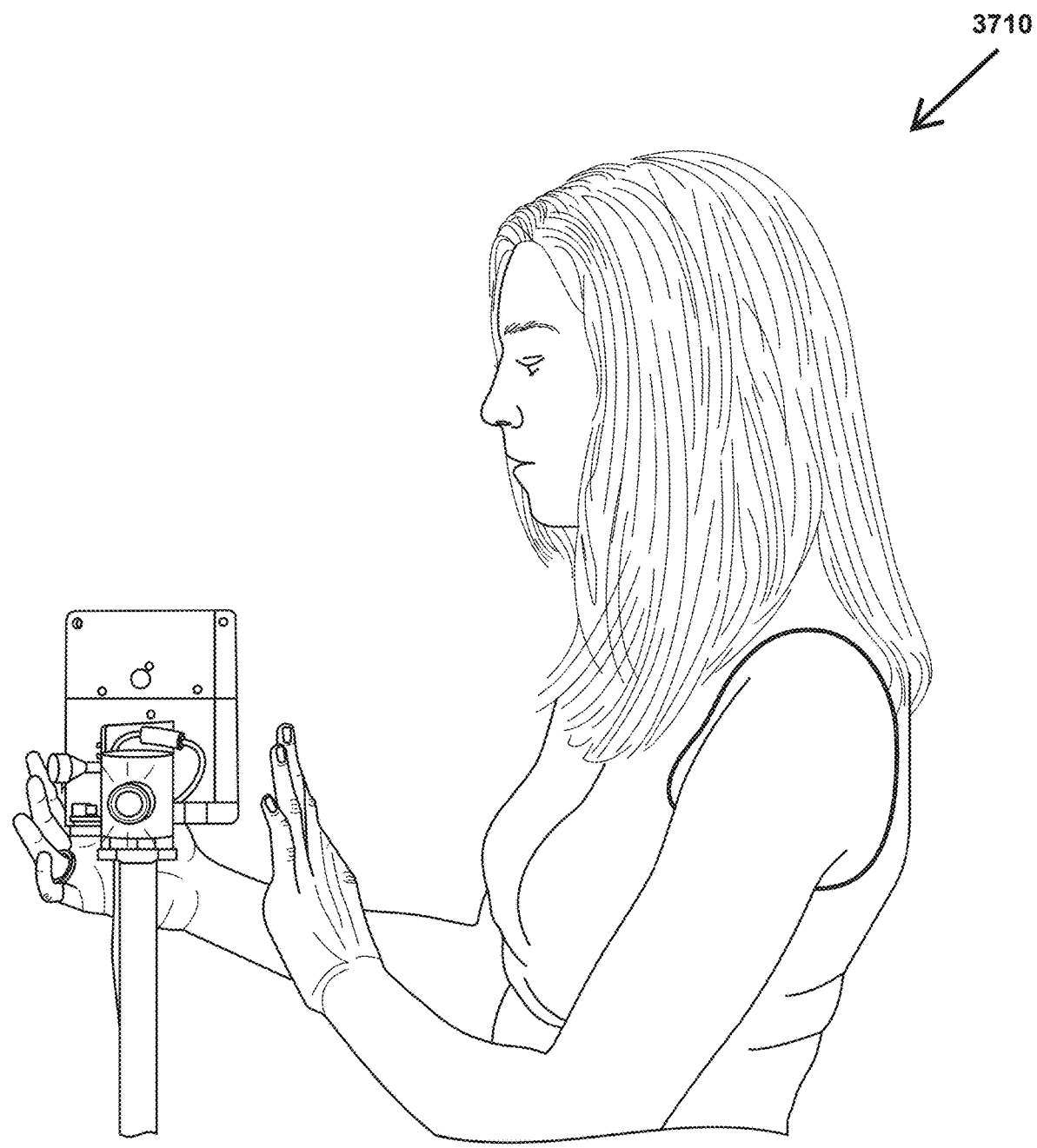
FIGS. 37A and 37B illustrate mechanisms by which the device may interact with an operator or collect information from a subject according to some embodiments.
Figure 37B:
Figure 37B:
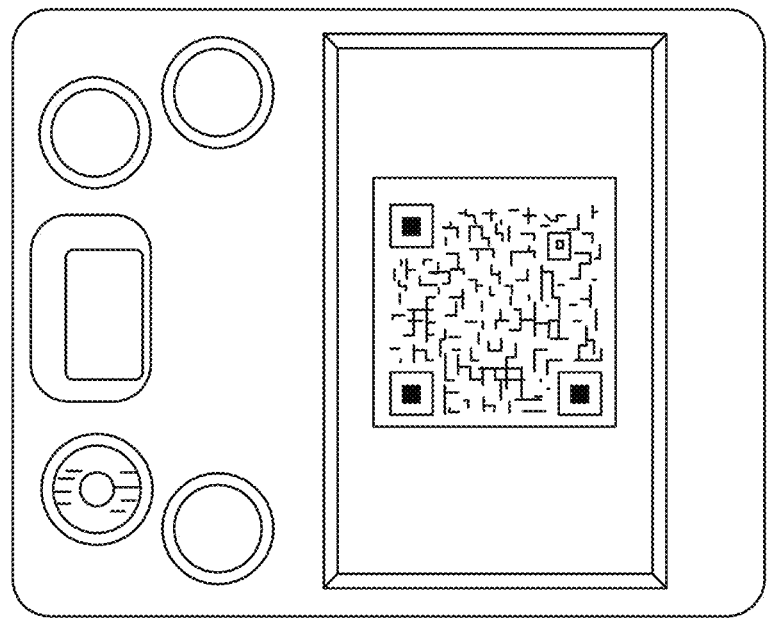
Figure 37B:
Figure 37B:
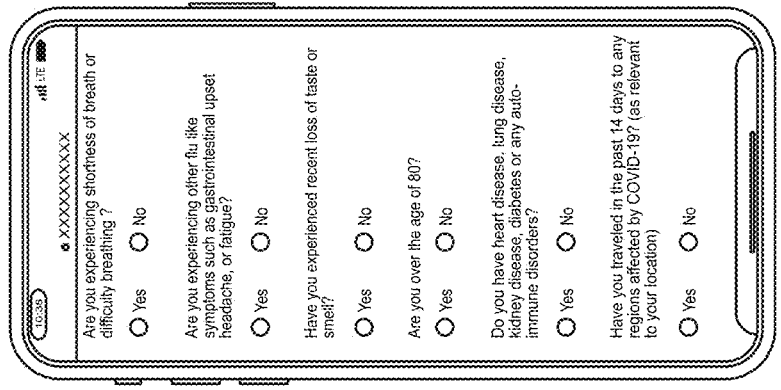

FIGS. 37A (including an image 3710) and 37B (illustrating a questionnaire 3720 and a system 3725 with a QR code display) illustrate mechanisms by which the device may interact with an operator or collect information from a subject according to some embodiments. In particular, as shown in FIG. 37A, the device may assess the relevant health characteristics of a subject based on the collected data and accordingly summarize it by some signal. For example, the device may generate a warning if the subject has a body temperature that is above normal range, therefore indicating a fever, or the pulse rate or blood oxygen level is outside an acceptable range. In such cases, the device may generate a warning by, for example, issuing a specific audio signal such as a chime, or a visual signal, such as turning on a red light in the back of the device, etc. The operator of the device may react to such a warning by, for example, interviewing the subject. The interview may include, for example, a request that the subject provide some additional information regarding their health condition or further examination by medical staff. The additional information may be collected, for example, through an electronic questionnaire presented to the subject. The subject may be presented with the questionnaire or presented with an Internet address of the questionnaire through, for example, a QR code appearing under display of the device, as shown in FIG. 37B.

As stated below, modifications and variations are possible in light of the above teachings or may be acquired from practicing the embodiments. For example, and without limitation, various embodiments may place different parts in places other than those described in the above embodiments, or combine, divide, or eliminate some of the described parts. For example, the distinction and terms LEFT IMAGING SYSTEM and RIGHT IMAGING SYSTEM are given as examples, and other embodiments using the same methods described above are possible. Moreover, and for example, some embodiments may not include the display.

Figure 38A:
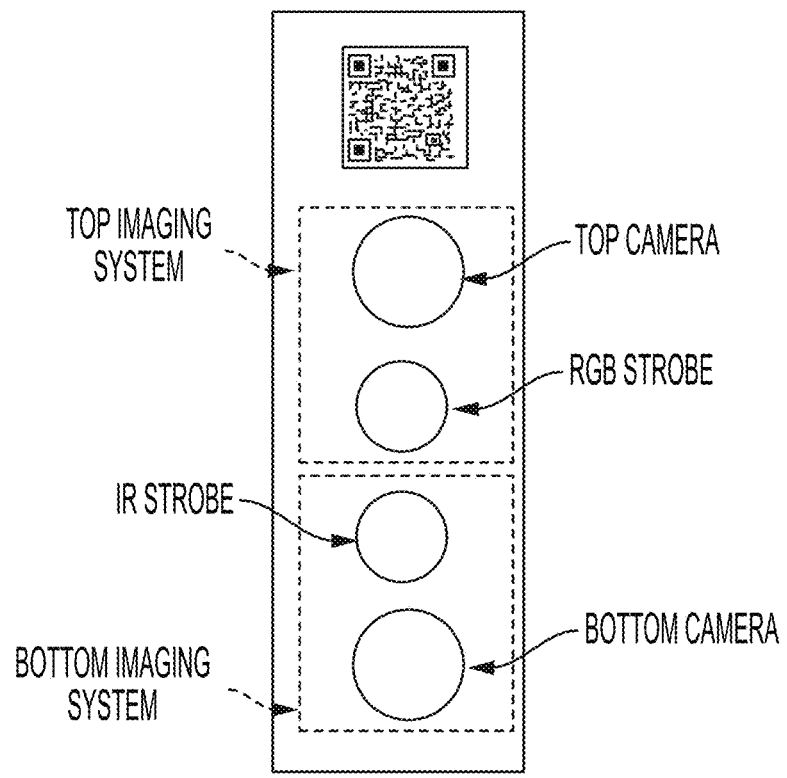
FIGS. 38A-38D show some examples of alternative embodiments.
Figure 38B:
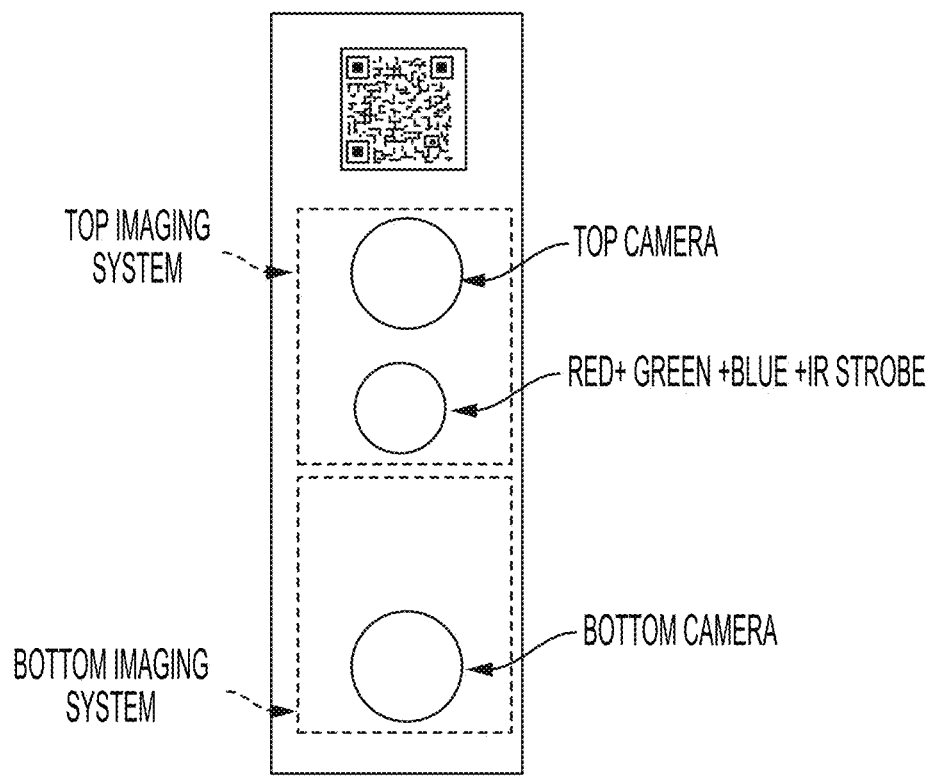
Figure 38C:
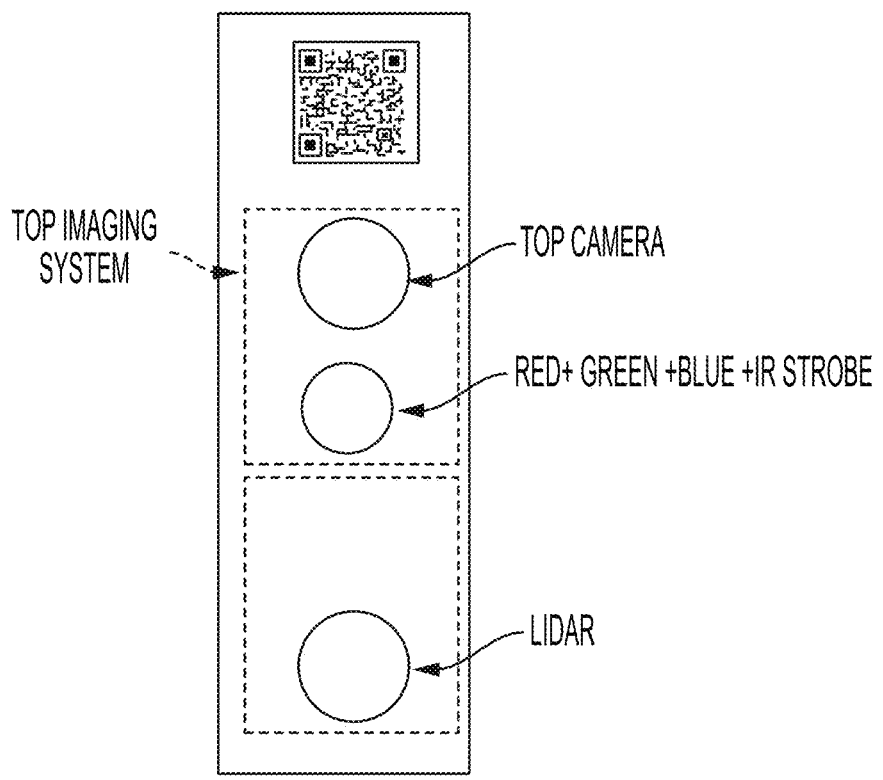
Figure 38D:
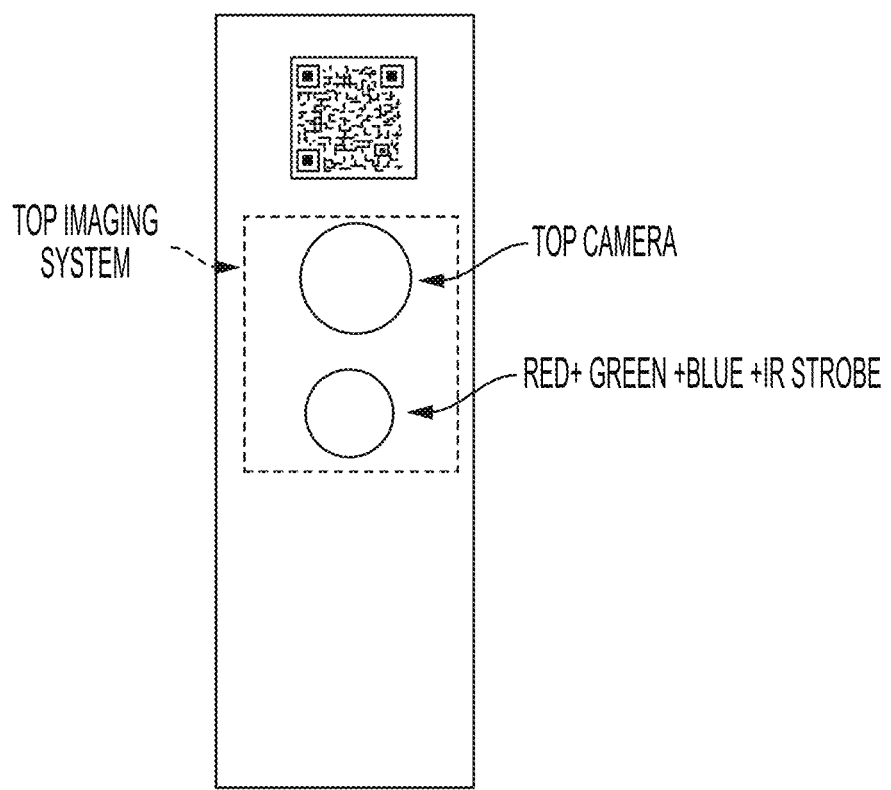

FIGS. 38A-38D show some examples of alternative embodiments illustrating the above. For example, FIG. 38A shows an embodiment that includes a TOP IMAGING SYSTEM and a BOTTOM IMAGING SYSTEM arrangement. FIG. 38B shows an embodiment in which the RED+GREEN+BLUE+IR strobes are integrated into a single light source. FIG. 38C shows an embodiment in which Lidar or Sonar is used instead of the stereo system to estimate the subject's distance. FIG. 38D shows an embodiment that includes only a TOP IMAGING SYSTEM and may not include a method for measuring a distance, usable in cases that the subject is required to be at a fixed distance, for example.

Some embodiments utilize one or more versions of the above described imaging systems as an imaging module in a system for monitoring a human operator of critical equipment as further described below. In various embodiments the critical equipment may be an equipment that is operated by a human operator. In some embodiments, the monitoring system may monitor the biological status of the human operator for detection of signs of some biological problem that may affect the capability of the human operator to operate the critical equipment in a way that may cause serious harms or financial losses. For example, the critical equipment may be an equipment that requires uninterrupted alertness of the operator. The equipment may include, for example, heavy machinery (chainsaw, crane, etc.), a transportation vehicle (a bus, a train, an airplane, a car, etc.), or a critical monitoring system (air traffic control system, security monitoring cameras, etc.).

Moreover, the biological problem may include a problem that reduces the alertness of the operator. The biological problem may include, for example, high level of fatigue, drowsiness, seizure, heart attack, stroke, etc. In various embodiments, the monitoring system may detect that the biological problem has already occurred, or that the risk of its occurrence within a time interval is higher than a threshold probability or that. In various embodiments, the time interval may be a time interval between one minute and one hour (for example, 5 minutes, 15 minutes, 30 minutes, etc.) or a few hours or a few days. Moreover, the threshold probability may have a value between zero and 100% such as, 20%, 50%, 80%, etc.

In some embodiments, the value of the time interval or the threshold probability may depend on the critical equipment. For example, a highly critical equipment, such as an air control system or a train, may require an uninterrupted and high level of alertness. In this case, the threshold probability or the time interval may need to be set to relatively smaller values, such as values below 50% and one minute, respectively. A less critical equipment such as a self-driving train or a security monitoring camera in a relatively safe location, may tolerate a lesser level of alertness or a higher risk of interrupted alertness. In such cases, the threshold probability or the time interval may be set to relatively higher values, such as values above 50% or more than a few minutes, respectively.

Figure 39:
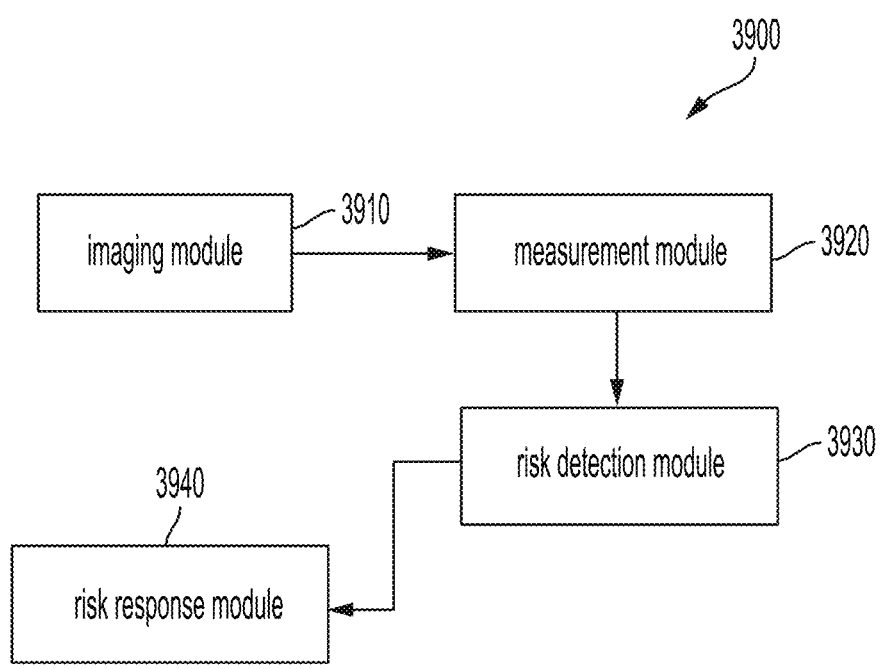
FIG. 39 shows a monitoring system utilized for monitoring an operator of a critical equipment according to some embodiments.

FIG. 39 shows a monitoring system 3900 utilized for monitoring an operator of a critical equipment according to some embodiments. System 3900 includes an imaging module 3910, a biometric measurement module 3920, a risk detection module 3930, and a risk response module 3940. The different parts or modules of the monitoring system 3900 may communicate with each other through wired or wireless connections.

The imaging module 3910 may include, for example, one or more imaging devices such as the LEFT IMAGING SYSTEM or the RIGHT IMAGING SYSTEM, both described above. The imaging module 3910 may include a light source, a camera, and an imaging data generator, each described below.

The light source may be a multi-spectral light source that is configured to emit light in a first spectral wavelength range to illuminate some portions of the body of the operator. The first spectral wavelength range may include, for example, one or more of the wavelength regions around the green wavelength, the NIR, the IR, the whole visible spectral range, etc. The multi-spectral light source may include one or more separate light sources each emitting light in one of the wavelength regions.

The camera may be configured to detect light in a second spectral wavelength range. In particular, the camera may detect light received from some portions of the body of the operator. The received light may include reflections of the light emitted by the light source. The second spectral wavelength range may include, for example, one or more of the wavelength regions around the green wavelength, the NIR, the IR, the whole visible spectral range, etc. In various embodiments, the first and the second spectral wavelength ranges may be the same, may partially overlap, or may not overlap. The camera may include one or more separate cameras each detecting light in one of the wavelength regions.

The imaging data generator may be configured to generate image data based on the emitted light and the detected light. The image data may, for example, include the values of the wavelengths included in the emitted light and in the detected light. The image data may further include, for example, the intensities of those wavelengths. The image data may further include data indicating the above emissions and detections as functions of time.

The biometric measurement module 3920 may be configured to receive the image data from the imaging module 3910 and, based on the image data, perform one or more biometric measurements on the human operator. The biometric measurement may include, for example, measuring an oxygen level of blood, a heartbeat rate, a blood pressure, a body temperature, or a breathing rate. The biometric measurement module 3920 may include one or more hardware or software modules, as further explained below, that perform the biometric measurement by utilizing one or more of the techniques described earlier.

The risk detection module 3930 may be configured to receive the biometric measurements from the biometric measurement module 3920 and, based on those measurements, establish a safety risk associated with the human operator. The safety risk may include the risk of occurrence of one or more unsafe conditions. By way of example, the unsafe conditions may include conditions in which further operation of the critical equipment by the human operator would pose high risks of harm or financial damage. The unsafe conditions may include, for example, a high level of fatigue or an occurrence of events such as fainting, seizure, heart attack, or stroke. To establish the safety risk, the risk detection module 3930 may compare one or more of the biometric measurements with a safety range for those measurements. Further, an alarm may be raised if the biometric measurement is outside the safety range, which may also be called an alarm range.

The risk response module 3940 may be configured to receive the safety risk and based on that risk, generate a risk response. The risk response module 3940 may, for example, generate the risk response if the probability of occurrence of an unsafe condition within a threshold time interval exceeds a safety limit. The safety limit may include, for example, a 50% probability of occurrence of the unsafe condition.

Moreover, the risk response may include one or more actions that reduces or eliminates the probability of occurrence of the unsafe condition. The risk response may, for example, include emitting an audio alarm, such as a siren or another type of loud noise, to alert the human operator (for example, in the case of detecting that the operator is suffering from high fatigue) or to alert others near the operator to address the unsafe condition. The risk response may also include, for example, halting the critical equipment (such as the chainsaw), transferring control of the critical equipment to another operator (for example, from the pilot to the co-pilot of an airplane), overriding the operator over the equipment (for example, in the air traffic control room), or sending an alarm message. The risk response module 3940 may include hardware or software for performing the one or more actions; for example, an audio alarm generator.

Figure 40:
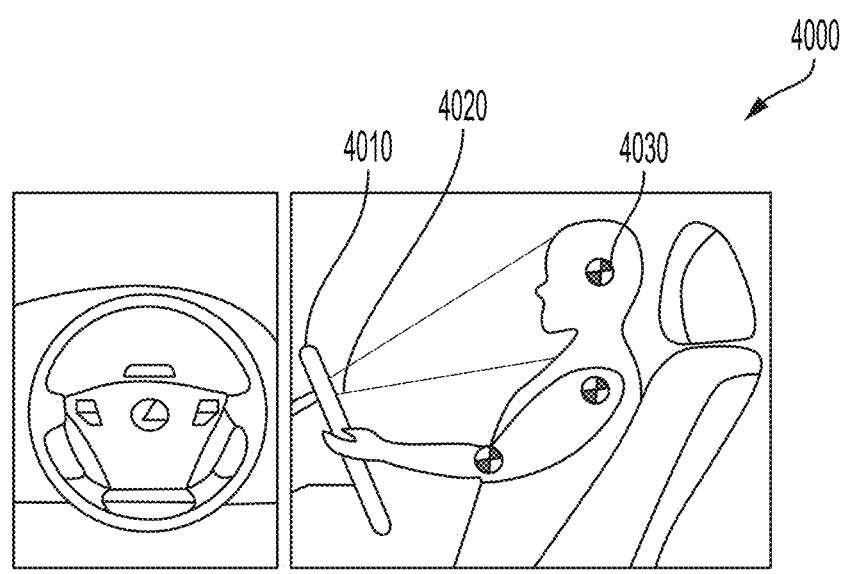
FIG. 40 shows a set-up in which a monitoring system may be utilized according to some embodiments.

FIG. 40 shows a set-up 4000 in which a monitoring system may be utilized according to some embodiments. The set-up 4000 includes a critical equipment 4010, an imaging module 4020, and a human operator 4030.

In the example of set-up 4000, the critical equipment 4010 is a car. In FIG. 40, the imaging module 4020 is placed in a location from which it can emit light toward, and detect light received from, the face of the human operator 4030. In different embodiments, the imaging module 4020 may be installed at different locations from which it can emit light toward one or more parts of the body of the human operator 4030. Moreover, the imaging module 4020 may be in communication with the other parts of the monitoring system, such as the biometric measurement module. The other parts may be located inside or outside set up 4000.

Figure 41:
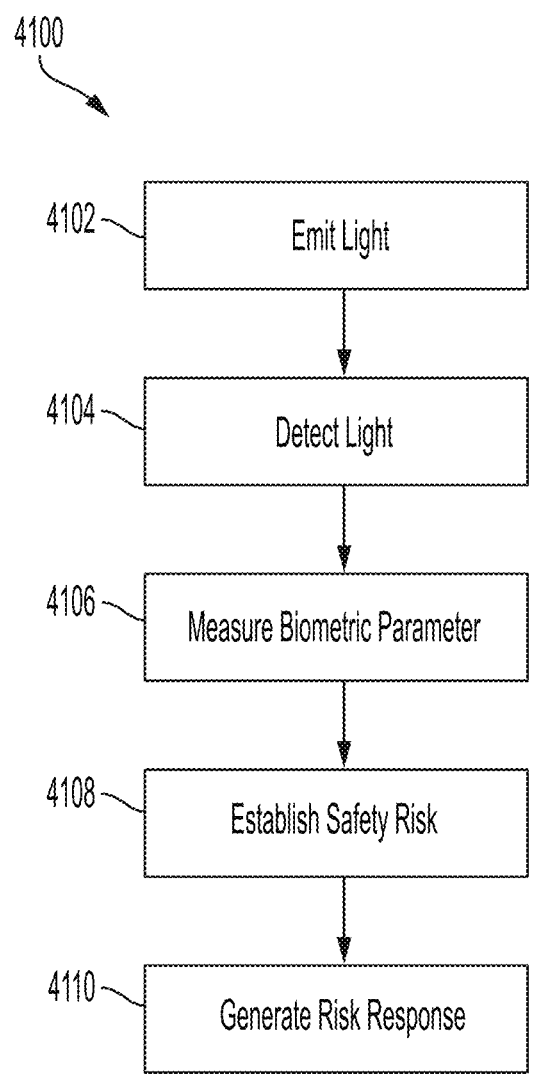
FIG. 41 shows a flow chart for an operation of a monitoring system according to some embodiments.

FIG. 41 shows a flow chart 4100 for an operation of a monitoring system according to some embodiments.

In step 4102, the imaging module emits light toward the human operator.

In step 4104, the imaging module detects light received from the human operator.

In step 4106, the biometric measurement module measures one or more biometric parameters.

In step 4108, the risk detection module establishes a safety risk.

In step 4110, the risk response module generates a risk response based on the safety risk.

Hereinbelow, some technological aspects of the IRT imaging-based temperature measurement are described for better understanding of the subject matter of the present disclosure.

IR Thermography

Figure 22:
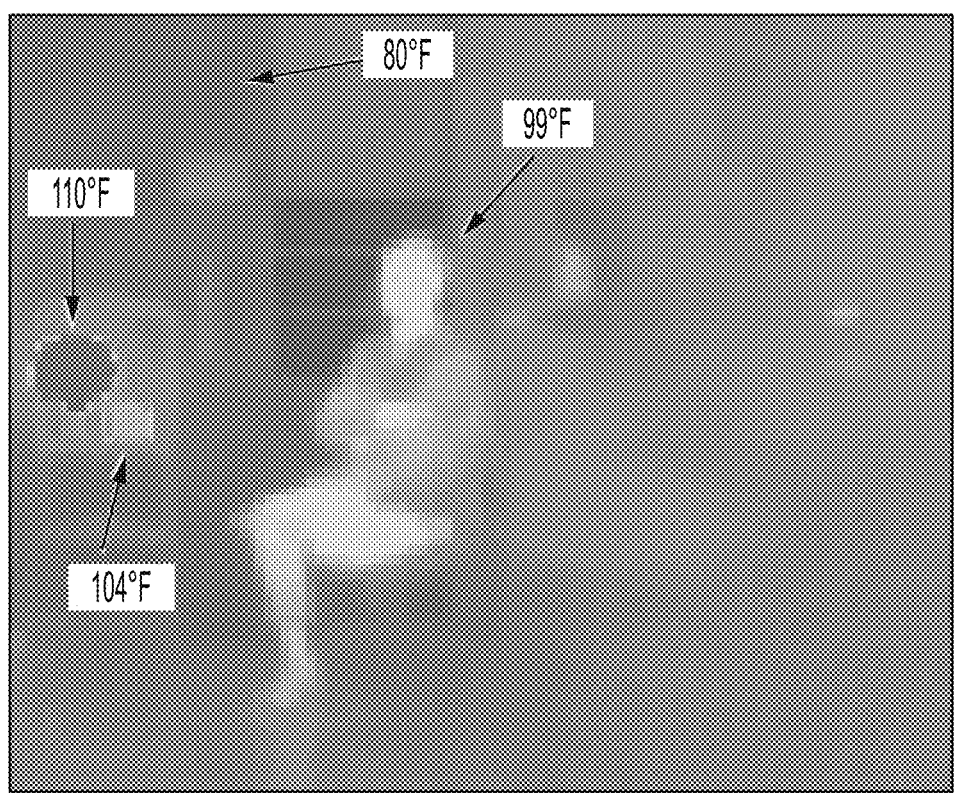
FIG. 22 shows an example of a scene perceived by IR thermography.

An IRT imaging device according to the present teachings can create a temperature map of radiation sources by capturing and measuring the flux of infrared light energy emitted from a body. FIG. 22 shows an example of a conventional thermal image captured by an IRT imaging device for a scene in which a person is seated adjacent to a hot lamp and a cold windows in the background. The temperatures indicated on FIG. 22 are typically accurate to ±3° C. without the presence of a black body reference in the scene and ±0.5° C. if the calibration source is present. Planck's radiation law models electromagnetic energy radiation of a black body (a perfect emitter) at particular radiation frequency wavelengths "A, where k is the Boltzmann constant, h is the Planck constant, and c is the speed of light:

$$E_\lambda = \frac{8\pi hc}{\lambda^5} \times \frac{1}{\exp(hc/kT\lambda) - 1}.$$

Figure 23:
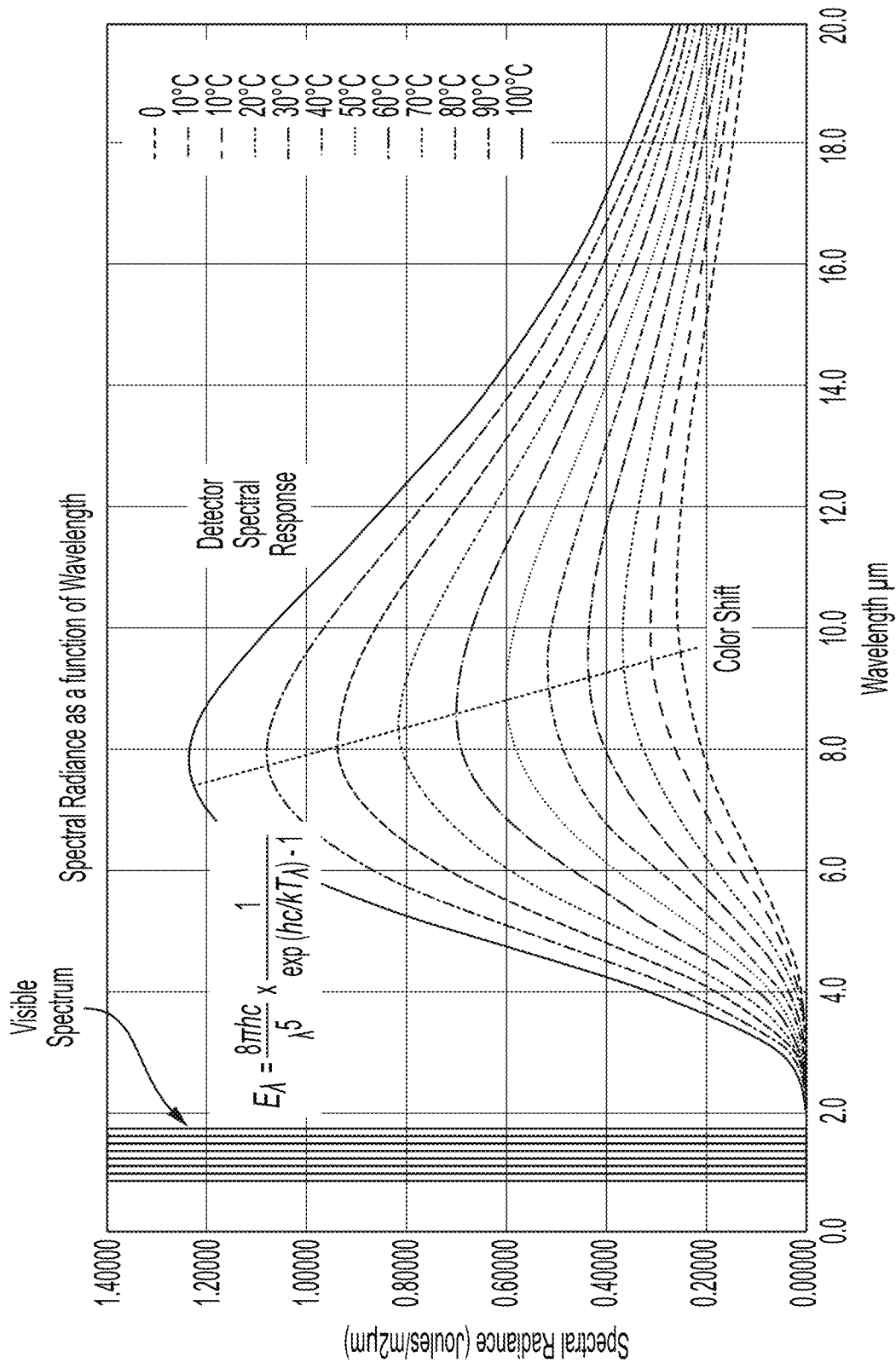
FIG. 23 shows spectral radiance of a black body as functions of source temperature of objects between the freezing and boiling point of water.

As the black body's temperature increases, so does the total radiated energy. Further, the peak of the emitted spectrum shifts to shorter wavelengths. The temperature of the body can be determined from the "color" of the source radiation and many techniques and types of detectors have been developed for this purpose in prior art. The body's temperature is commonly measured by observing a resistance change at the detector photosites with absorbed heat or through photovoltaic measurements. FIG. 23 shows spectral radiance of a black body as a function of source temperature.

IRT Image Sensors

In some embodiments, an IRT sensor according to the present teachings can include an array of microbolometers, e.g., with a typical pixel size of 12 µm-25 µm, arranged in a Focal Plane Array (FPA) that can produce a 2D thermal map of a scene (a subject) in combination with a lens.

While in some embodiments, cooled microbolometers are used, in other embodiments, uncooled microbolometers can be employed. In general, cooled microbolometers provide higher temperature sensitivity and stability as they are operated as very low temperatures. They can, however, be expensive and difficult to operate. Uncooled thermal imaging sensors work at room temperature and are relatively low-cost but require regular calibration for precise temperature readings. As discussed above, in many embodiments of the present teachings, an integrated reference thermal mass is employed for calibrating the system.

Most commercially available uncooled microbolometers use Micro Electro Mechanical System (MEMS) structures holding thin-film resistors that change resistance in response to absorbed heat radiation. The leading commercial thin-film material is Vanadium Oxide (VOx) with a spectral response peaking in Long Wave Infrared (LWIR) 8 µm-14 µm wavelengths with better than 0.05° C. resolution. Because of the MEMS construction and large pixel sizes (12 µm-25 µm), microbolometers become large and complex as pixel count is increased. Accordingly, tens to hundreds of thousands of pixels for commercial applications are practical using current fabrication technology.

Thermal Emissivity

Planck's radiation law is defined in terms of ideal emitters also known as black bodies. In real-world situations, different objects have different emissivity depending on their efficiency to emit thermal energy. Emissivity is defined as the fraction of energy being emitted by an object relative to that emitted by an ideal black body. A material that is a perfect emitter of heat energy has an emissivity value of 1. A material with an emissivity value of 0 would be considered a perfect thermal mirror. If an object can potentially emit 100 units of energy but only emits 90 units in the real world, then that object would have an emissivity value of 0.90. Although there are rarely perfect thermal black bodies (or mirrors), most common objects have an emissivity of 90% or higher. Humans behave as near perfect radiators with stable temperatures on the scale of minutes or even hours. However, factors such as clothing can impact observed emissivity. Table I below lists emissivity values for several materials.

TABLE I

| Material | Emissivity |
|---|---|
| Skin, Human | 0.97 to 0.999 |
| Water and Ice | 0.97 |
| Glass, smooth (uncoated) | 0.95 |
| Aluminum, Copper anodized | 0.9 |
| Concrete, Brick, paint, plaster, asphalt, paper, roofing | 0.9 |
| Aluminum foil | 0.03 |

By using standard AI training datasets the present invention determines the type of material being observed and therefore an estimated emissivity of the object as well as its surrounding using a lookup table of standard emissivity values.

EBT Detection Requirements

The average normal body temperature of a human is generally accepted as 98.6° F. (37° C.). Normal body temperatures vary by person, age, activity, and time of day. Some studies have shown that the normal body temperature can have a wide range, from 97° F. (36.1° C.) to 99° F. (37.2° C.). A person with a body temperature of 100.4° F. (38° C.) is generally considered to have a fever, presumably caused by an infectious disease or illness in the medical community.

Measurement accuracy of various thermometers have been documented in medical journals with a precision and accuracy of fractions of a degree considered the norm. Typically, an ear (Tympanic) temperature is 0.5° F. (0.3° C.) to 1° F. (0.6° C.) higher than an oral temperature. An armpit (axillary) temperature is usually 0.5° F. (0.3° C.) to 1° F. (0.6° C.) lower than an oral temperature. A forehead (temporal) scanner is usually 0.5° F. (0.3° C.) to 1° F. (0.6° C.) lower than an oral temperature.

Uncooled microbolometer are typically specified with a radiometric accuracy in the range ±2° C. to ±3° C., which present challenges when used to detect EBT or a fever. For example, a subject with a body temperature of 40° C. (101.6° F.) fever could be falsely detected as normal (98.6° F.) if the device has an error margin ±2° C., or vice-versa, someone with a normal temperature could be registered as having a fever.

Livestock can also become infected with certain viruses and similar to humans exhibit EBT. Animals have slightly higher normal body temperatures. For example, the normal temperature for cattle is considered >101.5° F. (>38.5° C.). Fever in cattle is called Pyrexia, and an animal is considered febrile with a temperature of >103° F. (>39.4° C.).

Temperature Precision and Accuracy Issues Associated with Prior Art IRT Systems

Cooled IRT systems produce accurate remote temperature measurements in laboratory environments, but increasingly being replaced with uncooled microbolometer due to operating cost and complexity. There are three primary causes for inconsistent results when using uncooled microbolometers in performing precision EBT measurements as follows;

1) Electronic Temperature Drift

Direct uncooled microbolometers readings are inherently unstable over time periods of seconds to tens of seconds. The instability can be caused by electronic temperature drifts in the sensor. Without being limited to any particular theory, in some cases, the electronic temperature drift can be the result of a change of the detector's temperature that is not caused by the incident radiation from an external object. For example, the highly sensitive VOx thin-film resistor pixel elements pickup heat through conduction and radiation from the semiconductor die and camera housing.

As discussed above, in many embodiments, the use of active, real-time (e.g., periodic or substantially continuous) calibration of the system as described herein can enhance the accuracy of temperature measurements even when uncooled microbolometers are used as infrared detectors.

2) Distance to Subject

As discussed above, the air has the capacity to absorb and emit thermal energy as radiation passes through it. The absorption or emission of thermal energy is highly dependent on the air temperature, density, humidity, and the distance to the subject, and has a strong impact on the measurements. Moving subjects present an extra challenge as fluctuating temperature readings can be recorded at different distances from the camera, 3) Emissivity Variations Although humans are almost perfect radiators, the exposed part of a person's body is normally the head, and there are considerable variations between different people. The presence of eyeglasses, masks, facial hair, make-up, or perspiration as well as facing direction will impact the temperature readings. Asking a person to alter their head coverings for the purpose of a temperature measurement is sometimes impractical or even unsafe, and will certainly disrupt the normal flow of traffic if the measurement station is set up at a location where there is a flow of traffic.

As set forth herein, the subject matter of the present disclosure provides an IRT imaging-based temperature sensor system. As described above, by including within the system a black body probe (herein also referred to as a reference thermal mass), the temperature of which is measured and/or controlled in-situ, the IRT imaging system according to the present disclosure may obtain a reliable reference temperature, against which the infrared detector can be calibrated, thereby maintaining a compact form factor and low cost. Further, by including a LIDAR sensor to measure a distance to the subjects, the temperature signals measured by the infrared detector can be compensated for the distance, thereby reducing or minimizing the bias caused by the distance. In addition, by further correcting the temperature signals measured by the infrared detector based on the ambient temperature and/or humidity measured in-situ, the effect of the distance can be more accurately compensated for.

In various embodiments, one or more of disclosed modules may be implemented via one or more computer programs for performing the functionality of the corresponding modules, or via computer processors executing those programs. In some embodiments, one or more of the disclosed modules may be implemented via one or more hardware units executing firmware for performing the functionality of the corresponding modules. In various embodiments, one or more of the disclosed modules may include storage media for storing data used by the module, or software or firmware programs executed by the module. In various embodiments, one or more of the disclosed modules or disclosed storage media may be internal or external to the disclosed systems. In some embodiments, one or more of the disclosed modules or storage media may be implemented via a computing "cloud", to which the disclosed system connects via a network connection and accordingly uses the external module or storage medium. In some embodiments, the disclosed storage media for storing information may include non-transitory computer-readable media, such as a flash memory. Further, in various embodiments, one or more of the storage media may be non-transitory computer-readable media that store data or computer programs executed by various modules, or implement various techniques or flow charts disclosed herein.

The above detailed description refers to the accompanying drawings. The same or similar reference numbers may have been used in the drawings or in the description to refer to the same or similar parts. Also, similarly named elements may perform similar functions and may be similarly designed, unless specified otherwise. Details are set forth to provide an understanding of the exemplary embodiments. Embodiments, e.g., alternative embodiments, may be practiced without some of these details. In other instances, well known techniques, procedures, and components have not been described in detail to avoid obscuring the described embodiments.

The foregoing description of the embodiments has been presented for purposes of illustration only. It is not exhaustive and does not limit the embodiments to the precise form disclosed. While several exemplary embodiments and features are described, modifications, adaptations, and other implementations may be possible, without departing from the spirit and scope of the embodiments. Accordingly, unless explicitly stated otherwise, the descriptions relate to one or more embodiments and should not be construed to limit the embodiments as a whole. This is true regardless of whether or not the disclosure states that a feature is related to "a,", "the," "one," "one or more," "some," or "various" embodiments. As used herein, the singular forms "a," "an," and "the" may include the plural forms unless the context clearly dictates otherwise. Further, the term "coupled" does not exclude the presence of intermediate elements between the coupled items. Also, stating that a feature may exist indicates that the feature may exist in one or more embodiments.

In this disclosure, the terms "include," "comprise," "contain," and "have," when used after a set or a system, mean an open inclusion and do not exclude addition of other, non-enumerated, members to the set or to the system. Further, unless stated otherwise or deducted otherwise from the context, the conjunction "or," if used, is not exclusive, but is instead inclusive to mean and/or. Moreover, if these terms are used, a subset of a set may include one or more than one, including all, members of the set.

Further, if used in this disclosure, and unless stated or deducted otherwise, a first variable is an increasing function of a second variable if the first variable does not decrease and instead generally increases when the second variable increases. On the other hand, a first variable is a decreasing function of a second variable if the first variable does not increase and instead generally decreases when the second variable increases. In some embodiment, a first variable may be an increasing or a decreasing function of a second variable if, respectively, the first variable is directly or inversely proportional to the second variable.

The disclosed systems, methods, and apparatus are not limited to any specific aspect or feature or combinations thereof, nor do the disclosed systems, methods, and apparatus require that any one or more specific advantages be present or problems be solved. Any theories of operation are to facilitate explanation, but the disclosed systems, methods, and apparatus are not limited to such theories of operation.

Modifications and variations are possible in light of the above teachings or may be acquired from practicing the embodiments. For example, the described steps need not be performed in the same sequence discussed or with the same degree of separation. Likewise various steps may be omitted, repeated, combined, or performed in parallel, as necessary, to achieve the same or similar objectives. Similarly, the systems described need not necessarily include all parts described in the embodiments, and may also include other parts not described in the embodiments. Accordingly, the embodiments are not limited to the above-described details, but instead are defined by the appended claims in light of their full scope of equivalents. Further, the present disclosure is directed toward all novel and non-obvious features and aspects of the various disclosed embodiments, alone and in various combinations and sub-combinations with one another.

While the present disclosure has been particularly described in conjunction with specific embodiments, many alternatives, modifications, and variations will be apparent in light of the foregoing description. It is therefore contemplated that the appended claims will embrace any such alternatives, modifications, and variations as falling within the true spirit and scope of the present disclosure.

What is claimed is:

1. A remote temperature detector system comprising:
   a reference thermal mass;
   a temperature sensor in thermal contact with the reference thermal mass for monitoring temperature thereof and generating temperature signals indicative of the monitored temperature;
   an infrared detector for detecting infrared radiation emitted by an external object and generating infrared detection signals;
   a processor in communication with the temperature sensor and the infrared detector to receive the temperature and infrared detection signals;
   a first visible spectrum imaging device;
   a second visible spectrum imaging device;
   a first polarizer disposed in front of the first visible spectrum imaging device for polarizing light in a first direction; and
   a second polarizer disposed in front of the second visible spectrum imaging device for polarizing light in a second direction perpendicular to the first direction,
   wherein:
      the processor is configured to adjust emissivity assigned to the external object based on visible spectrum imaging signals acquired from the first visible spectrum imaging device and the second visible spectrum imaging device; and
      the processor is configured to operate on the infrared detection signals and temperature signals to estimate temperature of the external object.

2. The system of claim 1, wherein the reference thermal mass is a black body object integrated with the system.

3. The system of claim 1, wherein:
   the system further comprises a housing; and
   the reference thermal mass and the infrared detector are disposed in the housing.

4. The system of claim 1, wherein a first distance to the reference thermal mass is different from a second distance to the object.

5. The system of claim 4, wherein the first distance is less than the second distance.

6. The system of claim 1, wherein the infrared detector comprises an uncooled microbolometer.

7. The system of claim 1, wherein the processor is configured to calibrate the infrared detection signals based on the temperature signals provided by the temperature sensor.

8. The system of claim 1, further comprising a distance sensor to measure a distance to the external object.

9. The system of claim 8, wherein the processor is configured to receive a value of the distance from the distance sensor and use the value of the distance to compensate the infrared detection signals for the distance between the infrared detector and the external object.

10. The system of claim 1, further comprising an ambient humidity sensor.

11. The system of claim 10, wherein the infrared detection signals are further compensated by an ambient humidity signal acquired by the ambient humidity sensor.

12. The system of claim 1, further comprising an ambient temperature sensor.

13. The system of claim 12, wherein the infrared detection signals are further compensated by an ambient temperature signal acquired by the ambient temperature sensor.

14. The system of claim 1, wherein the external object include a human body.

15. The system of claim 1, wherein the processor is configured to adjust emissivity assigned to the external object based on one or more of illumination conditions, geometric properties, and age.

16. The system of claim 1, wherein the emissivity is adjusted for water content present on the external object based on the visible spectrum imaging signals acquired from the first visible spectrum imaging device and the second visible spectrum imaging device.

* * * * *